(12) United States Patent
Chen et al.

(10) Patent No.: US 7,749,500 B2
(45) Date of Patent: Jul. 6, 2010

(54) ANTIBODIES TO IL-17 POLYPEPTIDES AND THERAPEUTIC USES THEREOF

(75) Inventors: Jian Chen, Princeton, NJ (US); Ellen Filvaroff, San Francisco, CA (US); Audrey Goddard, San Francisco, CA (US); Austin Gurney, Belmont, CA (US); Hanzhong Li, San Mateo, CA (US); William I. Wood, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/188,054

(22) Filed: Aug. 7, 2008

(65) Prior Publication Data

US 2009/0022725 A1 Jan. 22, 2009

Related U.S. Application Data

(63) Continuation of application No. 11/436,554, filed on May 19, 2006, now abandoned, which is a continuation of application No. 09/854,280, filed on May 10, 2001, now Pat. No. 7,115,398, which is a continuation of application No. 09/311,832, filed on May 14, 1999, now abandoned.

(60) Provisional application No. 60/085,579, filed on May 15, 1998, provisional application No. 60/113,621, filed on Dec. 23, 1998.

(51) Int. Cl.
*A61K 39/395* (2006.01)
*C12P 21/08* (2006.01)

(52) U.S. Cl. .............. 424/130.1; 530/387.1; 530/387.3; 530/387.9; 530/388.1; 530/388.23; 530/391.3; 530/351

(58) Field of Classification Search ........................ None
See application file for complete search history.

(56) References Cited

U.S. PATENT DOCUMENTS

| | | | |
|---|---|---|---|
| 5,536,637 | A | 7/1996 | Jacobs |
| 6,043,344 | A | 3/2000 | Jacobs et al. |
| 6,562,578 | B1 | 5/2003 | Gorman et al. |
| 2003/0003545 | A1 | 1/2003 | Ebner et al. |
| 2003/0049255 | A1 | 3/2003 | Sims et al. |
| 2003/0092133 | A1 | 5/2003 | Ebner et al. |
| 2003/0186387 | A1 | 10/2003 | Ebner et al. |
| 2007/0172457 | A1* | 7/2007 | Ebner et al. ................ 424/85.2 |

FOREIGN PATENT DOCUMENTS

| | | |
|---|---|---|
| CA | 2378519 | 1/2001 |
| CA | 2401273 | 9/2001 |
| CA | 2403370 | 9/2001 |
| CA | 2343569 | 3/2003 |
| EP | 1 386 931 | 2/2004 |
| EP | 1 443 055 | 8/2004 |
| EP | 1 326 974 | 12/2006 |
| WO | WO 95/18826 | 7/1995 |
| WO | WO 96/29408 | 9/1996 |
| WO | WO 97/04097 | 2/1997 |
| WO | WO 98/49310 | 11/1998 |
| WO | WO 99/03982 | 1/1999 |
| WO | WO 99/14240 | 3/1999 |
| WO | WO 99/14240 A1 | 3/1999 |
| WO | WO 99/32632 | 7/1999 |
| WO | WO 99/35267 | 7/1999 |
| WO | WO 99/61617 | 7/1999 |
| WO | WO 99/46281 | 9/1999 |
| WO | WO 99/60127 | 11/1999 |
| WO | WO 00/20593 | 4/2000 |
| WO | WO 00/53752 | 9/2000 |
| WO | WO 0070050 | 11/2000 |
| WO | WO 00/73452 | 12/2000 |
| WO | WO 01/04304 | 1/2001 |
| WO | WO 01/16318 | 3/2001 |
| WO | WO 01/46420 | 6/2001 |
| WO | WO 01/49728 A2 | 7/2001 |
| WO | WO 01/54477 A2 | 8/2001 |
| WO | WO 01/55204 A1 | 8/2001 |
| WO | WO 01/57202 A2 | 8/2001 |
| WO | WO 01/68705 A2 | 9/2001 |

(Continued)

OTHER PUBLICATIONS

Database EMBL, "*Homo sapiens* chromosome 3 clone RP11-1020A11 map 3p, complete sequence", Accession No. AC018809, Dec. 23, 1999.
Database EMBL, "*Homo sapiens* IL-17 receptor homolog precursor (EVI27) mRNA, complete cds", Accession No. AF208110, Jul. 18, 2000.
Database EMBL, "*Homo sapiens* IL-17RE mRNA, complete cds", Accession No. AF458069, Aug. 12, 2002.
Database Uniprot, "Uncharacterized protein IL17RE (Fragment)", Accession No. A6NL85, Jul. 24, 2007.
Database Uniprot, "Interleukin-17 receptor E precursor (IL-17 receptor E) (IL-17RE)", Accession No. Q8NFR9, Oct. 1, 2002.
Database Uniprot, "Interleukin-17 receptor B precursor (IL-17 receptor B) (IL-17RB) (Interleukin-17B receptor) (IL-17B receptor) (IL-17 receptor homolog 1) (IL-17Rh1) (IL17Rh1) (Cytokine receptor CRL4)", Accession No. Q9NRM6, May 27, 2002.

(Continued)

*Primary Examiner*—Dong Jiang
(74) *Attorney, Agent, or Firm*—Bonny Yeung, Esq.; Ginger R. Dreger, Esq.; Arnold & Porter LLP

(57) ABSTRACT

The present invention is directed to novel polypeptides having sequence identity with IL-17 and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided herein are methods for treating degenerative cartilaginous disorders.

28 Claims, 13 Drawing Sheets

FOREIGN PATENT DOCUMENTS

| | | |
|---|---|---|
| WO | WO 01/68848 | 9/2001 |
| WO | WO 01/90358 | 11/2001 |
| WO | WO 02/00690 | 1/2002 |
| WO | WO 02/08284 | 1/2002 |
| WO | WO 02/08285 A2 | 1/2002 |
| WO | WO 2004/042009 | 5/2004 |
| WO | WO 2005/000897 | 1/2005 |
| WO | WO 2005/010044 | 2/2005 |
| WO | WO 2006/132788 | 12/2006 |

OTHER PUBLICATIONS

Fossiez et al., "T Cell Interleukin-17 Induces Stromel Dells to Produce Proinflammatory and Hematopoietic Cytokines" Journal of Experimental Medicine, J.P., Tokyo, 183(2):2593-2603 (1996), XP002035506, ISSN: 0022-1007.

L. Hillier et al., "WashU-NCI Human EST Project" EMBL Database entry AA780147, Accession No. AA780147 (1998), XP002123461.

L. Hillier et al., "The WashU Merck EST Project" EMBL Database entry HSA33733, Accession No. AA033733 (1986), XP002073848.

Li, et al., "Identification and functional characterization of a novel interleukin 17 receptor: A possible mitogenic activation through ras/mitogen-activated protein kinase signaling pathway", Cellular Signalling, vol. 18, No. 8, pages.

Shi, et al., "A novel cytokine receptor-ligand pair: Identification, molecular characterization and in vivo immunomodulatory activity", Journal of Biological Chemistry, vol. 275, No. 23, pp. 19167-19176, Jun. 23, 2000.

Titan, et al., "EVI127 encodes a novel membrane protein with homology to the IL17 receptor", Oncogene, vol. 19, No. 17, pp. 2098-2109, Apr. 20, 2000.

Yao, et al., "Molecular characterization of the human interleukin (IL)-17 receptor", Cytokine, vol. 9, No. 11, pp. 794-800, Nov. 1997.

Yao et al., "Human IL-17: A novel Cytokine Derived from T Cells" Journal of Immunology, US, The Williams and Williams Co., Baltimore, 155(12):5483-5486 (1995), XP000602481, ISSN: 0022-1767.

Aarvak et al., "IL-17 Is Produced by some Proinflammatory Th1/Th0 Cells but not by Th2 Cells" Journal of Immunology 162 :1246-1251 (1999).

Albanesi et al., "IL-17 Is Produced by Nickel-Specific T Lymphocytes and Regulates ICAM-1 Expression and Chemokine Production in Human Keratinocytes: Synergistic or Antagonist Effects with IFN-γ and TNF-α" Journal of Immunology 162 :494-502 (1999).

Altschul et al., "Local alignment statistics" Methods in Enzymology 266:460-480 (1996).

Antonysamy et al., "Evidence for a role of IL-17 in organ allograft rejection: IL-17 promotes the functional differentiation of dendritic cell progenitors" J. Immunol. 162 (1) :577-584 (1999).

Antonysamy, M.A. et al., Evidence for a role of IL-17 in alloimunity: a novel IL-17 antagonist promostes heart graft survival: Transplant Proc. 31(1-2) :93 (1999).

Arend et al., "Cytokines and Cytokine Inhibitors or Antagonists in Rheumatoid Arthritis" Arthritis Rheum. 33:305-315 (1990).

Ashok R. Amin et al., "The role of nitric oxide in articular cartilage breakdown in osteoarthritis" Current Opinion in Rheumatology 10(3) :263-268 (1998).

Attur et al., "Interleukin-17 Up-Regulation of Nitric Oxide Production in Human Osteoarthritis Cartilage" Arthritis and Rheumatism 40 (6) :1050-1053 (Jun. 1997).

Awane et al., "NF-κB-Inducing Kinase is a Common Mediator of IL-17-TNF-α, and IL-1β-Induced Chemokine Promoter Activation in Intestinal Epithelial Cells" J. Immunol 162 :5337-5344 (1999).

Biesinger et al., "Stable growth transformation of human T lymphocytes by Herpesvirus saimiri" Proc. Natl. Acad. Sci. USA 89:3116-3119 (Apr. 1992).

BLAST Results A-1-A-1 (Dayhoff).

BLAST Results B-1-B-10 (Dayhoff).

Broxmeyer, H.E., "Is Interleukin 17, An Inducible Cytokine That Stimulates Production of Other Cytokines, Merely a Redundant Player in al Sea of Other Biomolecules?" Journal of Experimental Medicine 183 :2411-2415 (Jun. 1996).

Chabaud et al., "Enhancing Effect of IL-17 on IL-1-Induced IL-6 and Leukemia Inhibitory Factor Production by Rheumatoid Arthritis Synoviocytes and Its Regulation by Th2 Cytokines" Journal of Immunology 161 :409-414 (1998).

Chabaud et al, "Human Interleukin-17: A T Cell-Derived Proinflammatory Cytokine Produced by the Rheumatoid Synovium" Arthritis &. Rheumatism 42(5) :963-970 (1999).

Farndale et al., "Improved quantification and discrimination of sulphated glycosaminoglycans by use of dimethylmethylene blue" Biochem. Biophys. Acta 883 :173-177 (1986).

Fleckenstein and Desrosiers, "Herpesvirus saimiri and herpesvirus ateles" In the Herpesviruses, I. B. Roizman, ed., NY:Plenum Publishing Press pp. 253-332 (1982).

Fossiez et al., "Interleukin-17" Int. Rev. Immunol. 16 (5-6) :541-551 (1998).

Fossiez et al., "T Cell Interleukin-17 induces Stromal Cells to Produce Proinflammatory and Hematopoietic Cytokines" Journal of Experimental Medicine 183 (6) :2593-2603 (Jun. 1996).

Gordon et al., "Molecular immunobiology of macrophages: recent progress" Current Opinion In Immunology 7: 24-33 (1995).

Hillier et al., "af37c02.s1 Soares total fetus Nb2HF8 9w Homo sapiens cDNA clone 1033826 3"(Accession No. AA780147) (Feb. 6, 1998).

Hillier et al., "zf01f09. sl Soares fetal heart NbHHI9W Homo sapiens cDNA clone 375689 3" (Accession No. AA033733) (Feb. 4, 1997).

Jovanovic et al., "IL-17 Stimulates the Production and Expression of Proinflammatory Cytokines, IL-β and TNF-α, by Human Macrophages" J. Immunol 160 :3513-3521 (1998).

Jovanovic et al., "Stimulation of 92-kd gelatinase (matrix metalloproteinase 9) production by interleukin-17 in human monocyte/macrophages" Arthritis and Rheumatism 43(5) :1134-1144 (2000).

Kennedy et al., "Mouse IL-17: A Cytokine Preferentially Expressed by αβTRC+CD4-CD8—T Cells" Journal Interferon and Cytokine Research 16(8) :611-617 (1996).

Kingsley et al., "Joint destruction in rheumatoid arthritis: biological bases" Clin. Exp. Rheumatol. 15 :S3-S14 (1997).

Klein et al., "Selection for Genes Encoding Secreted Proteins and Receptors" Proc. Natl. Acad. Sci. USA 93(14):7108-7113 (1996).

Kong et al., "Activated T cells regulate bone loss and joint destruction in adjuvant arthritis through osteoprotegerin ligand" Nature 402(6759) :304-309 (1999).

Kotake et al., "IL-17 in synovial fluids from patients with rheumatoid arthritis is a potent stimulator of osteoclastogenesis" Journal of Clinical Investigation 103(9) :1345-1352 (1999).

Lennon et al., "The I.M.A.G.E. Consortium: An Integrated Molecular Analysis of Genomes and Their Expression" Genomics (Article #0177) 33:151-152 (1996).

Li et al., "Cloning and characterization of the IL-17B and IL-17C two new members of the IL-17 cytokine family" Proc. Natl. Acad. Sci. USA 97(2) :773-778 (2000).

Lotz et al., "IL-17 Promotes Cartilage Degradation" Cytokines (ACR Abstract Session 10, Oct. 19, 1996, abstract #559) pp. S120 (1996).

Luckow et al., "Trends in the Development of Baculovirus Expression Vectors" Bio/Technology 6 :47-55 (1988).

March et al., "Cloning, sequence and expression of two distinct human interleukin-1 complementary DNAs" Nature 315 :641-647 (Jun. 20, 1985).

Marra et al. "The WashU-HHMIMouse EST project, Locus AA763404, Jan. 27, 1998, Accessed Dec. 13, 2000".

Martel-Pelletier et al., "Major Signaling Pathways Involved in the IL-17 Induced Nitric Oxide (NO) Production in Human Osteoarthritic Chondrocytes" Orthopaedic Research Society (45th Annual Meeting, Feb. 1-4, 1999, pt 2) 24:595 (1999).

Matusevicius et al., "Interleukin-17 mRNA expression in blood and CSF mononuclear cells is augmented in multiple sclerosis" Multiple Sclerosis 5: 101-104 (1999).

Rouvier et al,. "CTLA-8, Cloned from an Activated T Cell, Bearing AU-Rich Messenger RNA Instability Sequences, and Homologous to a Herpesvirus Saimiri Gene" Journal of Immunology 150(12) :5445-5456 (Jun. 15, 1993).

Schwartzenberger et al., "IL-17 Stimulates Granulopoiesis in Mice: Use of an Alternate, Novel Gene Therapy-Derived Method for In Vivo Evaluation of Cytokines" *Journal of Immunology* 161:6383-6389 (1998).

Seow, H.F., "Pathogen interactions with cytokines and host defence: an overview" *Vet Immunol. Immunopathol.* 63(1-2):139-148 (1998).

Shalom-Barak et al., "Interleukin-l7-induced 17 Gene Expression in Articular Chondrocytes is Associated with Activation of Mitogen-activated Protein Kinases and NF-κB" *Journal of Biological Chemistry* 273(42):27467-27473 (Oct. 16, 1998).

Shi, "A novel cytokine receptor-ligand pair: Identification, molecular characterization and in vivo immunodulatory activity" *Journal of Biological Chemistry, American Society of Biological Chemists*, Baltimore 275(25): 19167-19176 (Jun. 23, 2000).

Spriggs, M.K., "Interleukin-17 and Its Receptor" *Journal of Clinical Immunology* 17(5):366-369 (1997).

Subramaniam et al., "Evidence for the Involvement of JAK/STAT Pathway In the Signaling Mechanism of Interleukin-17" *Biochem. & Biophys. Res. Comm.* 262: 14-19 (1999).

Subramaniam et al., "Interleukin-17 Induces Rapid Tyrosine Phosphorylation and Activation of Raf-1 Kinase in Human Monocytic Progenitor Cell Line U937" *Biochem. & Biophys. Res. Comm.* 259: 172-177 (1999).

Tartour et al., "Interleukin 17, a T-cell-derived Cytokine, Promotes Tumorigenicity of Human Cervical Tumors in Nude Mice" *Cancer Research* 59: 3698-704 (1999).

Teunissen et al., "Interleukin-17 and Interferon-γ Synergize in the Enhancement of Proinflammatory Cytokine Production by Human Keratinocytes" *J. Invest. Dermatol.* 111: 645-649 (1998).

Van Bezooijen et al., "Interleukin-17: A New Bone Acting Cytokine In Vitro" *Journal of Bone and Mineral Research* 14(9):1513-1521 (1999).

Van Kooten et al., "Interleukin-17 Activates Human Renal Epithelial Cells in Vitro and is Expressed during Renal Allograft Rejection" *J. Am. Soc. Nephrol.* 9: 1526-1534 (1998).

Vukicevic et al., "Induction of nephrongenic mesenchyme by osteogenic protein 1 (bone morphogenetic protein 7)" *Proc. Natl. Acad. Sci.* 93: 9021-9026 (1996).

Yao et al., "Herpesvirus Saimiri Encodes a New Cytokine, IL-17, which Binds to a Novel Cytokine Receptor" *Immunity* 3:811-821 (Dec. 1995).

Yao et al., "Human IL-17: A Novel Cytokine Derived from T Cells" *Journal of Immunology* 155(12): 5483-5486 (1995).

Yao et al., "Molecular Characterization of the Human Interleukin (IL)-17 Receptor" *Cytokine* 9(11): 794-800 (Nov. 1997).

Ziolkowska et al., "High Levels of IL-17 in Rheumatoid Arthritis Patients: IL-15 Triggers In Vitro IL-17 Production Via Cyclosporin A-Sensitive Mechanism" *Journal of Immunology* 164(5): 2832-2838 (2000).

Genbank, Acc# AL132 (Nov. 15, 1999).

U.S. Appl. No. 60/087,340, filed May 29, 1998, Ebner, et al.
U.S. Appl. No. 60/099,805, filed Sep. 10, 1998, Ebner, et al.
U.S. Appl. No. 60/131,965, filed Apr. 30, 1999, Ebner, et al.

Aggarwal, S., et al., *The Journal of Biological Chemistry*—278(3):1910-1914 (2003).

Aggarwal, S., et al., *Journal of Leukocyte Biology*—71:1-8 (2002).
Becher, B., et al., *The Journal of Clinical Investigation*—112(8):1186-1191 (2003).
Becher, B., et al., *The Journal of Clinical Investigation*—110(4):493.497 (2002).
Burchill, M.A., et al., *Infection and Immunity*—71(6):3437-3442 (2003).
Bush, K.A., et al., *Arthritis & Rheumatism*—46(2):802-805 (2002).
Constantinescu, C.S., et al., *The Journal of Immunology*—161:5097-5104 (1998).
Cua, D.J., et al., *Letters to Nature*—421:744-748 (2003).
Dubowchik, G.M., et al., *Pharmacology & Therapeutics*—83:67-123 (1999).
Goodin, D.S., et al., *Neurology*—58:169-178 (2001).
Haak, S., et al., *The Journal of Clinical Investigation*—119(1):61-69 (2009).
Jonker, M., et al., *Human Immunology*—32:31-40 (1991).
Joosten, L.A.B., et al., *The Journal of Immunology*—159:4094-4102 (1997).
Kuestner, R.E., et al., *The Journal of Immunology*—179:5462-5473 (2007).
Lock, C., et al., *Nature Medicine*—8(5):500-508 (2002).
Lubberts, E., et al., *The Journal of Immunology*—167: 1004-1013 (2001).
Nakae, S., et al., *Immunity*—17:375-387 (2002).
Nakae, S., et al., *The Journal of Immunology*—171:6173-6177 (2003).
Okuda, Y., et al., *Journal of Neuroimmunology*—101:188-196 (1999).
Ozenci, V., et al., *Multiple Sclerosis*—8:396-404 (2002).
Singh, V.K., et al., *Immunologic Research*—20:147-161 (1999).
Tarner, I.H., et al., *Current Opinion in Immunology*—13:676-682 (2001).
Tompkins, S.M., et al., *Nature Medicine*—8(5):451-453 (2002).
Wiendl, H., et al., *Biodrugs*—16(3):183-200 (2002).
Witowski, J., et al., *The Journal of Immunology*—165:5814-5821 (2000).
Yamaguchi, Y., et al., *The Journal of Immunology*—179:7128-7136 (2007).
Yazaki, P.J., et al., *Protein Engineering, Design & Selection*—17(5):481-489 (2004).
Zhang, G-X., et al., *The Journal of Immunology*—170:2153-2160 (2003).
Ely, et al., Nature Immunology, vol. 10, No. 12, pp. 1245-1252, (2009).
Fleit, et al., Journal of Leukocyte Biology, 49: 556-565, (1991).
Hymowitz, et al., The EMBO Journal, vol. 20, No. 19, pp. 5332-5341, (2001).
Lee, et al., The journal of Biological Chemistry, vol. 276, No. 2, pp. 1660-1664, (2001).
Rickel, et al., The Journal of Immunology, 181: 4299-4310, (2008).
Toy, et al., The journal of Immunology, 177: 36-39, (2006).

* cited by examiner

FIGURE 1A

```
hIL17    1   · · · · · · · · · · · · · · · · · · · · · · · · · · · · · · · · · · · · · · · · · · MTPGKTSLVSLLLL
hIL17B   1   · · · · · · · · · · · · · · · · · · · · · · · · · MDWPHNLLFLLTISIFLGLGQPRSPKSKRKGQGRPLAPGP
hIL17C   1   MTLLPGLLFLTWLHTCLAHHDPSLRGHPHSHGTPHCYSAEELPLGQAPPH hIL17    16  SLEAIVKAGITIPRNPGCPNSEDKNFPRTVMVNLNIHNRNTNPKASSD
hIL17B   43  HQVPLDLVSRMKPYARMEEYERNIEEMVAQLRNSSELAQRKCEVNLQLWM
hIL17C   51  LARGAKWGQALPVALVSSLEAASHRGRHERPSATTQCPVLRPEEVLEAD hIL17    66  YYNRSTSPWNLHRNEDPERYPSVIWEAKCRHLGCINADGNVDYHMNSVPI
hIL17B   93  SNKRSLSPWGYSINHDPSRIPVDLPEARGLCLGCVNPFTMQEDRSMVSVP
hIL17C   101 THQRSISPWRYRVDTQEDRYPQKLAFAECLCRGCIDARIGRETAALNSVR hIL17    116 QQEI·LVLRREPPHCPNS· · · · · · ·ERLEKLSVGCTCVTPIVHHVA
hIL17B   143 VFSQVPVRRRL· · ·CPPPPRT· · ·GPCRQAVMETIAVGCTQIF· · · · · ·
hIL17C   151 LLQSLLVLRRRPQSRDGSGLPTPGAFAEHTEFHMPVGCTCVLRRSV· · ·
```

Tue Apr 27 16:58:30 1999
/home/ruby/va/Molbio/carpenda/temp/aa.out

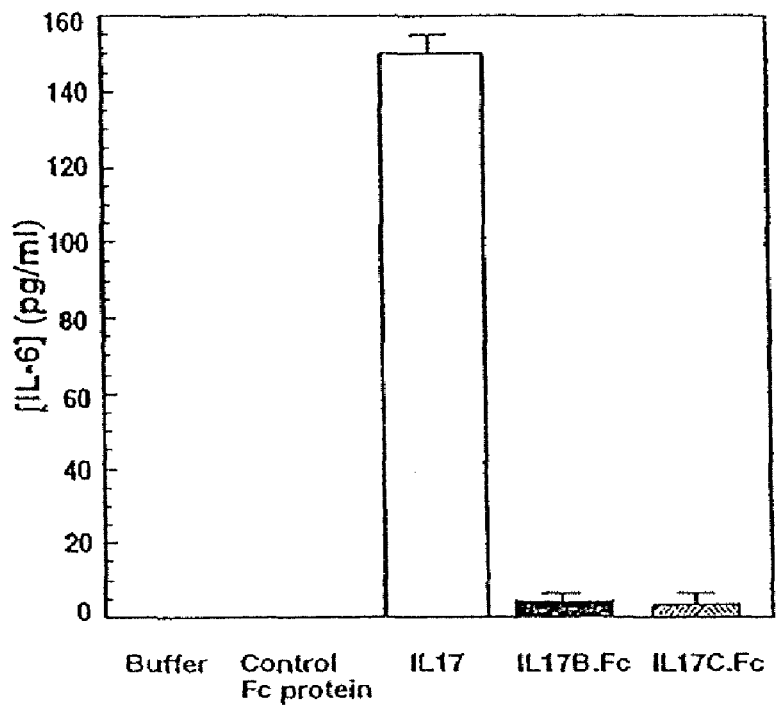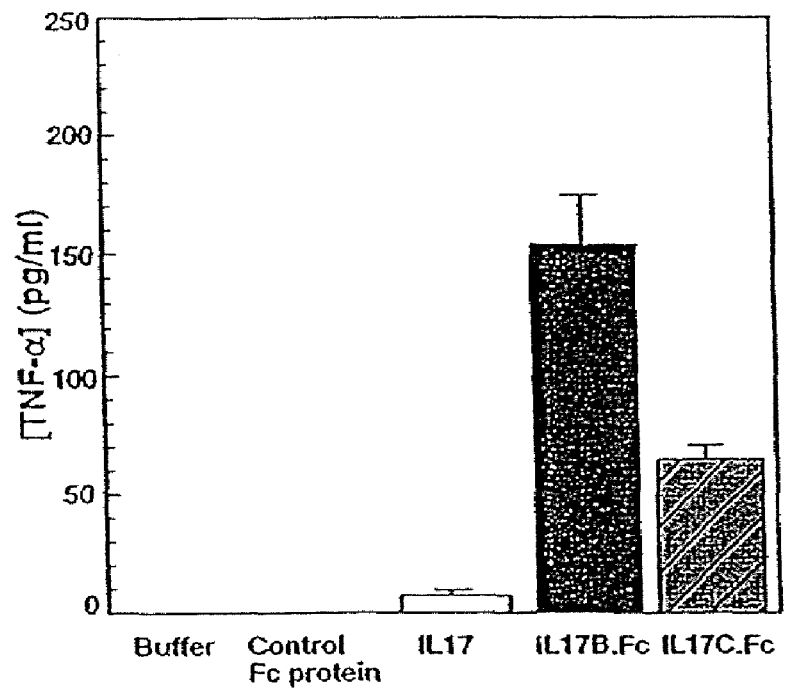
FIGURE 3

Inhibition of nitric oxide release does not block the detrimental effects of IL 17 on matrix breakdown or synthesis
A.
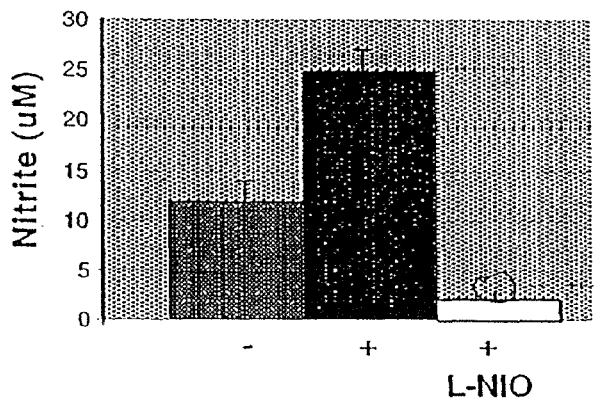
B.
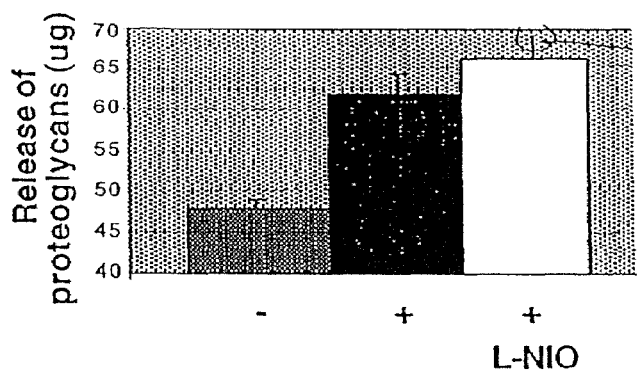
C.
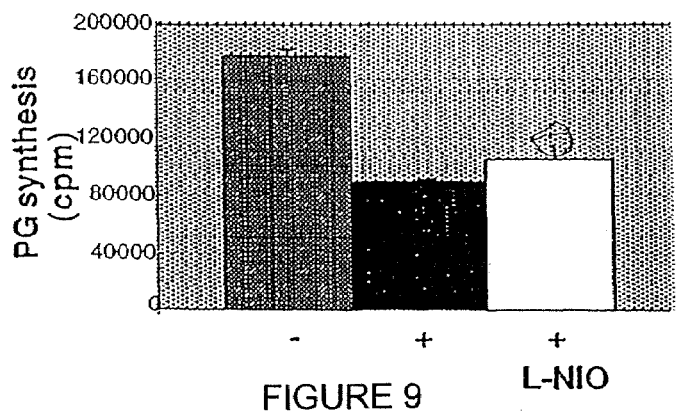
FIGURE 9

ANTIBODIES TO IL-17 POLYPEPTIDES AND THERAPEUTIC USES THEREOF

RELATED APPLICATIONS

This application is a continuation of, and claims priority under 35 U.S.C. §120 to, U.S. patent application Ser. No. 11/436,554, filed May 19, 2006, now abandoned, which is a continuation of, and claims priority under 35 U.S.C. §120 to, U.S. patent application Ser. No. 9/854,280, filed May 10, 2001, now U.S. Pat. No. 7,115,398, which is a continuation of U.S. patent application Ser. No. 09/311,832, filed May 14, 1999, now abandoned, and claims benefit of U.S. Provisional Application Ser. No. 60/085,579, filed May 15, 1998, and U.S. Provisional Application Ser. No. 60/113,621, filed Dec. 23, 1998, the entirety of which are incorporated herein by reference.

FIELD OF THE INVENTION

The present invention relates generally to the identification and isolation of novel DNA, therapeutic uses and the recombinant production of novel polypeptides having sequence identity with the cytokine IL-17, and cytotoxic T-lymphocyte-associated antigen 8 (CTLA-8) designated herein as PRO1031 and PRO1122 polypeptides.

BACKGROUND OF THE INVENTION

It has been reported that the cytokine interleukin 17 (IL-17) stimulates epithelial, endothelial, and fibroblastic cells to secrete cytokines such as IL-6, IL-8, and granulocyte-colony-stimulating factor, as well as prostaglandin E2. While expression of IL -17 is restricted to activated T cells, the IL-17 receptor is widely expressed, a property consistent with the pleiotropic activities of IL-17. Moreover, it has been shown that when cultured in the presence of IL-17, fibroblasts could sustain proliferation of CD34+ preferential maturation into neutrophils. As a result, IL-17 could be an early potentiator or even maintainer of T cell-dependent inflammatory reaction and/or an element of the cytokine network that bridges the immune system to hematopoiesis. See, Yao, et al., *J. Immunol.,* 155(12):5483-5486 (1995); Fossiez, et al., *J. Exp. Med.,* 183(6):2593-2603 (1996); Kennedy, et al., *J. Interferon Cytokine Res.,* 16(8):611-617 (1996).

More generally, all novel proteins are of interest. Extracellular proteins play an important role in the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents.

Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.,* 93:7108-7113 (1996); U.S. Pat. No. 5,536,637)]. The results of such efforts are presented herein.

Interleukin-17 is a recently described, T cell-derived cytokine, the biological functions of which are only beginning to be understood. Spriggs et al, *J. Clin. Immunol.* 17: 366 (1997); Broxmeyer, H. E., *J. Exp. Med.* 183: 2411 (1996). When IL-17 was initially identified as a cDNA clone from a rodent T-cell lymphoma, it was recognized as having a sequence similar to an open reading frame from a primate herpesvirus, Herpervirus saimiri Rouvier et al., *J. Immunol.* 150: 5445 (1993), Yao et al., *Immunity* 3: 811 (1995) [Yao-1], Fossiez et al, *J. Exp. Med.* 183: 2593 (1996). Subsequently, it has been confirmed that this viral protein has many if not all of the immunostimulatory activities found for the host IL-17. Fleckenstein and Desrosiers, "Herpesvirus saimiri and herpesvirus ateles," In *The Herpesviruses*, I. B. Roizman, ed, Plenum Publishing Press, New York, p. 253 (1982), Biesinger, B. I. et al., *Procl Natl Acad. Sci. USA* 89: 3116 (1992).

Human IL-17 is a 20-30 kDa, disulfide linked, homodimeric protein with variable glycosylation. Yao-1, supra; Fossier et al, supra. It is encoded by a 155 amino acid open reading frame that includes an N-terminal secretion signal sequence of 19-23 amino acids. The amino acid sequence of IL-17 is only similar to the Herpesvirus protein described above and does not show significant identity with the sequences of other cytokines or other known proteins. Additionally, the IL-17 encoding mRNA has been detected has only been detected in activated CD4$^+$ memory T cells and PMA/ionomycin stimulated PBMC cells.

Despite its restricted tissue distribution, IL-17 exhibits pleiotropic biological activities on various types of cells, such as fibroblasts, endothelial cells and epithelial cells. Spriggs, M. K., supra.; Broxmeyer, H. E., supra. IL-17 has been found to stimulate the production of many cytokines: TNF-α and IL-1β from macrophages [Jovanovic et al., *J. Immunol* 160: 3513 (1998)]; IL-6, IL-8 and the intracellular adhesion molecule (ICAM-1) from human fibroblasts. Fossiez et al., supra, Yao et al., *J. Immunol.* 155: 5483 (1995) [Yao-2]; granulocyte-colony-stimulating factor (G-CSM) and prostaglandin (PGE-2) form synoviocytes, Fossiez et al., supra. Through the induction of a number of cytokines, IL-17 is able to mediate a wide-range of response, mostly proinflammatory and hematopoietic. This has led to the suggestion that IL-17 may play a pivotal role in initiating or sustaining an inflammatory response. Jovanovic et al., supra.

Consistent with IL-17's wide-range of effects, the cell surface receptor for IL-17 has been found to be widely expressed in many tissues and cell types Yao et al., *Cytokine* 9: 794 (1997) [Yao-3]. While the amino acid sequence of the hIL-17 receptor (866 a.a.) predicts a protein with a single transmembrane domain and a long, 525 amino acid intracellular domain, the receptor sequence is unique and is not similar to that of any of the receptor from the cytokine/growth factor receptor family. This coupled with the lack of similarity of IL-17 itself to other known proteins indicates that IL-17 and its receptor may be part of a novel family of signaling proteins and receptors.

IL-17 has further been shown, by intracellular signaling, to stimulate transient Ca$^{2+}$ influx and a reduction in [cAMP]$_i$ in human macrophages. Jovanovic et al., supra. Fibroblasts and macrophages treated with IL-17 induce the activation of NF-κB, Yao-1, supra, Jovanovic et al, supra., while macrophages treated with it activate NF-κB and mitogen-activated protein kinases. Shalom-Barek et al., *J. Biol. Chem.* 273: 27467 (1998).

The present invention describes the cloning and characterization of two novel proteins, termed PRO1031 (IL-17B) and PRO1122 (IL-17C), and active variants thereof, that are similar in amino acid sequence to IL-17.

SUMMARY OF THE INVENTION

Applicants have identified a cDNA clone that encodes a novel polypeptide having sequence identity with IL-17, wherein the polypeptide is designated in the present application as "PRO1031" or "PRO1122".

In one embodiment, the invention provides an isolated nucleic acid molecule comprising DNA encoding a PRO1031 or PRO1122 polypeptide.

In one aspect, the isolated nucleic acid comprises DNA encoding the PRO1031 or PRO1122 polypeptide having amino acid residues: from about 21 through 180 of SEQ ID NO:1, or from about 19 through 197 of SEQ ID NO:3, respectively, or is complementary to such encoding nucleic acid sequence, and remains stably bound to it under at least moderate, and optionally, under high stringency conditions.

In another embodiment, the isolated nucleic acid comprises DNA having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to (a) a DNA molecule encoding a PRO1031 or PRO1122 polypeptide comprising the sequence of amino acid residues from 1 or about 21 to 180, inclusive, of SEQ ID NO: 1 or from 1 or about 19 to 197, inclusive, of SEQ ID NO: 3, or the (b) the complement of the DNA molecule of (a). Alternatively, the isolated nucleic acid comprises DNA encoding the PRO1031 polypeptide having amino acid residues 1 through 180, inclusive, of SEQ ID NO:3. Alternatively, the isolated nucleic acid comprises DNA encoding a 1122 polypeptide having the sequence of amino acid residues from about 1 to about 197, inclusive of SEQ ID NO: 1.

In another aspect, the invention concerns an isolated nucleic acid molecule encoding a PRO1031 or PRO1122 polypeptide comprising DNA hybridizing to the complement of the nucleic acid between about residues: (a) 42 to about 581, inclusive, of SEQ ID NO:2, or (b) 49 to about 640, inclusive, or SEQ ID NO: 4, respectively. Preferably, the hybridization range extends from about nucleic acid residue (a) about 102 to about 581, inclusive, of SEQ ID NO:2, or (b) about 104 to about 640, inclusive, of SEQ ID NO:4, respectively. Preferably, hybridization occurs under stringent hybridization and wash conditions.

In another aspect, the invention concerns an isolated nucleic acid molecule encoding an active PRO1031 or PRO1122 polypeptide comprising a nucleotide sequence that hybridizes to the complement of a nucleic acid sequence that encodes amino acids (a) 1 or about 21 to about 180, inclusive, of SEQ ID NO:1, or (b) 1 or about 19 to about 197, inclusive, of SEQ ID NO:3. Preferably, hybridization occurs under stringent hybridization and wash conditions.

In a further aspect, the invention concerns an isolated nucleic acid molecule comprising DNA having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to (a) a DNA molecule encoding the same mature polypeptide encoded by the human protein cDNA in ATCC deposit No. 209866 (DNA59294-1381) or 203552 (DNA62377-1381-1). In a preferred embodiment, the nucleic acid comprises DNA encoding the same mature polypeptide encoded by the human protein cDNA in ATCC deposit number 209866 (DNA59294-1381) or 203552 (DNA62377-1381-1), deposited on 14 May 1998 and 22 Dec. 1998, respectively. In a more preferred embodiment, the nucleic acid comprises the cDNA insert of ATCC deposit DNA59294-1381 (ATCC 209866) deposited on 14 May 1998 or DNA62377-1381-1 (ATCC 203552), deposited on 22 Dec. 1998, respectively.

In another aspect, the invention concerns an isolated nucleic acid molecule comprising a nucleotide sequence encoding a protein having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to (a) the full-length polypeptide encoded by the cDNA deposited with the ATCC on (1) 14 May 1998 under ATCC Deposit No.: 209866 (DNA59294-1381) or (2) 22 Dec. 1998 under ATCC Deposit No.: 203552 (DNA62377-1381-1), or (b) the complement of the nucleotide sequence of (a). In a preferred embodiment, the isolated nucleic acid molecule encodes the same full length polypeptide as the cDNA deposit of ATCC Deposit No.: 209866 or 203552, respectively.

In a further aspect, the isolated nucleic acid molecule comprises a nucleotide sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity, to: (a) DNA molecule comprising the sequence of nucleotides from about 42 or about 102 to about 581, inclusive, of SEQ ID NO:2 or from about 49 or about 104 to about 640, inclusive, of SEQ ID NO:4; or (b) the complement of the DNA molecule of (a).

In another aspect, the isolated nucleic acid molecule comprises: (a) the nucleotide sequence from about 42 or about 102 to about 581, inclusive, of SEQ ID NO:2 or from about 49 or about 104 to about 640, inclusive, of SEQ ID NO:4; or (b) the complement of the DNA molecule of (a).

In a further aspect, the invention concerns an isolated nucleic acid molecule produced by hybridizing a test DNA molecule under stringent conditions with: (a) a DNA molecule encoding (i) a PRO1031 polypeptide having the sequence of amino acid residues from about 1 or about 21 to about 180, inclusive, of SEQ ID NO: 1, or (ii) a PRO1122 polypeptide having the sequence of amino acid residues from about 1 or about 19 to about 197, inclusive, of SEQ ID NO:3; or (b) the complement of the DNA molecule of (a), and if the DNA molecule has at least about an 80% sequence identity, preferably at least about an 81% sequence identity, more preferably at least about a 82% sequence identity, yet more preferably at least about a 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to (a) or (b), isolating the test DNA molecule.

In yet a further aspect, the invention concerns an isolated nucleic acid molecule comprising: (a) DNA encoding a polypeptide scoring at least about 80% positives, preferably at least about 81% positives, more preferably at least about 82% positives, yet more preferably at least about 83% positives, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives, yet more preferably at least about 99% positives, when compared with the amino acid sequence of residues about (i) 21 to about 180, inclusive, of SEQ ID NO:1, or (ii) 19 to about 197, inclusive, of SEQ ID NO:3, or (b) the complement of the DNA of (a).

In a specific aspect, the invention provides an isolated nucleic acid molecule comprising DNA encoding a PRO1032 or PRO1122 polypeptide without the N-terminal signal sequence and/or initiating methionine, or is complementary to such encoding nucleic acid molecule. The signal peptide has been tentatively identified as extending from about amino acid residue (a) 1 to about amino acid residue 20, inclusive, in the sequence of SEQ ID NO:1, or (b) 1 to about amino acid residue 18, inclusive, in the sequence of SEQ ID NO:3. It is noted, however, that the C-terminal boundary of the signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art. Nielsen et al., *Prot. Engin.* 10:1-6 (1997), von Heinje et al., *Nucl. Acids Res.* 14: 4683-4690 (1986). Moreover, it is also recognized that, in some cases, cleavage of the signal sequence form a secreted polypeptide is not entirely uniform, resulting in more than one secreted species. These polypeptides, and the polynucleotides encoding them, are contemplated by the present invention. A such, for purposed of the present application, the signal peptide of the PRO1032 or PRO1122 polypeptide shown in SEQ ID NO:1 or SEQ ID NO:3, respectively, extends from amino acids 1 to X, wherein X is any amino acid from (a) 15 to 25 of SEQ ID NO:1, or (b) 13 to 23 of SEQ ID NO:3.

Another embodiment is directed to fragments of a PRO1031- or PRO1122-encoding sequence that may find use as, for example, hybridization probes or for encoding fragments of a PRO1031 or PRO1122 polypeptide that may optionally encode a polypeptide comprising a binding site for an anti-PRO1031 or anti-PRO1122 antibody. Such nucleic acids fragments are usually at least about 20 nucleotides in length, preferably at least about 30 nucleotides in length, more preferable at least about 40 nucleotides in length, yet more preferably at least about 50 nucleotides in length, yet more preferably at least about 60 nucleotides in length, yet more preferably at least about 70 nucleotides in length, yet more preferably at least about 80 nucleotides in length, yet more preferably at least about 90 nucleotides in length, yet more preferably at least about 100 nucleotides in length, yet more preferably at least about 110 nucleotides in length, yet more preferably at least about 120 nucleotides in length, yet more preferably at least about 130 nucleotides in length, yet more preferably at least about 140 nucleotides in length, yet more preferably at least about 150 nucleotides in length, yet more preferably at least about 160 nucleotides in length, yet more preferably at least about 170 nucleotides in length, yet more preferably at least about 180 nucleotides in length, yet more preferably at least about 190 nucleotides in length, yet more preferably at least about 200 nucleotides in length, yet more preferably at least about 250 nucleotides in length, yet more preferably at least about 300 nucleotides in length, yet more preferably at least about 350 nucleotides in length, yet more preferably at least about 400 nucleotides in length, yet more preferably at least about 450 nucleotides in length, yet more preferably at least about 500 nucleotides in length, yet more preferably at least about 600 nucleotides in length, yet more preferably at least about 700 nucleotides in length, yet more preferably at least about 800 nucleotides in length, yet more preferably at least about 900 nucleotides in length, yet more preferably at least about 100 nucleotides in length, wherein in this context "about" means the referenced nucleotide sequence length plus or minus 10% of that referenced length. In a preferred embodiment, the nucleotide sequence fragment is derived from any coding region of the nucleotide sequence shown in SEQ ID NO:2 or SEQ ID NO:4. In a more preferred embodiment, the nucleotide sequence fragment is derived from nucleotides about 50 to about 390 and about 621 through about 640, inclusive, of SEQ ID NO:4. Alternatively, the nucleotide sequence fragment can be derived from a fragment within the region between 391 and 620, inclusive, provided at least one nucleotide is included outside of the region (i.e., 50-390, 621-640).

In another embodiment, the invention provides a vector comprising DNA encoding a PRO1031 or PRO1122 or its variants. The vector may comprise any of the isolated nucleic acid molecules hereinabove defined.

In another embodiment, the invention provides a host cell comprising the above vector. By way of example, the host cells may be CHO cells, *E. coli*, or yeast. A process for producing PRO1031 or PRO1122 polypeptides is further provided and comprises culturing host cells under conditions suitable for expression of PRO1031 or PRO1122, respectively, and recovering PRO1031 or PRO1122, respectively, from the cell culture.

In another embodiment, the invention provides isolated PRO1031 or PRO1122 polypeptides encoded by any of the isolated nucleic acid sequences hereinabove defined.

In another aspect, the invention concerns an isolated PRO1031 or PRO1122 polypeptide, comprising an amino acid sequence having at least about 80% sequence identity, preferably at least about 81% sequence identity, more preferably about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to the sequence of amino acid residues about (a) 1 or about 21 to about 180, inclusive, of SEQ ID NO:1, or (b) 1 or about 19 to about 197, inclusive, of SEQ ID NO:3, respectively. In a preferred aspect, the polypeptide comprises amino acid residues about (a) 1 or about 21 to about 180, inclusive, of SEQ ID NO:1 or (b) 1 or about 19 to about 197, inclusive, of SEQ ID NO:3, respectively.

In a further aspect, the invention concerns an isolated PRO1031 or PRO1122 polypeptide comprising an amino acid sequence having at least about 80% sequence identity, preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity, yet more preferably at least about 99% sequence identity to the amino acid encoded by the human protein cDNA deposited with the ATCC on (1) 14 May 1999 under ATCC Deposit No. 209866 (DNA59294-1381) or (2) 22 Dec. 1998 under ATCC Deposit No. 203552, respectively.

In a preferred embodiment, the PRO1031 or PRO1122 polypeptide is obtained or obtainable by expressing the polypeptide encoded by the cDNA insert of the vector deposited on (a) 14 May 1998 under ATCC deposit number 209866 (DNA59294-1381), or (b) 22 Dec. 1998 under ATCC deposit number 203552 (DNA62377-1381-1).

In a further aspect, the invention concerns an isolated PRO1031 or PRO1122 polypeptide comprising an amino acid sequence scoring at least about 80% positives, preferably at least about 81% positives, more preferably at least about 82% positives, yet more preferably at least about 83% positive, yet more preferably at least about 84% positives, yet more preferably at least about 85% positives, yet more preferably at least about 86% positives, yet more preferably at least about 87% positives, yet more preferably at least about 88% positives, yet more preferably at least about 89% positives, yet more preferably at least about 90% positives, yet more preferably at least about 91% positives, yet more preferably at least about 92% positives, yet more preferably at least about 93% positives, yet more preferably at least about 94% positives, yet more preferably at least about 95% positives, yet more preferably at least about 96% positives, yet more preferably at least about 97% positives, yet more preferably at least about 98% positives, yet more preferably at least about 99% positives, when compared with the amino acid sequence of residues from about (1) 1 or about 21 to about 180, inclusive, of SEQ ID NO:1, or (2) 1 or about 19 to about 197, inclusive, of SEQ ID NO:3.

In a specific aspect, the invention provides an isolated PRO1031 or PRO1122 polypeptide without the N-terminal signal sequence and/or initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO1031 or PRO1122 polypeptide and recovering the PRO1031 or PRO1122 polypeptide, respectively, from the cell culture.

In still a further aspect, the invention provides a polypeptide produced by: (1) hybridizing a test DNA molecule under stringent conditions with (a) a DNA molecule encoding a (i) PRO1031 polypeptide having the sequence of amino acid residues from about 21 to about 180, inclusive, of SEQ ID NO:1, or (ii) PRO1122 polypeptide having the sequence of amino acid residues from about 19 to about 197, inclusive, of SEQ ID NO:3, or (b) the complement of the DNA molecule of (a); and if the test DNA molecule has at least about an 80% sequence identity, preferably at least about an 81% sequence identity, more preferably at least about an 82% sequence identity, yet more preferably at least about an 83% sequence identity, yet more preferably at least about an 84% sequence identity, yet more preferably at least about an 85% sequence identity, yet more preferably at least about an 86% sequence identity, yet more preferably at least about an 87% sequence identity, yet more preferably at least about an 88% sequence identity, yet more preferably at least about an 89% sequence identity, yet more preferably at least about a 90% sequence identity, yet more preferably at least about a 91% sequence identity, yet more preferably at least about a 92% sequence identity, yet more preferably at least about a 93% sequence identity, yet more preferably at least about a 94% sequence identity, yet more preferably at least about a 95% sequence identity, yet more preferably at least about a 96% sequence identity, yet more preferably at least about a 97% sequence identity, yet more preferably at least about 98% sequence identity, yet more preferably at least about a 99% sequence identity to (a) or (b); (2) culturing a host cell comprising the test DNA molecule under conditions suitable for expression of the polypeptide, and (3) recovering the polypeptide from the cell culture.

In yet another aspect, the invention concerns an isolated PRO1031 or PRO1122 polypeptide comprising the sequence of amino acid residues from about (1) 1 or about 21 to about 180, inclusive, of SEQ ID NO:1, or (2) 1 or about 19 to about 197, inclusive, of SEQ ID NO:3, respectively, or a fragment thereof which is biologically active or sufficient to provide a binding site for an anti-PRO1031 or anti-PRO1122 antibody, respectively, wherein the identification of PRO1031 or PRO1122 polypeptide fragments, respectively, that possess biological activity or provide a binding site for an anti-PRO1031 or anti-PRO1122 antibody, respectively, may be accomplished in a routine manner using techniques which are well known in the art.

In another embodiment, the invention provides chimeric molecules comprising a PRO1031 or PRO1122 polypeptide fused to a heterologous polypeptide or amino acid sequence. An example of such a chimeric molecule comprises a PRO1031 or PRO1122 polypeptide, respectively, fused to an epitope tag sequence or a Fc region of an immunoglobulin.

In another embodiment, the invention provides an antibody which specifically binds to a PRO1031 or PRO1122 polypeptide. Optionally, the antibody is a monoclonal antibody, an antibody fragment or a single chain antibody.

In yet another embodiment, the invention concerns agonists and antagonists of a native PRO1031 or PRO1122 polypeptide. In a particular aspect, the agonist or antagonist is an anti-PRO1031 or anti-PRO1122 antibody, or a small molecule.

In yet another embodiment, the invention concerns a method of identifying agonists or antagonists of a native PRO1031 or native PRO1122 polypeptide, by contacting the native PRO1031 or PRO1122 polypeptide with a candidate molecule and monitoring a biological activity mediated by said polypeptide.

In still a further embodiment, the invention concerns a composition comprising a PRO1031 or PRO1122 polypeptide, or an agonist or antagonist as hereinabove defined, in combination with a carrier. Preferably, the carrier is pharmaceutically acceptable.

In still a further embodiment, the invention concerns the use of a PRO1031 or PRO1122 polypeptide, or an agonist or antagonist thereof as hereinbefore described, or an anti-PRO1031 or anti-PRO1122 antibody, for the preparation of a medicament useful in the treatment of a condition which is responsive to the PRO1031 or PRO1122 polypeptide or an agonist or antagonist thereof (e.g., anti-PRO1031 or PRO1122). In a particular aspect, the invention concerns the use of a PRO1031 or PRO1122 polypeptide, or an agonist or antagonist thereof in a method for treating a degenerative cartilaginous disorder.

In still a further embodiment, the invention relates to a method of treating a degenerative cartilaginous disorder by administration of a therapeutically effective amount of a PRO1031 or PRO122 polypeptide, agonist, or antagonist thereof to a mammal suffering from said disorder.

In still a further embodiment, the invention relates to a method of diagnosing a degenerative cartilaginous disorder by (1) culturing test cells or tissues expressing PRO1031 or PRO1122; (2) administering a compound which can inhibit PRO1031 or PRO1122 modulated signaling; and (3) measuring the PRO1031 or PRO1122 mediated phenotypic effects in the test cells.

In still a further embodiment, the invention relates to PRO1031 or PRO1122 antagonists and/or agonist molecules. In one aspect, the inventions provides a method of screening compounds which mimic PRO1031 or PRO1122 (agonists) or diminish the effect of the PRO1031 or PRO1122 (antagonists).

In still a further embodiment, the invention relates to a therapeutic composition comprising a therapeutically effective amount of PRO1031, PRO1122, antagonist or agonist thereof in combination with a pharmaceutically-acceptable carrier.

In still a further embodiment, the invention relates to an article of manufacture comprising a container, label and therapeutically effective amount of PRO1031, PRO1122, antagonist or agonist thereof in combination with a pharmaceutically-acceptable carrier.

BRIEF DESCRIPTION OF THE DRAWINGS

FIG. 1A shows an alignment between the protein sequences encoded by DNA59624 (IL17-B) (SEQ ID NO:1), DNA62377 (IL17-C) (SEQ ID NO:3) and IL-17 (SEQ ID NO:11). The putative signal sequences are underlined, potential N-linked glycosylation sites are double underlined, and conserved tryptophan and cysteine residues are marked with asterisks. L-17, IL-17B and IL-17C share 26-28% amino acid identity with each other.

FIG. 1B shows an alignment between just the encoded protein from DNA59624 (SEQ ID NO:1) and DNA62377 (SEQ ID NO:3).

FIGS. 3A-3B depict bar graphs representing the biological activities of IL17 (SEQ ID NO:11), IL17B (UNQ516) (SEQ ID NO:1) and IL17C (UNQ561) (SEQ ID NO:3). FIG. 3A shows human foreskin fibroblast (HFF) cells cultured with control Fc fusion protein, IL-17, IL-17B.Fc (SEQ ID NO:12) or IL-17C.Fc (SEQ ID NO:13) at 100 ng/ml for 18 hours and the conditioned media were assayed for IL-6 (SEQ ID NO:14) as described in Example 11. FIG. 3B shows the human leukemic cell line, THP1, which was treated with the same cytokines (100 ng/ml) as above under the same conditions wherein the supernatants were assayed for the level of TNF-α release. Results are expressed as the mean+/−SE of triplicate determinations from one representative experiment.

In FIG. 4A, THP1 cells were incubated with 100 ng/ml (2.2 nM) of IL17B.Fc (SEQ ID NO:12) or IL17C.Fc (SEQ ID NO:13) for 0.5 to 32 hours, the conditioned media harvested, and the TNF-α concentration quantitated as described in Example 11. In FIG. 4B, THP1 cells were treated with the IL-17B.Fc and IL-17C.Fc at a concentration range from 0 to 120 nM for 18 hours and the TNF-α release determined.

In FIG. 5A, IL-17 (SEQ ID NO:11), IL-17B.Fc (SEQ ID NO:12) and IL-17C.Fc (SEQ ID NO:13), or control Fc fusion proteins were incubated with the supernatant and protein-A-agarose beads were added to precipitate the Fc fusion proteins. For the IL-17 immunoprecipitation reaction, anti-IL-17 antibodies were included. FIG. 5B shows the results of a competitive binding experiment, wherein immunoprecipitation of IL-17R ECD (SEQ ID NO:22) by IL-17 (SEQ ID NO:11) was performed in the presence of a five-fold excess of IL-17B.his (SEQ ID NO:23) and control his-tagged proteins. Precipitates in both FIG. 5A and FIG. 5B were analyzed by electrophoresis on NuPAGE (4-12% Bis-Tris) gels. Molecular weight markers are indicated on the left of each panel.

FIG. 9 shows the effect of NO on IL-17 induced changes in matrix metabolism. Explants were treated with IL-17 (5 ng/ml) (SEQ ID NO:11) alone (+) or with an irreversible inhibitor of nitric oxide synthase, NOS (L-NIO, Caymen Chemical, 0.5 mM). After 72 hours of treatment, media was assayed for (A) nitrite and (B) proteoglycans (PGs). (C) Proteoglycan synthesis was determined by incorporation of $^{35}$S-sulphate into the tissue.

DETAILED DESCRIPTION OF THE PREFERRED EMBODIMENTS

I. Definitions

Figure 2:
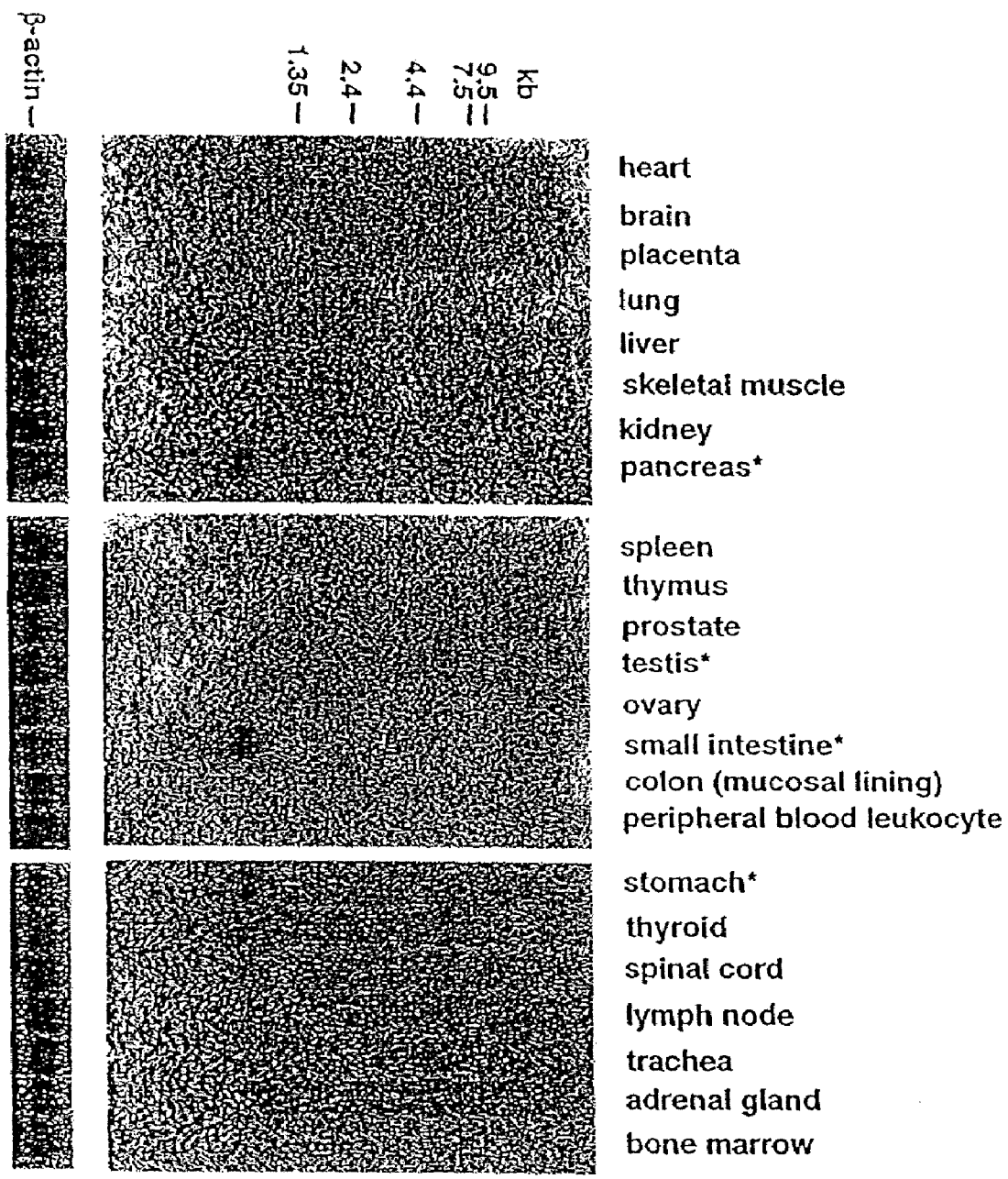
FIG. 2 is an RNA blot analysis of IL-17B (UNQ516) (SEQ ID NO:1). The northern blot depicts mRNA from human tissues (Clontech) hybridized to a human IL17B specific radiolabeled probe as described in Example 9. RNA size markers are shown on the left. A rehybridization of the same blot with a human β3-actin cDNA probe is shown at the bottom.

The terms "PRO1031 polypeptide", or "PRO1122 polypeptide" and "PRO1031", or "PRO1122" when used herein encompass native sequence PRO1031, native sequence PRO1122, respectively and polypeptide variants thereof (which are further defined herein). The PRO1031 or PRO1122 polypeptides may be isolated from a variety of sources, such as from human tissue types or from another source, or prepared by recombinant or synthetic methods.

A "native sequence PRO1031 polypeptide" or "native sequence PRO1122 polypeptide" comprise a polypeptide having the same amino acid sequence as a PRO1031 or PRO1122 polypeptide, respectively, derived from nature. Such native sequence PRO1031 or PRO1122 polypeptide can be isolated from nature or can be produced by recombinant or synthetic means. The term "native sequence PRO1031 polypeptide" or "native sequence PRO1122 polypeptide" specifically encompasses naturally-occurring truncated or secreted forms of a PRO1031 polypeptide or PRO1122 polypeptide, respectively, (e.g., soluble forms containing for instance, an extracellular domain sequence), naturally-occurring variant forms (e.g., alternatively spliced forms) and naturally-occurring allelic variants of a PRO1031 or PRO1122 polypeptide, respectively.

In one embodiment of the invention, the native sequence PRO1031 polypeptide or PRO1122 polypeptide is a full-length or mature native sequence (a) PRO1031 polypeptide comprising amino acids 1 or 21 through 180 of SEQ ID NO:1 or (b) PRO1122 polypeptide comprising amino acids 1 or 19 through 197 of SEQ ID NO:3, respectively. Also, while the PRO1031 or PRO1122 polypeptides disclosed in SEQ ID NO: 1 and SEQ ID NO:3, respectively, (i.e., UNQ516 and UNQ561), are shown to begin with a methionine residue designated as amino acid position 1, it is conceivable and possible that another methionine residue located either upstream or downstream from amino acid position 1 in SEQ ID NO:1 or SEQ ID NO:3 may be employed as the starting amino acid residue.

The term "UNQ516" or "UNQ561" refer to the specific native sequence PRO1031 or PRO1122 protein, respectively, depicted in SEQ ID NO:1 or SEQ ID NO:3, respectively. Optionally, the PRO1031 or PRO1122 polypeptide is obtained or obtainable by expressing the polypeptide encoded by the cDNA insert of the vector DNA59294-1381 or DNA62377-1381-1, under ATCC deposit number 209866 or 203552, respectively.

"PRO1031 variant" or "PRO1122 variant" means an "active" PRO1031 polypeptide or PRO1122 polypeptide, respectively, as defined below having at least about 80% amino acid sequence identity with the PRO1031 polypeptide or PRO1122 polypeptide, respectively, having the deduced amino acid sequence of residues (1) 1 or about 21 to about 180 shown in SEQ ID NO:1, or (2) 1 or about 19 to 197 shown in SEQ ID NO:3, respectively, for a full-length or mature native sequence PRO1031 or PRO1122 polypeptide, respectively. Such PRO1031 or PRO1122 polypeptide variants include, for instance, PRO1031 polypeptides or PRO1122 polypeptides, respectively, wherein one or more amino acid residues are added, substituted or deleted, at the N- or C-terminus or within the sequence of SEQ ID NO:1 or SEQ ID NO:3, respectively. Ordinarily, a PRO1031 or PRO1122 polypeptide variant will have at least about 80% amino acid sequence identity, preferably at least about 81% amino acid sequence identity, more preferably at least about 82% amino acid sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 96% sequence identity, yet more preferably at least about 97% sequence identity, yet more preferably at least about 98% sequence identity, yet more preferably at least about 99% amino acid sequence identity with the amino acid sequence of SEQ ID NO:1 or SEQ ID NO:3, with or without the signal peptide (E.g., with signal peptide amino acid residues 1 to 180 of SEQ ID NO:1, 1 to 197 of SEQ ID NO:3, without signal peptide about 21 to 180 of SEQ ID NO:1, about 19 to 197 of SEQ ID NO:3). The variants provided herein exclude native sequence PRO1031 and PRO1122 sequences as well the polypeptides and nucleic acids described herein with which the PRO1031 and PRO1122 polypeptides share 100% identity and/or which are already known in the art.

"Percent (%) amino acid sequence identity" with respect to the PRO1031 amino acid sequences identified herein is defined as the percentage of amino acid residues in a candidate sequence that are identical with the amino acid residues in a PRO1031 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software. Those skilled in the art can determine appropriate parameters for measuring alignment, including any algorithms needed to achieve maximal alignment over the full length of the sequences being compared. For example, the % identity values used herein are generated using WU-BLAST-2 (Altschul et al., *Methods in Enzymology* 266: 460-480 (1996). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM 62. For purposes herein, a % amino acid sequence identity value is determined by divided (a) the number of matching identical amino acid residues between the amino acid sequence of the PRO1031 or PRO1122 polypeptide of interest and the comparison amino acid sequence of interest (i.e., the sequence against which the PRO1031 or PRO1122 polypeptide of interest is being compared) as determined by WU-BLAST-2 by (b) the total number of amino acid residues of the PRO1031 or PRO1122 polypeptide of interest, respectively.

A "PRO1031 or PRO1122 variant polynucleotide" or PRO1031 or PRO1122 variant nucleic acid sequence" means an active PRO1031 or PRO1122 polypeptide-encoding nucleic acid molecule as defined below having at least about 65% nucleic acid sequence identity with the nucleotide acid sequence of nucleotides: (1) about 42 or about 102 to about 589 or about 687 of the PRO1031-encoding nucleotide sequence shown in SEQ ID NO:2; or (2) about 59 or about 104 to about 640 or about 1043 of the PRO1122-encoding nucleotide sequence shown in SEQ ID NO:4, respectively. Ordinarily, a PRO1031 or PRO1122 polypeptide will have at least about 65% nucleic acid sequence identity, more preferably at least about 70% nucleic acid sequence identity, yet more preferably at least about 75% nucleic acid sequence identity, yet more preferably at least about 80% nucleic acid sequence identity, yet more preferably at least about 81% nucleic acid sequence identity, yet more preferably at least about 82% nucleic acid sequence identity, yet more preferably at least about 83% nucleic acid sequence identity, yet more preferably at least about 84% nucleic acid sequence identity, yet more preferably at least about 85% nucleic acid sequence identity, yet more preferably at least about 86% nucleic acid sequence identity, yet more preferably at least about 87% nucleic acid sequence identity, yet more preferably at least about 88% nucleic acid sequence identity, yet more preferably at least about 89% nucleic acid sequence identity, yet more preferably at least about 90% nucleic acid sequence identity, yet more preferably at least about 91% nucleic acid sequence identity, yet more preferably at least about 92% nucleic acid sequence identity, yet more preferably at least about 93% nucleic acid sequence identity, yet more preferably at least about 94% nucleic acid sequence identity, yet more preferably at least about 95% nucleic acid sequence identity, yet more preferably at least about 96% nucleic acid sequence identity, yet more preferably at least about 97% nucleic acid sequence identity, yet more preferably at least about 98% nucleic acid sequence identity, yet more preferably at least about 99% nucleic acid sequence identity with the nucleic acid sequence of nucleotides: 1) about 42 or about 102 to about 589 of the PRO1031-encoding nucleotide sequence shown in SEQ ID NO:2; or (2) about 59 or about 104 to about 640 of the PRO1122-encoding nucleotide sequence shown in SEQ ID NO:4, respectively. Variants specifically exclude or do not encompass the native nucleotide sequence, as well as those prior art sequences which share 100% identity with the nucleotide sequences of the invention.

"Percent (%) nucleic acid sequence identity" with respect to the PRO1031 or PRO1122 sequences identified herein is defined as the percentage of nucleotides in a candidate sequence that are identical with the nucleotides in the PRO1031 sequence or PRO1122 sequence, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as ALIGN, Align-2, Megalign (DNASTAR), or BLAST (e.g., Blast, Blast-2) software. Those skilled in the art can determine appropriate parameters for measuring alignment, including any algorithms needed to achieve maximal alignment over the full length of the sequences being compared. For purposes herein, however, % nucleic acid identity values are generated using the WU-BLAST-2 (BlastN module) computer program (Altschul et al., *Methods in Enzymology* 266: 460-480 (1996). Most of the WU-BLAST-2 search parameters are set to the default values. Those not set default values, i.e., the adjustable parameters, are set with the following values: overlap span=1, overlap fraction=0.125, word threshold (T)=11 and scoring matrix=BLOSUM62. For purposes herein, a % nucleic acid sequence identity value is determined by dividing (a) the number of matching identical nucleotides between the nucleic acid sequence of the PRO polypeptide-encoding nucleic acid molecule of interest and the comparison nucleic acid molecule of interest (i.e., the sequence against which the PRO polypeptide-encoding nucleic acid molecule of interest is being compared) as determined by WU-BLAST-2 by (b) the total number of nucleotides of the PRO polypeptide-encoding nucleic acid molecule of interest.

In other embodiments, the PRO1031 or PRO1122 variant polypeptides are nucleic acid molecules that encode an active PRO1031 or PRO1122 polypeptide and which are capable of hybridizing, preferably under stringent hybridization and wash conditions, to nucleotide sequences encoding the full-length PRO1031 or PRO1122 polypeptide shown in SEQ ID NO:2 or SEQ ID NO:4, respectively. This scope of variant polynucleotides specifically excludes those sequences which are known as of the filing and/or priority dates of the present application. Furthermore, PRO1031 or PRO1122 variant polypeptides may also be those that are encoded by a PRO1031 or PRO1122 variant polynucleotide, respectively.

The term "positives", in the context of sequence comparison performed as described above, includes residues in the sequences compared that are not identical but have similar properties (e.g., as a result of conservative substitutions). The % identity value of positives is determined by the fraction of residues scoring a positive value in the BLOSUM 62 matrix. This value is determined by dividing (a) the number of amino acid residues scoring a positive value in the BLOSUM62 matrix of WU-BLAST-2 between the PRO1031 or PRO1122 polypeptide amino acid sequence of interest and the comparison amino acid sequence (i.e., the amino acid sequence against which the PRO1031 or PRO1122 polypeptide sequence is being compared) as determined by WU-BLAST-2 by (b) the total number of amino acid residues of the PRO1031 or PRO1122 polypeptide of interest.

"Isolated," when used to describe the various polypeptides disclosed herein, means polypeptide that has been identified and separated and/or recovered from a component of its natural environment. Preferably, the isolated polypeptide is free of association with all components with which it is naturally associated. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO1031 or PRO1122 polypeptide natural environment will not be present. Ordinarily, however, isolated polypeptide will be prepared by at least one purification step.

An "isolated" PRO1031 or PRO1122 polypeptide-encoding nucleic acid molecule is a nucleic acid molecule that is identified and separated from at least one contaminant nucleic acid molecule with which it is ordinarily associated in the natural source of the PRO1031 polypeptide- or PRO1122 polypeptide-encoding nucleic acid. An isolated PRO1031 polypeptide- or PRO1122 polypeptide-encoding nucleic acid molecule is other than in the form or setting in which it is found in nature. Isolated PRO1031 polypeptide- or PRO1122 polypeptide-encoding nucleic acid molecules therefore are distinguished from the PRO1031 polypeptide- or PRO1122 polypeptide-, respectively, encoding nucleic acid molecule as it exists in natural cells. However, an isolated PRO1031 polypeptide- or PRO1122 polypeptide-encoding nucleic acid molecule includes PRO1031 polypeptide- or PRO1122 polypeptide-, respectively, encoding nucleic acid molecules contained in cells that ordinarily express PRO1031 polypeptide or PRO1122 polypeptide, where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes required higher temperatures for proper annealing, while short probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reactions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that" (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" where used herein refers to a chimeric polypeptide comprising a PRO1031 or PRO1122 polypeptide, or domain sequence thereof, fused to a "tag polypeptide". The tag polypeptide has enough residues to provide an epitope against which an antibody may be made, or which can be identified by some other agent, yet is short enough such that it does not interfere with the activity of the PRO1031 or PRO1122 polypeptide. The tag polypeptide preferably is also fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3 or IgG-4 subtypes, IgA (including IgG-1 and IgA-2), IgE, IgD or IgM.

The term "antibody" is used in the broadest sense and specifically covers single anti-PRO1031 or anti-PRO1122 polypeptide monoclonal antibodies (including agonist, antagonist, and neutralizing antibodies), anti-PRO1031 or anti-PRO1122, respectively, antibody compositions with polyepitopic specificity, single-chain anti-PRO1031 or anti-PRO1122 antibodies, and fragments of anti-PRO1031 or anti-PRO1122 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of PRO1031 or PRO1122 which retain the biologic and/or immunologic activities of native or naturally-occurring PRO1031 or PRO1122, respectively, polypeptide. Elaborating further, "biological" activity refers to a biological function (either inhibitory or stimulatory) caused by a native or naturally-occurring PRO1031 or PRO1122 other than the ability to induce the production of an antibody against an antigenic epitope possessed by a native or naturally-occurring PRO1031 or PRO1122 and an "immunological" activity refers only to the ability to induce the production of an antibody against an antigenic epitope possessed by a native or naturally-occurring PRO1031 or PRO1122. A preferred biological activity includes, for example, the release of TNF-α from THP1 cells. An alternative activity is the reduction in IL-1α induced NO (nitric oxide) production from articular cartilage.

"Degenerative cartilagenous disorder" describes a host of disorders that is characterized principally by the destruction of the cartilage matrix. Additional pathologies includes nitric oxide production, and elevated proteoglycan breakdown. Exemplary disorders encompassed within this definition, include, for example, arthritis (e.g., osteoarthritis, rheumatoid arthritis, psoriatic arthritis), sepsis, ulcerative colitis, psoriasis, multiple sclerosis, type I diabetes, giant cell arthritis, systemic lupus erythematosus and Sjögren's syndrome.

The term "antagonist" is used in the broadest sense, and includes any molecule that partially or fully blocks, inhibits, or neutralizes a biological activity of a native PRO1031 or PRO1122 polypeptide disclosed herein. In a similar manner, the term "agonist" is used in the broadest sense and includes any molecule that mimics a biological activity of a native PRO1031 or PRO1122 polypeptide disclosed herein. Suitable agonist or antagonist molecules specifically include agonist or antagonist antibodies or antibody fragments, fragments or amino acid sequence variants of native PRO1031 or PRO1122 polypeptides, peptides, small organic molecules, etc. Method for identifying agonists or antagonists of a PRO1031 or PRO1122 polypeptide may comprise contacting a PRO1031 or PRO1122 polypeptide with a candidate agonist or antagonist molecule and measuring a detectable change in one or more biological activities normally associated with the PRO1031 or PRO1122 polypeptide.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

The terms "treating", "treatment" and "therapy" as used herein refer to curative therapy, prophylactic therapy, and preventative therapy. An example of "preventative therapy" is the prevention or lessened targeted pathological condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

The term "mammal" as used herein refers to any mammal classified as a mammal, including humans, domestic and farm animals, and zoo, sports or pet animals, such as cattle (e.g. cows), horses, dogs, sheep, pigs, rabbits, goats, cats, etc. In a preferred embodiment of the invention, the mammal is a human.

Administration "in combination with" one or more further therapeutic agents includes simultaneous (concurrent) and consecutive administration in any order.

A "therapeutically-effective amount" is the minimal amount of active agent (e.g., PRO1031, PRO1122, antagonist or agonist thereof) which is necessary to impart therapeutic benefit to a mammal. For example a "therapeutically-effective amount" to a mammal suffering or prone to suffering or to prevent it from suffering from a degenerative cartilagenous disorder is such an amount which induces, ameliorates or otherwise causes an improvement in the pathological symptoms, disease progression, physiological conditions associated with or resistance to succumbing to a disorder principally characterized by the destruction of the cartilage matrix.

"Carriers" as used herein include pharmaceutically-acceptable carriers, excipients, or stabilizers which are nontoxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecule weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$ and Fv fragments; diabodies; linear antibodies (Zapata et al., *Protein Engin.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDR specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fv fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domain which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097, WO 93/11161; and Hollinger et al., Proc. Natl. Acad. Sci. USA 90: 6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alternation of a substrate compound or composition which is detectable.

"Solid phase" is meant to be a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromotagraphy column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO1031 or PRO1122 polypeptide or antibody thereto) to a mammal. The components of the liposome are commonly arranged in a bilayer formation, similar to the lipid arrangement of biological membranes.

A "small molecule" is defined herein to have a molecule weight below about 500 Daltons.

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

II. Compositions and Methods of the Invention

A. Full-length PRO1031 or PRO1122 Polypeptide

The present invention provides newly identified and isolated nucleotide sequences encoding polypeptides referred to in the present application as PRO1031 or PRO1122. In particular, Applicants have identified and isolated cDNA encoding a PRO1031 (e.g., UNQ516, IL-17B, SEQ ID NO:1) and PRO1122 (e.g., UNQ561, IL-17C, SEQ ID NO:3) polypeptide, as disclosed in further detail in the Examples below. Using BLAST and FastA sequence alignment computer programs, Applicants found that various portions of the PRO1031 and PRO1122 polypeptide have sequence identity with IL-17. Accordingly, it is presently believed that PRO1031 and PRO1122 polypeptide disclosed in the present application are newly identified members of the cytokine family and thus may be involved in inflammation and/or the immune system function.

As presented earlier, the term "PRO1031" or "PRO1122" refers to the native sequence and variants, whereas the terms "UNQ516" or "UNQ561" refer to the specific amino acid sequences of SEQ ID NO:1 and SEQ ID NO:3, respectively, and/or the proteins encoded by the cDNA deposited with the American Type Culture Collection, under Deposit numbers 209866 and 203552, respectively.

As disclosed in the Examples below, cDNA clone designated herein as DNA59294-1381 and DNA62377-1381-1 have been deposited with the ATCC. The actual nucleotide sequence of the clone can be readily determined by the skilled artisan by sequencing of the deposited clone using routine methods in the art. The predicted amino acid sequence can be determined from the nucleotide sequence using routine skill. For the PRO1031 or PRO1122 polypeptide and encoding nucleic acid described herein, Applicants have identified what is believed to be the reading frame best identifiable with the sequence information available at the time.

B. PRO1031 and PRO1122 Variants

In addition to the full-length native sequence PRO1031 or PRO1122 polypeptide described herein, it is contemplated that PRO1031 or PRO1122 variants can be prepared. PRO1031 or PRO1122 variants can be prepared by introducing appropriate nucleotide changes into the PRO1031- or PRO1122-encoding DNA, or by synthesis of the desired PRO1031 or PRO1122 polypeptide. Those skilled in the art will appreciate that amino acid changes may alter post-translational processes of the PRO1031 or PRO1122 polypeptide, such as changing the number or position of glycosylation sites or altering the membrane anchoring characteristics.

Variations in the native full-length sequence PRO1031 or PRO1122 or in various domains of the PRO1031 or PRO1122 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO1031 or PRO1122 polypeptide that results in a change in the amino acid sequence of the PRO1031 or PRO1122 polypeptide as compared with the native sequence PRO1031 or PRO1122. Optionally the variation is by substitution of at least one amino acid with any other amino acid in one or more of the domains of the PRO1031 or PRO1122 polypeptide. Guidance in determining which amino acid residue may be inserted, substituted or deleted without adversely affecting the desired activity may be found by comparing the sequence of the PRO1031 or PRO1122 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity (such as in any of the in vitro assays described in the Examples below) for activity exhibited by the full-length or mature native sequence.

PRO1031 or PRO1122 polypeptide fragments are provided herein. Such fragments may be truncated at the N-terminus or C-terminus, or may lack internal residues, for example, when compared with a full length or native protein. Certain fragments lack amino acid residues that are not essential for a desired biological activity of the PRO1031 or PRO1122 polypeptide.

PRO1031 or PRO1122 fragments may be prepared by any of a number of conventional techniques. Desired peptide fragments may be chemically synthesized. An alternative approach involves generating PRO1031 or PRO1122 fragments by enzymatic digestion, e.g., by treating the protein with an enzyme known to cleave proteins at sites defined by particular amino aid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO1031 or PRO1122 polypeptide fragments share at least one biological and/or immunological activity with the native PRO1031 or PRO1122 polypeptide shown in SEQ ID NO: 1 or SEQ ID NO:3.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

Conservative Substitutions

| Original residue | Example substitutions | Preferred substitutions |
| --- | --- | --- |
| Ala (A) | val, leu, ile | val |
| Arg (R) | lys, gln, asn | lys |
| Asn (N) | gln, his, lys, arg | gln |
| Asp (D) | glu | glu |
| Cys (C) | ser | ser |
| Gln (Q) | asn | asn |
| Glu (E) | asp | asp |
| Gly (G) | pro, ala | ala |
| His (H) | asn, gln, lys, arg | arg |
| Ile (I) | leu, val, met, ala, phe, norleucine | leu |
| Leu (L) | norleucine, ile, val, met, ala, phe | ile |
| Lys (K) | arg, gln, asn | arg |
| Met (M) | leu, phe, ile | leu |
| Phe (F) | leu, val, ile, ala, tyr | leu |
| Pro (P) | ala | ala |
| Ser (S) | thr | thr |
| Thr (T) | ser | ser |
| Trp (W) | tyr, phe | tyr |
| Tyr (Y) | trp, phe, thr, ser | phe |
| Val (V) | ile, leu, met, phe, ala, norleucine | leu |

Substantial modifications in function or immunological identity of the PRO1031 or PRO1122 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: sys, ser, thr;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites, or more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the PRO1031-encoding variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of PRO1031 or PRO1122

Covalent modifications of PRO1031 or PRO1122 polypeptides are included within the scope of this invention. One type of covalent modification includes reacting targeted amino acid residues of a PRO1031 or PRO1122 polypeptide with an organic derivatizing agent that is capable of reacting with selected side chains or the N- or C-terminal residues of a PRO1031 or PRO1122 polypeptide. Derivatization with bifunctional agents is useful, for instance, for crosslinking PRO1031 or PRO1122 to a water-insoluble support matrix or surface for use in the method for purifying anti-PRO1031 or PRO1122 antibodies, and vice-versa. Commonly used crosslinking agents include, e.g., 1,1-bis(diazo-acetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis-(succinimidylproprionate), bifunctional maleimides such as bis-N-maleimido-1,8-octane and agents such as methyl-3-[(p-azidophenyl)-dithio]proprioimidate. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO1031 or PRO1122 polypeptide included within the scope of this invention comprises altering the native glycosylation pattern of the polypeptide. "Altering the native glycosylation pattern" is intended for purposes herein to mean deleting one or more carbohydrate moieties found in native sequence PRO1031 or PRO1122 polypeptide, and/or adding one or more glycosylation sites that are not present in the native sequence PRO1031 or PRO1122 polypeptide. Additionally, the phrase includes qualitative changes in the glycosylation of the native proteins, involving a change in the nature and proportions of the various carbohydrate moieties present.

Addition of glycosylation sites to PRO1031 or PRO1122 polypeptides may be accomplished by altering the amino acid sequence thereof. The alteration may be made, for example, by the addition of, or substitution by, one or more serine or threonine residues to the native sequence PRO1031 or PRO1122 polypeptide (for O-linked glycosylation sites). The PRO1031 or PRO1122 amino acid sequence may optionally be altered through changes at the DNA level, particularly by mutating the DNA encoding the PRO1031 or PRO1122 polypeptide at preselected bases such that codons are generated that will translate into the desired amino acids.

Another means of increasing the number of carbohydrate moieties on the PRO1031 or PRO1122 polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the PRO1031 or PRO1122 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO1031 or PRO1122 comprises linking the PRO1031 or PRO1122 polypeptide, respectively, to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791, 192 or 4,179,337.

PRO1031 or PRO1122 polypeptides of the present invention may also be modified in a way to form chimeric molecules comprising a PRO1031 or PRO1122 polypeptide, respectively, fused to another, heterologous polypeptide or amino acid sequence. In one embodiment, such a chimeric molecule comprises a fusion of a PRO1031 or PRO1122 polypeptide with a tag polypeptide which provides an epitope to which an anti-tag antibody can selectively bind. The epitope tag is generally placed at the amino- or carboxyl-terminus of the PRO1031 or PRO1122 polypeptide. The presence of such epitope-tagged forms of a PRO1031 or PRO1122 polypeptide can be detected using an antibody against the tag polypeptide. Also, provision of the epitope tag enables the PRO1031 or PRO1122 polypeptide to be readily purified by affinity purification using an anti-tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of a PRO1031 or PRO1122 polypeptide with an immunoglobulin or a particular region of an immunoglobulin. For a bivalent form of the chimeric molecule, such a fusion could be to the Fc region of an IgG molecule. The Ig fusions preferably include the substitution of a soluble transmembrane domain deleted or inactivated) form of a PRO1031 or PRO1122 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130, issued Jun. 27, 1995.

In yet a further embodiment, the PRO1031 or PRO1122 polypeptides of the present invention may also be modified in a way to form a chimeric molecule comprising a PRO1031 or PRO1122 polypeptide fused to a leucine zipper. Various leucine zipper polypeptides have been described in the art. See, e.g., Landschulz et al., Science 240:1759 (1988); WO 94/10308; Hoppe et al., FEBS Letters 344:1991 (1994); Maniatis et al., *Nature* 341:24 (1989). It is believed that use of a leucine zipper fused to a PRO1031 or PRO1122 polypeptide may be desirable to assist in dimerizing or trimerizing soluble PRO1031 or PRO1122 polypeptide in solution. Those skilled in the art will appreciate that the leucine zipper may be fused at either the N- or C-terminal end of the PRO1031 or PRO1122 molecule.

D. Preparation of PRO1031 or PRO122

The description below relates primarily to production of PRO1031 or PRO1122 by culturing cells transformed or transfected with a vector containing PRO1031 or PRO1122 polypeptide encoding nucleic acid. It is, of course, contemplated that alternative methods, which are well known in the art, may be employed to prepare PRO1031 or PRO1122 polypeptides. For instance, the PRO1031 or PRO1122 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of PRO1031 or PRO1122 polypeptides may be chemically synthesized separately and combined using chemical or enzymatic methods to produce a full-length PRO1031 or PRO1122 polypeptide.

1. Isolation of DNA Encoding PRO1031

DNA encoding a PRO1031 or PRO1122 polypeptide may be obtained from a cDNA library prepared from tissue believed to possess the PRO1031 or PRO1122 mRNA and to express it at a detectable level. Accordingly, human PRO1031- or PRO1122-encoding DNA can be conveniently obtained from a cDNA library prepared from human tissue, such as described in the Examples. The PRO1031- or PRO1122-encoding gene may also be obtained from a genomic library or by known synthetic procedures (e.g., automated synthetic procedures, oligonucleotide synthesis).

Libraries can be screened with probes (such as antibodies to a PRO1031 or PRO1122 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO1031 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein (e.g., through sequence alignment using computer software programs such as ALIGN, DNAstar, BLAST, BLAST-2, INHERIT and ALIGN-2 which employ various algorithms to measure homology).

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO1031 or PRO1122 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the nucleic acid (e.g., DNA) in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD266,710, published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA, ptr3 phoA E15 (argF-lac)169 degP ompT kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vivo methods of cloning, e.g., PCR or other nucleic acid polymerase reactions, are suitable.

In addition to prokaryotes, eukaryotic microbes such as filamentous fungi or yeast are suitable cloning or expression hosts for PRO1031- or PRO1122-encoding vectors. *Saccharomyces cerevisiae* is a commonly used lower eukaryotic host microorganism. Others include *Schizosaccharomyces pombe* (Beach and Nature, Nature 290: 140 [1981]; EP 139,383 published 2 May 1995); *Kluyveromyces* hosts (U.S. Pat. No. 4,943,529; Fleer et al., Bio/Technology, 2: 968-975 (1991) such as e.g., *K. lactis* (MW98-8C, CBS683, CBS4574; Louvencourt et al., J. Bacteriol. 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906); Van den Berg et al., Bio/Technology 8: 135 (1990)); *K. thermotolerans*, and *K. marxianus; yarrowia* (EP 402, 226); *Pichia pastoris* (EP 183,070); Sreekrishna et al., J. basic Microbiol. 28: 265-278 [1988]); Candid; *Trichoderma reesia* (EP 244,234); *Neurospora crassa* (Case et al., Proc. Natl. Acad. Sci. USA 76: 5359-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 19910, and *Aspergillus* hosts such as *A. nidulans* (Balance et al., Biochem. Biophys. Res. Commun. 112: 284-289 [1983]; Tilburn et al., Gene 26: 205-221; Yelton et al., Proc. Natl. Acad. Sci. USA 81: 1470-1474 [1984]) and *A. niger* (Kelly and Hynes, EMBO J. 4: 475-479 [1985]). Methylotropic yeasts are selected from the genera consisting of *Hansenula, Candida, Kloeckera, Pichia, Saccharomyces, Torulopsis*, and *Rhodotorula*. A list of specific species that are exemplary of this class of yeast may be found in C. Antony, The Biochemistry of Methylotrophs 269 (1982).

Suitable host cells for the expression of glycosylated PRO1031 or PRO1122 are derived from multicellular organisms. Examples of invertebrate cells include insect cells such as *Drosophila* S2 and *Spodoptera* Sf9, *Spodoptera* high5 as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/–DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired PRO1031 or PRO1122 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO1031 or PRO1122 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO1031- or PRO1122-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO1031- or PRO1122-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al, *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the PRO1031- or PRO1122-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding the PRO1031 or PRO1122 polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO1031 or PRO1122 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a PRO1031 or PRO1122 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO1031 or PRO1122 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO1031 or PRO1122.

Still other methods, vectors, and host cells suitable for adaptation to the synthesis of PRO1031 or PRO1122 polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO1031 or PRO1122 polypeptide or against a synthetic peptide based on the DNA sequences provided herein or against exogenous sequence fused to PRO1031- or PRO1122-encoding DNA and encoding a specific antibody epitope.

5. Purification of Polypeptide

Forms of PRO1031 or PRO1122 may be recovered from culture medium or from host cell lysates. If membrane-bound, it can be released from the membrane using a suitable detergent solution (e.g. Triton-X 100) or by enzymatic cleavage. Cells employed in expression of PRO1031 or PRO1122 polypeptides can be disrupted by various physical or chemical means, such as freeze-thaw cycling, sonication, mechanical disruption, or cell lysing agents.

It may be desired to purify PRO1031 or PRO1122 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO1031 or PRO1122 polypeptide. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular PRO1031 or PRO1122 polypeptide produced.

E. Uses for PRO1031

Nucleotide sequences (or their complement) encoding PRO1031 or PRO1122 polypeptides have various applications in the art of molecular biology, including uses as hybridization probes, in chromosome and gene mapping and in the generation of anti-sense RNA and DNA. PRO1031- or PRO1122-encoding nucleic acid will also be useful for the preparation of PRO1031 or PRO1122 polypeptides by the recombinant techniques described herein.

The full-length DNA59294-1381 nucleotide sequence (SEQ ID NO:2), full-length DNA62377-1381-1 nucleotide sequence (SEQ ID NO:4) or the full-length native sequence PRO1031 or PRO1122 nucleotide-encoding sequence, or portions thereof, may be used as hybridization probes for a cDNA library to isolate the full-length PRO1031 or PRO1122 gene or to isolate still other genes (for instance, those encoding naturally-occurring variants of PRO1031, PRO1122 or the same from other species) which have a desired sequence identity to the PRO1031 or PRO1122 nucleotide sequence disclosed in SEQ ID NO:2 or SEQ ID NO:4, respectively. Optionally, the length of the probes will be about 20 to about 50 bases. The hybridization probes may be derived from the DNA59294-1381 or DNA62377-1381-1 nucleotide sequence of SEQ ID NO:2 or SEQ ID NO:4, respectively, a or from genomic sequences including promoters, enhancer elements and introns of native sequence PRO1031- or PRO1122-encoding DNA. By way of example, a screening method will comprise isolating the coding region of the PRO1031 or PRO1122 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO1031 or PRO1122 gene of the present invention can be used to screen libraries of human cDNA, genomic DNA or mRNA to determine which members of such libraries the probe hybridizes to. Hybridization techniques are described in further detail in the Examples below.

Any EST sequence (or fragment thereof) disclosed in the present application may similarly be employed as probes, using the methods disclosed herein.

Other useful fragments of the PRO1031 or PRO1122 nucleic acids include antisense or sense oligonucleotides comprising a single-stranded nucleic acid sequence (either RNA or DNA) capable of binding to target PRO1031 or PRO1122 mRNA (sense) of PRO1031 or PRO1122 DNA (anti-sense) sequences. Antisense or sense oligonucleotides, according to the present invention, comprise a fragment of the coding region of PRO1031 or PRO1122 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen, Cancer Res. 48:2659 (1988) and van der Krol et al., *BioTechniques* 6: 958 (1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO1031 or PRO1122 proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increase affinity of the oligonucleotide for a target nucleic acid sequence, such poly-L-lysine. Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated CDT5A, DCT5B and DCT5C (see WO 90/13641).

Sense of antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The probes may also be employed in PCR techniques to generate a pool of sequences for identification of closely related PRO1031 or PRO1122 sequences.

Nucleotide sequences encoding a PRO1031 or PRO1122 polypeptide can also be used to construct hybridization probes for mapping the gene which encodes that PRO1031 or PRO1122 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO1031 or PRO1122 encode a protein which binds to another protein (example, where the PRO1031 or PRO1122 polypeptide, respectively, functions as a receptor), the PRO1031 or PRO1122 polypeptide, respectively, can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO1031 or PRO1122 polypeptide can be used to isolate correlative ligand(s). Screening assays can be designed to find lead compounds that mimic the biological activity of a native PRO1031 or PRO1122 or a receptor for PRO1031 or PRO1122, respectively. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO1031 or PRO1122 polypeptide or any of its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO1031 or PRO1122 polypeptide can be used to clone genomic DNA encoding PRO1031 or PRO1122 in accordance with established techniques and the genomic sequences used to generate transgenic animals that contain cells which express DNA encoding PRO1031 or PRO1122. Methods for generating transgenic animals, particularly animals such as mice or rats, have become conventional in the art and are described, for example, in U.S. Pat. Nos. 4,736,866 and 4,870,009. Typically, particular cells would be targeted for PRO1031 or PRO1122 transgene incorporation with tissue-specific enhancers. Transgenic animals that include a copy of a transgene encoding PRO1031 or PRO1122 introduced into the germ line of the animal at an embryonic stage can be used to examine the effect of increased expression of DNA encoding PRO1031 or PRO1122. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO1031 or PRO1122 can be used to construct a PRO1031 or PRO1122, respectively, "knock out" animal which has a defective or altered gene encoding PRO1031 or PRO1122, respectively, as a result of homologous recombination between the endogenous gene encoding PRO1031 or PRO1122, respectively, and altered genomic DNA encoding PRO1031 or PRO1122, respectively, introduced into an embryonic cell of the animal. For example, cDNA encoding PRO1031 or PRO1122, respectively, can be used to clone genomic DNA encoding PRO1031 or PRO1122, respectively, in accordance with established techniques. A portion of the genomic DNA encoding PRO1031 or PRO1122, respectively, can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PRO1031 or PRO1122 polypeptide.

Nucleic acid encoding the PRO1031 or PRO1122 polypeptides may also be used in gene therapy. In gene therapy applications, gene are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where act as inhibitors, despite their low intracellular concentrations caused by their restricted uptake by the cell membrane. Zamecnik et al., *Proc. Natl. Acad. Sci. USA* 83: 4143-4146 [1986]). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cell in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11: 205-210 [1993]). In some situations it is desirable to provide the nucleic acid source with an agent that targets the target cells, such as an antibody specific for a cell surface membrane protein or the target cell, a ligand for a receptor on the target cells, etc. Where liposomes are employed, proteins which bind to a cell surface membrane protein associated with endocytosis may by used for targeting and/or to facilitate uptake, e.g., capsid proteins or fragments thereof tropic for a particular cell type, antibodies for proteins which undergo internalization in cycling, protein that target intracellular localization and enhance intracellular half-life. The technique of receptor-mediated endocytosis is described, for example by Wu et al., *J. Biol. Chem.* 262: 4429-4432 (1987); and Wagner et al., *Proc. Natl. Acad. Sci. USA* 87: 3410-3414 (1990). For a review of gene marking and gene therapy protocols see Anderson et al., *Science* 256: 808-813 (1992).

The PRO1031 or PRO1122 polypeptides described herein may also be employed as molecular weight markers for protein electrophoresis purposes.

The nucleic acid molecule encoding the PRO1031 or PRO1122 polypeptides or fragments thereof described herein are useful for chromosome identification. In this regard, there exists an ongoing need to identity new chromosome markers, since relatively few chromosome marking reagents, based upon actual sequence data are presently available. Each PRO1031 or PRO1122 nucleic acid molecule of the present invention can be used as a chromosome marker.

The PRO1031 or PRO1122 polypeptides and nucleic acid molecules of the present invention may also be used for tissue typing, wherein the PRO1031 or PRO1122 polypeptides of the present invention may be differentially expressed in one tissue as compared to another. PRO1031 or PRO112 nucleic acid molecules will find use for generating probes for PCR, Northern analysis, Southern analysis and Western analysis.

PRO1031 or PRO1122 polypeptides of the present invention which possess biological activity related to that of IL-17 may be employed both in vivo for therapeutic purposes and in vitro. Those of ordinary skill in the art will well know how to employ the PRO1031 or PRO1122 polypeptides of the present invention for such purposes.

PRO1031 or PRO1122 can be used in assays with the polypeptides to which they have identity with to determine the relative activities. The results can be applied accordingly.

An alignment of the predicted amino acid sequence of IL-17B (e.g., UNQ516) (SEQ ID NO:1) and IL-17C (UNQ561) (SEQ ID NO:3) with the known sequence of IL-17 (SEQ ID NO:11), show that this is a family of related sequences with a 26-28% amino acid identity between the three members (FIG. 1). All three polypeptides contain a hydrophobic sequence at the N-terminus that is expected to function as a secretion signal sequence of 18-20 amino acids, giving a predicted size range for the members of this family 155 to 197 amino acids (mature MW≈17 to ≈20 kDa). The alignment of FIG. 1 shows several conserved amino acids, including a tryptophan residue and 5 cysteines in the C-terminal half of the proteins.

The PRO1031 or PRO1122 encoding nucleic acid or fragments thereof can also be used for chromosomal localizations. For example, the chromosome localization of IL-17B (UNQ516) (SEQ ID NO:1) and IL-17C (UNQ561) (SEQ ID NO:3) was determined using Taqman primers and probes designed in the 3'-untranslated regions of the IL-17B and IL-17C, was performed by PCR with Stanford Radiation Hybrid Panel G3 panel. IL-17B (UNQ516) (SEQ ID NO:1) mapped to human chromosome 5q32-34, whereas IL-17C (UNQ561) (SEQ ID NO:3) was localized to chromosome 16q24. Human IL-17 itself is found on chromosome 2q31. Rouvier et al, *M. Immunol.* 150: 5445 (1993).

The isolation and characterization of the two new relatives of IL-17, Applicants have established and expanded the potential role of this family of cytokines may play in proinflammatory immune and other responses. The three members of the family, IL-17 (SEQ ID NO:11), IL-17B (SEQ ID NO:1) and IL-17C (SEQ ID NO:3), are modestly related in primary structure with about 27% overall amino acid identity including 5 conserved cysteine residues (FIG. 1). The three family members share a number of features—they are 150-200 amino acid residues in length, they are secreted from cells via a hydrophobic secretion signal sequence, and they are expressed as disulfide-linked homodimers that in some cases appear to be glycosylated.

While members of the same gene family based on amino acid sequence similarity, the three proteins are expressed in different tissues and are dispersed in the genome. IL-17 expression (SEQ ID NO:111) has been reported only in activated T-cells, Fossiez et al., *J. Exp. Med.* 183: 2593 (1996), Yao et al., *J. Immunol.* 155: 5483 (1995)[Yao-3], while it is demonstrated herein that IL-17B (DNA59294) (SEQ ID NO:2) is expressed in normal human adult pancreas, small intestine, and stomach (FIG. 2). The expression pattern of IL-17C (DNA62377) (SEQ ID NO:4), however, is much more restricted, as confirmed expression in other tissues has not yet been discovered.

The characterizations described herein demonstrate that the biological activity of IL-17B (UNQ516) (SEQ ID NO:1) and IL-17C (UNQ561) (SEQ ID NO:3) are considerably different from the established activities for IL-17 (SEQ ID NO:11). IL-17B (UNQ516) (SEQ ID NO:1) and IL-17C (UNQ561) (SEQ ID NO:3) each fail to induce IL-6 production in human foreskin fibroblasts (Example 11) (FIG. 3A). This is in contrast to the marked induction known for IL-17 (SEQ ID NO:11). Yao et al., *Immunity* 3:811 (1995)[Yao-1], Yao et al, *J. Immunol.* 155:5483 (1995)[Yao-3]. Conversely, IL-17B (SEQ ID NO:1) and IL-17C (SEQ ID NO:3), each induce the release of TNF-α from the monocytic cell line, THP1, while IL-17 has only a very small effect (FIG. 3B). The stimulated release of TNF-α in THP1 cells by IL-17B (SEQ ID NO:1) and IL-17C (SEQ ID NO:3) is time and concentration dependent, (Example 11) (FIG. 4), with IL-17B (SEQ ID NO:1) being about 10-fold more potent than IL-17C (SEQ ID NO:3) [$EC_{50}$=2.4 nM for IL-17B vs. 25 nM for IL-17C].

Figure 5:
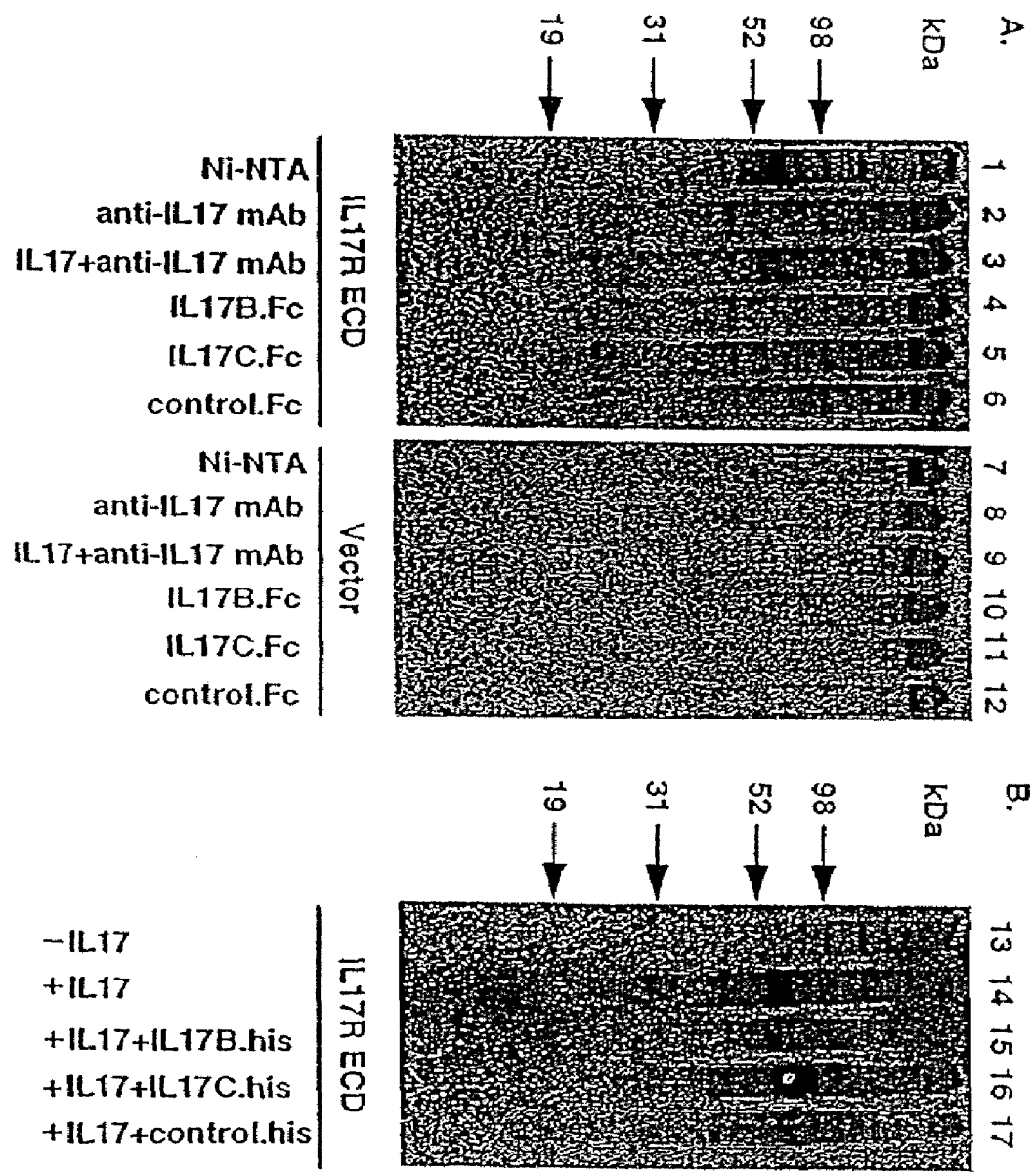
FIG. 5 is an immunoprecipitation of IL-17R ECD (SEQ ID NO:15) with IL-17 (SEQ ID NO:11), IL17B (SEQ ID NO:1) and IL-17C (SEQ ID NO:3). His-tagged IL-17 receptor ECD was expressed in 293 cells and metabolically labeled with $^{35}$S as described in Example 12. The supernatant was recovered and Ni-NTA beads were used to affinity precipitate the his-tagged IL-17R ECD (SEQ ID NO:15) in the supernatant (lane 1).
Figure 6:
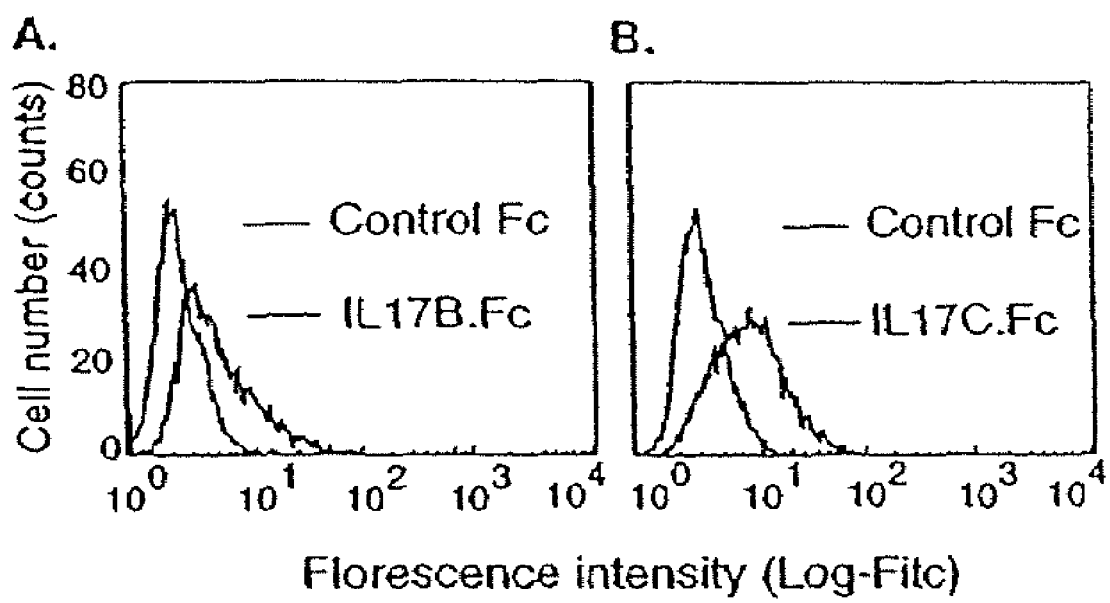
FIG. 6 shows FACS analysis of the binding of IL-17B.Fc (SEQ ID NO:12) and IL-17C.Fc (SEQ ID NO:13) to THP-1 cells. THP-1 cells were incubated with IL-17B.Fc (A) or IL-17C.Fc (B) or control Fc fusion proteins in PBS (5% horse serum) and followed by addition of FITC conjugated anti-Fc secondary antibodies.

The different biological effects of IL-17 (SEQ ID NO:11) as compared to IL-17B or C (SEQ ID NO:s 1 & 3), suggests that they may function via a different cell surface receptor (or some differing receptor components) than the known IL-17 receptor. Yao et al., *Cytokine* 9:794 (1997) [Yao-3]. In an effort to examine the question of receptor specificity directly, Applicants have demonstrated that both IL-17B (SEQ ID NO:1) and IL-17C (SEQ ID NO:3) fail to bind to the IL-17 receptor ECD (SEQ ID NO:16) (FIG. 5A), and also fail to compete for the binding of IL-17 (SEQ ID NO:11) to its receptor ECD (SEQ ID NO:16) (FIG. 5B). IL-17B (SEQ ID NO:1) and IL-17C (SEQ ID NO:3) do bind to the surface of THP1 cells, where they have activity (FIG. 6). The interaction is specific at least to the extent that a control Fc fusion protein fails to bind to these cells. The results suggest that there could be a set of receptors that bind and transduce the signal from the family of IL-17 cytokines, a receptor/ligand model that has been found for many cytokine and growth factor families.

The novel cytokines disclosed herein, PRO1031 (e.g., 516) and PRO1122 (e.g., UNQ561), differ from IL-17 (SEQ ID NO:11) in their patterns of expression and biological activities. The differential expression coupled with the lack of interaction with the known IL-17 receptor suggests and expanded role for the IL-17 family in the proinflammatory immune response.

F. Anti-PRO1031 and Anti-PRO1122 Antibodies

The present invention further provides anti-PRO1031 and anti-PRO1122 polypeptide antibodies. Exemplary antibodies include polyclonal, monoclonal, humanized, bispecific, and heteroconjugate antibodies.

1. Polyclonal Antibodies

The anti-PRO1031 or anti-PRO1122 antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO1031 or PRO1122 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO1031 or anti-PRO1122 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO1031 or PRO1122 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies. Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against a PRO1031 or PRO1122 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., *Proc. Natl. Acad. Sci. USA* 81, 6851-6855 (1984)] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-PRO1031 or anti-PRO1122 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introducing human immunoglobulin loci into transgenic animals, e.g., mice in which the endogenous immunoglobulin genes have been partially or complete inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806; 5,569,825; 5,625,126; 5,633,425; 5,661,016, and in the following scientific publications: Marks et al.,*Bio/Technology* 10: 779-783 (1992); Lonberg et al., *Nature* 368: 856-859 (1994); Morrison, *Nature* 368: 812-13 (1994); Fishwild et al., *Nature Biotechnology* 14: 845-51 (1996); Neuberger, *Nature Biotechnology* 14: 826 (1996); Lonberg and Huszar, *Intern. Rev. Immunol.* 13: 65-93 (1995).

4. Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO 81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such as way so as to convert it into its more active, cytotoxic form.

Enzymes that are useful in the method of this invention include, but are not limited to, glycosidase, glucose oxidase, human lysosyme, human glucuronidase, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug 5-fluorouracil; proteases, such as *serratia* protease, thermolysin, subtilisin, carboxypeptidases (e.g., carboxypeptidase G2 and carboxypeptidase A) and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin Vamidase or penicillin G amidase, useful for converting drugs derivatized at their amine nitrogens with phenoxyacetyl or phenylacetyl groups, respectively, into free drugs. Alternatively, antibodies with enzymatic activity, also known in the art as Aabzymes@ can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the anti-PRO1031 or anti-PRO1122 antibodies by techniques well known in the art such as the use of the heterobifunctional cross-linking agents discussed above. Alternatively, fusion proteins comprising at least the antigen binding region of the antibody of the invention linked to at least a functionally active portion of an enzyme of the invention can be constructed using recombinant DNA techniques well known in the art (see, e.g. Neuberger et al., *Nature* 312: 604-608 (1984)).

5. Bispecific Antibodies

Bispecific antibodies are monoclonal, preferably human or humanized, antibodies that have binding specificities for at least two different antigens. In the present case, one of the binding specificities is for a PRO1031 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory Acavities@ of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab=)$_2$ bispecific antibodies). Techniques for generating bispecific antibodies from antibody fragments have been described in the literature. For example, bispecific antibodies can be prepared can be prepared using chemical linkage. Brennan et al., *Science* 229: 81 (1985) describe a procedure wherein intact antibodies are proteolytically cleaved to generate F(ab=)$_2$ fragments. These fragments are reduced in the presence of the dithiol complexing agent sodium arsenite to stabilize vicinal dithiols and prevent intermolecular disulfide formation. The Fab=fragments generated are then converted to thionitrobenzoate (TNB) derivatives. One of the Fab=-TNB derivatives is then reconverted to the Fab=-thiol by reduction with mercaptoethylamine and is mixed with an equimolar amount of the other Fab=-TNB derivative to form the bispecific antibody. The bispecific antibodies produced can be used as agents for the selective immobilization of enzymes.

Fab=fragments may be directly recovered from *E. coli* and chemically coupled to form bispecific antibodies. Shalaby et al., *J. Exp. Med.* 175: 217-225 (1992) describe the production of a fully humanized bispecific antibody F(ab=)$_2$ molecule.

Each Fab=fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers, Kostelny et al., *J. Immunol.* 148(5): 1547-1553 (1992), wherein the leucine zipper peptides from the Fos and Jun proteins were linked to the Fab=portions of two different antibodies by gene fusion. The antibody homodimers were reduced at the hinge region to form monomers and then re-oxidized to form the antibody heterodimers. This method can also be utilized for the production of antibody homodimers. The Adiabody@ technology described by Hollinger et al., *Proc. Natl. Acad. Sci. USA* 90: 6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152: 5368 (1994).

Antibodies with more than two valencies are contemplated. For example, trispecific antibodies can be prepared. Tutt et al., *J. Immunol.* 147: 60 (1991).

Exemplary bispecific antibodies may bind to two different epitopes on a given APro@ protein herein. Alternatively, an anti-@PRO@ protein arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular APRO@ protein. Bispecific antibodies may also be used to localize cytotoxic agents to cells which express a particular APRO@ polypeptide. These antibodies possess a APRO@-binding arm and an arm which binds a cytotoxic agent or a radionuclide chelator, such as EOTUBE, DPTA, DOTA, or TETA. Another bispecific antibody of interest binds the APRO@ polypeptide and further binds tissue factor (TF).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Effector Function Engineering

It may be desirable to modify the antibody of the invention with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3: 219-230 (1989).

8. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof, or a small molecule toxin), or a radioactive isotope (i.e., a radioconjugate).

Chemotherapeutic agents useful in the generation of such immunoconjugates have been described above. Enzymatically active protein toxins and fragments thereof which can be used include diphtheria A chain, nonbinding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, saporin, mitogellin, restrictocin, phenomycin, enomycin and the tricothecenes. Small molecule toxins include, for example, calicheamicins, maytansinoids, palytoxin and CC1065. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

9. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent (such as Doxorubicin) is optionally contained within the liposome. See Gabizon et al., *J. National Cancer Inst.* 81(19): 1484 (1989).

10. Pharmaceutical Compositions of Antibodies

Antibodies specifically binding a PRO1031 or PRO1122 polypeptide identified herein, as well as other molecules identified by the screening assays disclosed hereinbefore, can be administered for the treatment of various disorders in the form of pharmaceutical compositions.

If a PRO1031 or PRO1122 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA* 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokines, chemotherapeutic agent, or growth-inhibitory agent. Such molecules are suitable present in combination in amounts that are effective for the purpose intended.

The active ingredients may also be entrapped in microcapsules prepared, for example, by coascervation techniques or by interfacial polymerization, for example, hydroxymethylcellulose or felatin-microcapsules and poly-(methylmethactylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences, supra*.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid γ-ethyl-L-glutamate, non-degradable ethylene-vinylacetate, degradable lactic acid-glycolic acid copolymers such as the LUPRON DEPOT™ (injectable microspheres composed of lactic acid-glycolic acid copolymer and leuprolide acetate), and poly-D-(−)$_3$-hydroxylbutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanisms involved. For example, if the aggregation mechanism is discovered to be intermolecular S—S bond formation through thiosulfide interchange, stabilization may be achieved by modifying sulfhydryl residues, lyophilizing from acidic solutions, controlling moisture content, using appropriate additives, and developing specific polymer matrix compositions.

G. Uses for Anti-PRO1031 and Anti-PRO1122 Antibodies

The anti-PRO1031 and anti-PRO1122 antibodies of the present invention have various utilities. For example, anti-PRO1031 or anti-PRO1122 antibodies may be used in diagnostic assays for PRO1031 or PRO1122 polypeptides, e.g., detecting expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-PRO1031 or anti-PRO1122 antibodies also are useful for the affinity purification of PRO1031 or PRO1122 polypeptides, respectively, from recombinant cell culture or natural sources. In this process, the antibodies against a PRO1031 or PRO1122 polypeptide are immobilized on a suitable support, such a Sephadex resin or filter paper, using methods well known in the art. The immobilized antibody then is contacted with a sample containing the PRO1031 or PRO1122 polypeptide to be purified, and thereafter the support is washed with a suitable solvent that will remove substantially all the material in the sample except the PRO1031 or PRO1122 polypeptide, which is bound to the immobilized antibody. Finally, the support is washed with another suitable solvent that will release the PRO1031 or PRO1122 polypeptide from the antibody.

H. PRO1031, PRO1122 and IL-17 Antagonists/Agonists

This invention encompasses methods of screening compounds to identity those that mimic the PRO1031, PRO1122 or IL017 polypeptide (agonists) or prevent the effect of the PRO1031, PRO1122 or IL-17 polypeptide (antagonists). Screening assays for antagonist drug candidates are designed to identity compounds that bind or complex with the PRO1031, PRO1122, IL-17 polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art. For example, to screen for antagonists and/or agonists of PRO1031, PRO1122, IL-17 signaling, the assay mixture is incubated under conditions whereby, but for the presence of the candidate pharmacological agent, PRO1031, PRO1122 or IL-17 induces TNF-α release from THP-1 cells with a reference activity. Alternatively, the tested activity can be the release of nitric oxide (NO) and proteoglycans from IL17 and/or IL-1α treated articular cartilage.

In binding assays, the interaction is binding and the complex formed can be isolated or detected in the reaction mixture. In a particular embodiment, the PRO1031, PRO1122 or IL-17 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO1031, PRO1122 or IL-17 polypeptide and drying. Alternatively, an immobilized antibody, e.g., a monoclonal antibody, specific for the PRO1031, PRO1122 or IL-17 polypeptide to be immobilized can be used to anchor it to solid surface. The assay is performed by adding the non-immobilized component, which may be labeled by a detectable label, to the immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO1031, PRO132 or IL-17 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored through gradients or chromatographic columns. In addition, protein-protein interactions can be monitored by using a yeast-based genetic system described by Fields and co-workers (Fields and Song, *Nature* 340: 245-246 (1989); Chien et al., *Proc. Natl. Acad. Sci. USA* 88: 9578-9582 (1991) as disclosed by Chevray and Nathans, *Proc. Natl. Acad. Sci. USA* 89: 5789-5791 (1991). Many transcriptional activators, such as yeast GAL4, consist of two physically discrete modular domains, one acting as the DNA-binding domain, while the other functions as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of GAL1-lacZ reporter gene under control of a GAL4-activated promoter depends on reconstitution of GAL4 activity via protein-protein interaction. Colonies containing interacting polypeptide are detected with chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO1031, PRO1122 or IL-17 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as a positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

Antagonists may be detected by combining the PRO1031, PRO1122 or IL-17 polypeptide and a potential antagonist with membrane-bound PRO1031, PRO1122 or IL-17 polypeptide receptors or recombinant receptors under appropriate conditions for a competitive inhibition assay. The PRO1031, PRO1122 or IL-17 polypeptide can be labeled, such as by radioactivity, such that the number of PRO1031, PRO1122 or IL-17 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.* 1(2): Ch. 5 (1991). Preferably, expression cloning is employed wherein polyadenylated RNA is prepared from a cell responsive to the PRO1031 or PRO1122 polypeptide and a cDNA library created from this RNA is divided into pools and used to transfect COS cells or other cells that are not responsive to the PRO1031, PRO1122 or IL-17 polypeptide, respectively. Transfected cells that are grown on glass slides are exposed to labeled PRO1031, PRO1122 or IL-17 polypeptide. The PRO1031, PRO1122 or IL-17 polypeptide can be labeled by a variety of means including iodination or inclusion of a recognition site for a site-specific protein kinase. Following fixation and incubation, the slides are subjected to autoradiographic analysis.

Positive pools are identified and sub-pools are prepared and re-transfected using an interactive sub-pooling and re-screening process, eventually yielding a single clone that encodes the putative receptor.

As an alternative approach for receptor identification, labeled PRO1031, PRO1122 or IL-17 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identity the gene encoding the putative receptor.

In another assay for antagonists, mammalian cells or a membrane preparation expressing the receptor would be incubated with labeled PRO1031, PRO1122 or IL-17 polypeptide in the presence of the candidate compound. The ability of the compound to enhance or block this interaction could then be removed.

More specific examples of potential antagonists include an oligonucleotide that binds to the fusions of immunoglobulin with PRO1031, PRO1122 or IL-17 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO1031, PRO122 or IL-17 polypeptide that recognizes the receptor but impart no effect, thereby competitively inhibiting the action of the PRO1031, PRO122 or IL-17 polypeptide.

Another potential PRO1031, PRO1122 or IL-17 polypeptide antagonist is an antisense RNA or DNA construct prepared using antisense technology, where, e.g., an antisense RNA or DNA molecule acts to block directly the translation of mRNA by hybridizing to targeted mRNA and preventing its translation into protein. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO1031, PRO1122 or IL-17 polypeptides herein, is used to design an antisense RNA oligonucleotide sequence, which encodes the mature PRO1031, PRO1122 or IL-17 polypeptides herein, is used to design an antisense RNA oligonucleotide of about 10 to 40 base pairs in length. A DNA oligonucleotide is designed to be complementary to a region of the gene involved in transcription (triple helix—see Lee et al., *Nucl. Acids Res.* 6: 3073 (1979); Cooney et al., *Science* 241: 456 (1988); Dervan et al., *Science* 251: 1360 (1991)), thereby preventing transcription and the production of the PRO1031 or PRO1122 polypeptide. The antisense RNA oligonucleotide hybridizes to the mRNA in vivo and blocks translation of the mRNA molecule into the PRO1031, PRO1122 or IL-17 polypeptide (antisense— Okano, *Neurochem.* 546: 560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO1031, PRO1122, IL-17 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO1031 or PRO1122 polypeptide, thereby blocking the normal biological activity of the PRO1031, PRO1122 or IL-17 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonuclytic cleavage. Specific ribozyme cleavage sites within a potential RNA target can be identified by known techniques. For further details, see e.g., Rossi, Current Biology 4: 469-471 (1994) and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCR publication No. WO 97/33551, supra.

I. Diagnostic Uses

Another use of the compounds of the invention (e.g., PRO1031- or PRO1122-variants and anti-PRO1031 or anti-PRO1122 antibodies) described herein is to help diagnose whether a disorder is driven, to some extent, by PRO1031 or PRO1122 modulated signaling. A diagnostic assay to determine whether a particular disorder (e.g., degenerative cartilaginous disorder) is driven by PRO1031 or PRO1122 signaling, can be carried out using the following steps: (1) culturing test cells or tissues expressing PRO1031 or PRO1122; (2) administering a compound which can inhibit PRO1031 or PRO1122 modulated signaling; and (3) measuring the PRO1031 or PRO1122 mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of PRO1031 or PRO1122. For example, compounds which PRO1031 or PRO1122 in addition to another form of adaptor molecule can be used as an initial test compound to determine if one of several adaptor molecules drive the disorder. The selective compounds can then be used to further eliminate the possible role of the other adaptor proteins in driving the disorder. Test compounds should be more potent in inhibiting intracellular signaling activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of PRO1031 or PRO1122 upon degenerative cartilagenous disorders. Exemplary detection techniques include radioactive labeling and immunoprecipitating (U.S. Pat. No. 5,385,915).

For example, antibodies, including antibody fragments, can be used to qualitatively or quantitatively detect the expression of proteins encoded by the disease-related genes (Amarker gene products@). The antibody preferably is equipped with a detectable, e.g. fluorescent label, and binding can be monitored by light microscopy, flow cytometry, fluorimetry, or other techniques known in the art.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

J. Pharmaceutical Compositions

The PRO1031 or PRO1122, antagonists or agonists thereof (e.g., antibodies), as well as other molecules identified by the screening assays disclosed hereinbefore, can be employed as therapeutic agents. Such therapeutic agents are formulated according to known methods to prepare pharmaceutically useful compositions, whereby the PRO1031 or PRO1122, antagonist or agonist thereof is combined in admixture with a pharmaceutically acceptable carrier.

In the case of PRO1031 or PRO1122 antagonist or agonist antibodies, if the protein encoded by the amplified gene is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90: 7889-7893 [1993]).

Therapeutic formulations are prepared for storage by mixing the active ingredient having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Therapeutic compositions herein generally are placed into a container having a sterile access port, for example, and intravenous solution bag or vial having a stopper pierceable by a hypodermic injection needle.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon- (rhIFN-), interleukin-2, and MN rpg 120. Johnson et al., Nat. Med. 2: 795-799 (1996); Yasuda et al., Biomed. Ther. 27: 1221-1223 (1993); Hora et al., Bio/Technology 8: 755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds., (Penum Press: New York, 1995), pp. 439-462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in *Biodegradable Polymers as Drug Delivery Systems* (Marcel Dekker; New York, 1990), M. Chasin and R. Langer (Eds.) pp. 1-41.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37EC, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

K. Methods of Treatment

It is contemplated that the compounds of the present invention may be used to treat various conditions, including those characterized by overexpression and/or activation of the disease-associated genes identified herein. Exemplary conditions or disorders to be treated with such antibodies and other compounds, including, but not limited to, small organic and inorganic molecules, peptides, antisense molecules, etc. include inflammatory and immunologic disorders, especially those characterized by cartilage matrix breakdown such as arthritis, (e.g., osteoarthritis, psoriatic arthritis, rheumatoid arthritis) or other degenerative inflammatory diseases.

The active agents of the present invention, e.g. antibodies, are administered to a mammal, preferably a human, in accord with known methods, such as intravenous administration as a bolus or by continuous infusion over a period of time, by intramuscular, intraperitoneal, intracerebral, intracerobrospinal, subcutaneous, intra-articular, intrasynovial, intrathecal, intraoccular, intralesional, oral, topical, inhalation or through sustained release.

Other therapeutic regimens may be combined with the administration of the PRO1031, PRO1122, antagonists or antagonists, anti-cancer agents, e.g. antibodies of the instant invention.

For the prevention or treatment of disease, the appropriate dosage of an active agent, (e.g. an antibody) will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective does for human therapy. Interspecies scaling of effective doses can be performed following the principles laid down by Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

When in vivo administration of a PRO1031 or PRO1122 polypeptide or agonist or antagonist thereof is employed, normal dosage amounts may vary from about 10 ng/kg up to 100 mg/kg of mammal body weight or more per day, preferably about 1 µg/kg/day up to 100 mg/kg of mammal body weight or more pre day, depending upon the route of administration. Guidance as to particular dosages and methods of delivery is provided in the literature; see, for example, U.S. Pat. No. 4,657,760, 5,206,344 or 5,255,212. It is within the scope of the invention that different formulations will be effective for different treatment compounds and different disorders, that administration targeting one organ or tissue, for example, may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

L. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is typically a PRO1031, PRO1122 polypeptide, antagonist, or agonist thereof. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA Clones Encoding Human PRO1031

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank, Merck/Wash U.) and a proprietary EST DNA database (LIFESEQ®, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

An initial virtual sequence fragment (consensus assembly) was assembled relative to other EST sequences using phrap. The initial consensus DNA sequence was extended using repeated cycles of BLAST and phrap to extend the consensus sequence as far as possible using the sources of EST sequences discussed above. The results of this assembly is shown in SEQ ID NO:5, also referred to as DNA47332.

One sequence comprising the consensus assembly, W74558 (clone 344649) (SEQ ID NO:6) was further examined. The sequence was obtained from the IMAGE consortium and analyzed. Lennon et al., Genomics 33: 151 (1996). DNA sequencing gave the full-length DNA sequence for PRO1031 [herein designated as DNA59294-1381] (SEQ ID NO:2) and the derived PRO1031 protein sequence (UNQ516) (SEQ ID NO: 1).

The entire nucleotide sequence of DNA59294-1381 is shown in SEQ ID NO:2. Clone DNA59294-1381 contains a single open reading frame with an apparent translational initiation site at nucleotide positions 42-44 and ending at the stop codon at nucleotide positions 582-584 SEQ ID NO:2. The predicted polypeptide precursor is 180 amino acids long SEQ ID NO:1. The full-length PRO1031 (UNQ516) protein shown in SEQ ID NO:1 has an estimated molecular weight of about 20437 and a pI of about 9.58. Clone DNA59294-1381 (SEQ ID NO:2) has been deposited with the ATCC, and have been assigned deposit number 209866. In the event of any sequencing irregularities or errors with the sequences provided herein, it is understood that the deposited clone contains the correct sequence for DNA59624 (SEQ ID NO:2). Furthermore, the sequences provided herein are the result of known sequencing techniques.

Analysis of the amino acid sequence of the full-length PRO1031 polypeptide (UNQ516) (SEQ ID NO:1) suggests that it is a novel cytokine.

Further analysis of the amino acid sequence of SEQ ID NO:2 reveals that the putative signal peptide is at about amino acids 1-20 of SEQ ID NO:2. An N-glycosylation site is at about amino acids 75-78 of SEQ ID NO:2. A region having sequence identity with IL-17 is at about amino acids 96-180. The corresponding nucleotides can be routinely determined given the sequences provided herein.

Example 2

Isolation of cDNA Clones Encoding Human PRO1122

An expressed sequence tag (EST) DNA database (LIFESEQ®, Incyte Pharmaceuticals, Palo Alto, Calif.) was searched and an EST was identified. The EST was Incyte 1347523 (SEQ ID NO:7) also called DNA49665. Based on DNA49665 (SEQ ID NO:7), oligonucleotides were synthesized: 1) to identify by PCR a cDNA library that contained the sequence of interest, and 2) for use as probes to isolated a clone of the full-length coding sequence for the PRO1122. [e.g., Sambrook et al., *Molecular Cloning: A Laboratory Manual* (New York: Cold Spring Harbor Laboratory Press, 1989); Dieffenbach et al., *PCR Primer: A Laboratory Manual* (Cold Spring Harbor Laboratory Press, 1995)].

Forward and reverse PCR primers generally range from 20 to 30 nucleotides and are often designed to give a PCR product of about 100-1000 bp in length. The probes sequences are typically 40-55 bp in length. In some cases, additional oligonucleotides are synthesized when the consensus sequence is greater than about 1-1.5 kpb. In order to screen several libraries for a full-length clone, DNA from the libraries was screened by PCR amplification, as per Ausuble et al., *Current Protocols in Molecular Biology*, with the PCR primer pair. A positive library was then used to isolate clones encoding the gene of interest using the probe oligonucleotide and one of the primer pairs.

PCR primers (forward, reverse and hybridization) were synthesized:

```
forward PCR primer:
                                         (SEQ ID NO:8)
5'-ATCCACAGAAGCTGGCCTTCGCCG-3' reverse PCR primer:
                                         (SEQ ID NO:9)
5'-GGGACGTGGATGAACTCGGTGTGG-3' hybridization probe:
                                         (SEQ ID NO: 10)
5'-TATCCACAGAAGCTGGCCTTCGCCGAGTGCCTGTGCAGAG-3'.
```

In order to screen several libraries for a source of a full-length clone, DNA from the libraries was screened by PCR amplification with the PCR primer pair identified above. A positive library was then used to isolate clones encoding the PRO1122 gene using the probe oligonucleotide and one of the PCR primers.

RNA for construction of the cDNA libraries was isolated from human fetal kidney tissue. The cDNA libraries used to isolate the cDNA clones were constructed using standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science 235: 1278-1280 (1991)) in the unique XhoI and NotI sites.

DNA sequencing of the clones isolated as described above gave the full-length DNA sequence for PRO1122 [herein designated as DNA62377-1381-1](SEQ ID NO:4) and the derived protein PRO1122 sequence (UNQ561) (SEQ ID NO:3).

The entire nucleotide sequence of DNA62377-1381-1 (SEQ ID NO:4) is shown in SEQ ID NO:4. Clone DNA62377-1381-1 (SEQ ID NO:4) contains a single open reading frame with an apparent translational initiation site at nucleotide positions 50-52 and ending at the stop codon at nucleotide positions 641-643 of SEQ ID NO:4. The predicted polypeptide precursor is 197 amino acids long SEQ ID NO:3. The full-length PRO1122 protein shown in SEQ ID NO:3 (UNQ561) has an estimated molecular weight of about 21765 daltons and a pI of about 8.53. Clone DNA62377-1381-1 has been deposited with the ATCC on Dec. 22, 1998 and has been assigned deposit number 203552. It is understood that in the event or a sequencing irregularity or error in the sequences provided herein, the correct sequence is the sequence deposited. Furthermore, all sequences provided herein are the result of known sequencing techniques.

Analysis of the amino acid sequence of the isolated full-length PRO1122 (UNQ561) suggests that it possesses similarity with IL-17, thereby indicating that PRO1122 (UNQ561) may be a novel cytokine. In FIG. 2 of U.S. Provisional Application No. 60/113,621, filed Dec. 23, 1998, which is incorporated by reference, the approximate locations of the signal peptide, leucine zipper pattern, and a region having sequence identity with IL-17 were disclosed as amino acids 1-18, 3-24, and 99-195, respectively. The corresponding nucleotides can be routinely determined, e.g., by reference to SEQ ID NO:4.

Example 3

Use of PRO1031- or PRO1122-Encoding DNA as a Hybridization Probe

The following method describes use of a nucleotide sequence encoding PRO1031 as a hybridization probe.

DNA comprising the coding sequence of full-length PRO1031 (as shown in SEQ ID NO:2), PRO1122 (as shown in SEQ ID NO:4), or a fragment thereof is employed as a probe to screen for homologous DNAs (such as those encoding naturally-occurring variants of PRO1031 or PRO1122 in human tissue cDNA libraries or human tissue genomic libraries.

Hybridization and washing of filters containing either library DNAs is performed under the following high stringency conditions. Hybridization of radiolabeled PRO1031 or PRO1122 polypeptide-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO1031 or PRO1122 polypeptide can then be identified using standard techniques known in the art.

Example 4

Expression of PRO1031 or PRO1122 Polypeptides in *E. coli*

This example illustrates the preparation of unglycosylated forms of PRO1031 or PRO1122 polypeptides by recombinant expression in *E. coli*.

The DNA sequence encoding the full-length PRO1031, PRO1122 or a fragment or variant thereof is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO1031 or PRO1122 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO1031 or PRO1122 polypeptide can then be purified using a metal chelating column under conditions that allow tight binding of the polypeptide.

Example 5

Expression of PRO1031 or PRO1122 Polypeptides in Mammalian Cells

This example illustrates preparation of glycosylated forms of PRO1031 or PRO1122 polypeptides by recombinant expression in mammalian cells.

The vector, pRK5 (see EP 307,247, published Mar. 15, 1989), is employed as the expression vector. Optionally, the PRO1031- or PRO1122-encoding DNA is ligated into pRK5 with selected restriction enzymes to allow insertion of the PRO1031- or PRO1122-encoding DNA using ligation methods such as described in Sambrook et al., supra. The resulting vector is called pRK5-PRO1031 or pRK5-PRO1122, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-PRO1031 or pRK5-PRO1122 DNA is mixed with about 1 µg DNA encoding the VA RNA gene [Thimmappaya et al, Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO1031 or PRO1122 polypeptide. The cultures containing transfected cells may undergo further incubation (in serum free medium) and the medium is tested in selected bioassays.

In an alternative technique, PRO1031- or PRO1122-encoding DNA may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-PRO1031 or pRK5-PRO1122 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO1031 or PRO1122 polypeptide can then be concentrated and purified by any selected method, such as dialysis and/or column chromatography.

In another embodiment, PRO1031 or PRO1122 polypeptide can be expressed in CHO cells. The pRK5-PRO1031 or pRK5-PRO1122 vector can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO1031 or PRO1122 polypeptide, the culture medium may be replaced with serum free medium. Preferably, the cultures are incubated for about 6 days, and then the conditioned medium is harvested. The medium containing the expressed PRO1031 or PRO1122 polypeptide can then be concentrated and purified by any selected method.

Epitope-tagged PRO1031 or PRO1122 polypeptide may also be expressed in host CHO cells. The PRO1031- or PRO1122-encoding DNA may be subcloned out of the pRK5 vector. The subclone insert can undergo PCR to fuse in frame with a selected epitope tag such as a poly-his tag into a Baculovirus expression vector. The poly-his tagged PRO1031- or PRO1122-encoding DNA insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO1031 or PRO1122 polypeptide can then be concentrated and purified by any selected method, such as by $Ni^{2+}$-chelate affinity chromatography.

Example 6

Expression of a PRO1031 Polypeptide in Yeast

The following method describes recombinant expression of PRO1031 or PRO1122 polypeptides in yeast.

First, yeast expression vectors are constructed for intracellular production or secretion of PRO1031 or PRO1122 polypeptide from the ADH2/GAPDH promoter. DNA encoding the PRO1031 or PRO1122 polypeptide of interest, a selected signal peptide and the promoter is inserted into suitable restriction enzyme sites in the selected plasmid to direct intracellular expression of the PRO1031 or PRO1122 polypeptide. For secretion, DNA encoding the PRO1031 or PRO1122 polypeptide can be cloned into the selected plasmid, together with DNA encoding the ADH2/GAPDH promoter, the yeast alpha-factor secretory signal/leader sequence, and linker sequences (if needed) for expression of the PRO1031 or PRO1122 polypeptide.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO1031 or PRO1122 polypeptide can subsequently be isolated and purified by removing the yeast cells from the fermentation medium by centrifugation and then concentrating the medium using selected cartridge filters. The concentrate containing the PRO1031 or PRO1122 polypeptide may further be purified using selected column chromatography resins.

Example 7

Expression of PRO1031 or PRO1122 Polypeptides in Baculovirus-Infected Insect Cells The following method describes recombinant expression of PRO1031 or PRO1122 polypeptides in Baculovirus-infected insect cells.

The PRO1031- or PRO1122-encoding DNA is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the PRO1031- or PRO1122-encoding DNA or the desired portion of the PRO1031- or PRO1122-encoding DNA (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4 to 5 days of incubation at 28° C., the released viruses are harvested and used for further amplifications. Viral infection and protein expression is performed as described by O'Reilley et al., Baculovirus Expression vectors: A Laboratory Manual, Oxford:Oxford University Press (1994).

Expressed poly-his tagged PRO1031 or PRO1122 polypeptide can then be purified, for example, by $Ni^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged PRO1031 polypeptide are pooled and dialyzed against loading buffer.

Alternatively, purification of the IgG tagged (or Fc tagged) PRO1031 polypeptide can be performed using known chromatography techniques, including for instance, Protein A or protein G column chromatography.

Example 8

Preparation of Antibodies that Bind PRO1031 or PRO1122 Polypeptides

This example illustrates the preparation of monoclonal antibodies which can specifically bind to PRO1031 or PRO122 polypeptides.

Techniques for producing the monoclonal antibodies are known in the art and are described, for instance, in Goding, supra. Immunogens that may be employed include purified PRO1031 or PRO1122 polypeptide, fusion proteins containing a PRO1031 or PRO1122 polypeptide, and cells expressing recombinant PRO1031 or PRO1122 polypeptide on the cell surface. Selection of the immunogen can be made by the skilled artisan without undue experimentation.

Mice, such as Balb/c, are immunized with the PRO1031 or PRO1122 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO1031 or anti-PRO1122 polypeptide antibodies.

After a suitable antibody titer has been detected, the animals "positive" for antibodies can be injected with a final intravenous injection of PRO1031 or PRO1122 polypeptide. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO1031 or PRO1122 polypeptide. Determination of "positive" hybridoma cells secreting the desired monoclonal antibodies against a PRO1031 or PRO1122 polypeptide is within the skill in the art.

The positive hybridoma cells can be injected intraperitoneally into syngeneic Balb/c mice to produce ascites containing the anti-PRO1031 or anti-PRO1122 polypeptide monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

RNA Expression

Multi-tissue blots containing poly A$^+$ RNA (2 µg per lane) from various human tissues were purchased from Clontech (Palo Alto, Calif.). The entire coding regions of human IL-17B (UNQ516) (700 bp) (SEQ ID NO:17) and IL-17C (UNQ561) (1.1 kbp) (SEQ ID NO:18) were used as hybridization probes. DNA probes were labeled with [$\alpha$-$^{32}$P]-dCTP by random priming DNA labeling beads (Pharmacia Biotech). Hybridization was performed using Expresshyb (Clontech) containing the radiolabeled probes at 68° C. for 1 hour. The blots were then washed with 2×SSC/0.05% SDS solution at room temperature for 40 minutes, followed by washes in 0.1×SSC/0.05% SDS solution at 55° C. for 40 minutes with one change of fresh solution. The blots were exposed in a phosphorimager and the resulting image is reported herein as FIG. 2.

For IL-17B (SEQ ID NO:1), an 800 bp mRNA transcript was found in pancreas, small intestine, and stomach of adult human tissues; a weaker band was detected in testis. (FIG. 2). IL-17C (SEQ ID NO:2) expression was examined in the same set of adult human tissues, but no detectable signals were observed.

Example 10

Generating Fc/His Fusion Proteins

The coding sequences of IL17B (SEQ ID NO:17) and IL17C (SEQ ID NO:18) were amplified by PCR and subcloned into the EcoRI and SmaI sites of pBPH.His.c to generate a C-terminal GHHHHHHHH tag (SEQ ID NO:19) or the EcoRI and Stu sites of pBPH.IgG to generate a C-terminal fusion with the Fc region of human IgG1. Vectors pBPH.His.c and pBPH.IgG are derivatives of the baculovirus expression vector pVL1393 (Pharmingen). A control Fc or his-tagged protein was constructed in a similar way be C-terminally linking pancreatitis-associated protein (175 amino acid) to the Fc portion of the human IgG1 or a his8 tag.

The fusion proteins were expressed in H5 cells using the manufacturer's recommended procedure (Invitrogen). In brief, the DNA constructs were co-transfected with BaculoGold Baculovirus DNA (Pharmingen) in a 7:1 ratio into adherent Sf9 cells. Cells were incubated at 28° C. for 4 days and the supernatent was harvested. The transfection supernatant was amplified and was subject to affinity purification by either protein A-sepharose beads (Pharmacia) for Fc fusion proteins or Ni-NTA agarose beads (QIAGEN) for His-tagged proteins.

To examine the protein expression, SDS-PAGE analysis was performed on the affinity purified recombinant proteins under non-reducing and reducing conditions, followed by silver staining.

Example 11

Induction of IL-6 and TNF-α Release

Using the procedure outlined in Yao et al., *J. Immunol.* 155: 5483 (1995) (Yao-2) for IL-6 (SEQ ID NO:14) release, human foreskin fibroblast cells (ATCC CRL-2091) were cultured in MEM media (10% FBS) with the test cytokine. After incubation for 18 hours at 37° C. and 5% CO$_2$, conditioned media were assayed for IL-6 using an ELISA kit (R&D Systems). For TNF-α secretion, human leukemia monocytic THP-1 cells were cultured in RPMI media (10% FBS) with test cytokine. After incubation for 18 hour at 37° C. and 5% CO$_2$, conditioned media were quantitated for TNF-αα(SEQ ID NO:20) using and ELISA assay kit (R&D Systems).

Human foreskin fibroblast cells (ATCC) were separately cultured in MEM media (10% FBS) in the presence of IL-17B (UNQ516) (SEQ ID NO:1) and IL-17C (UNQ561) (SEQ ID NO:3). After incubation for 18 hours at 37° C. and 5% CO$_2$, conditioned media were assayed for IL-6 (SEQ ID NO:14)

using an ELISA kit (R&D Systems). In contrast to the high level of IL-6 (SEQ ID NO:14) induced by IL-17 (SEQ ID NO:11), both IL-17B (SEQ ID NO:1) and IL17C (SEQ ID NO:3) failed to stimulate IL-6 (SEQ ID NO:14) secretion in fibroblast cells (FIG. 3A).

Using the procedure outlined in Yao et al, *Cytokine* 9: 794 (1997) [Yao-3], a human leukemic monocytic cell line, THP-1, was used to assay for the stimulation of TNF-α (SEQ ID NO:20) release by IL-17 (SEQ ID NO:11), UNQ516 (SEQ ID NO:1) and UNQ561 (SEQ ID NO:3) by culturing in RPMI media (10% FBS). After incubation for 18 hour at 37° C. and 5% $CO_2$, conditioned media were quantitated for TNF-α (SEQ ID NO:19) using and ELISA assay kit (R&D Systems). While IL-17 (SEQ ID NO:11) induced only a low level of TNF-α (SEQ ID NO:19) in THP-1 cells, both IL-17B and IL-17C (as Fc fusion proteins) stimulated TNF-α production in THP-1 cells (FIG. 3B). A control Fc fusion protein had no effect.

Figure 4:
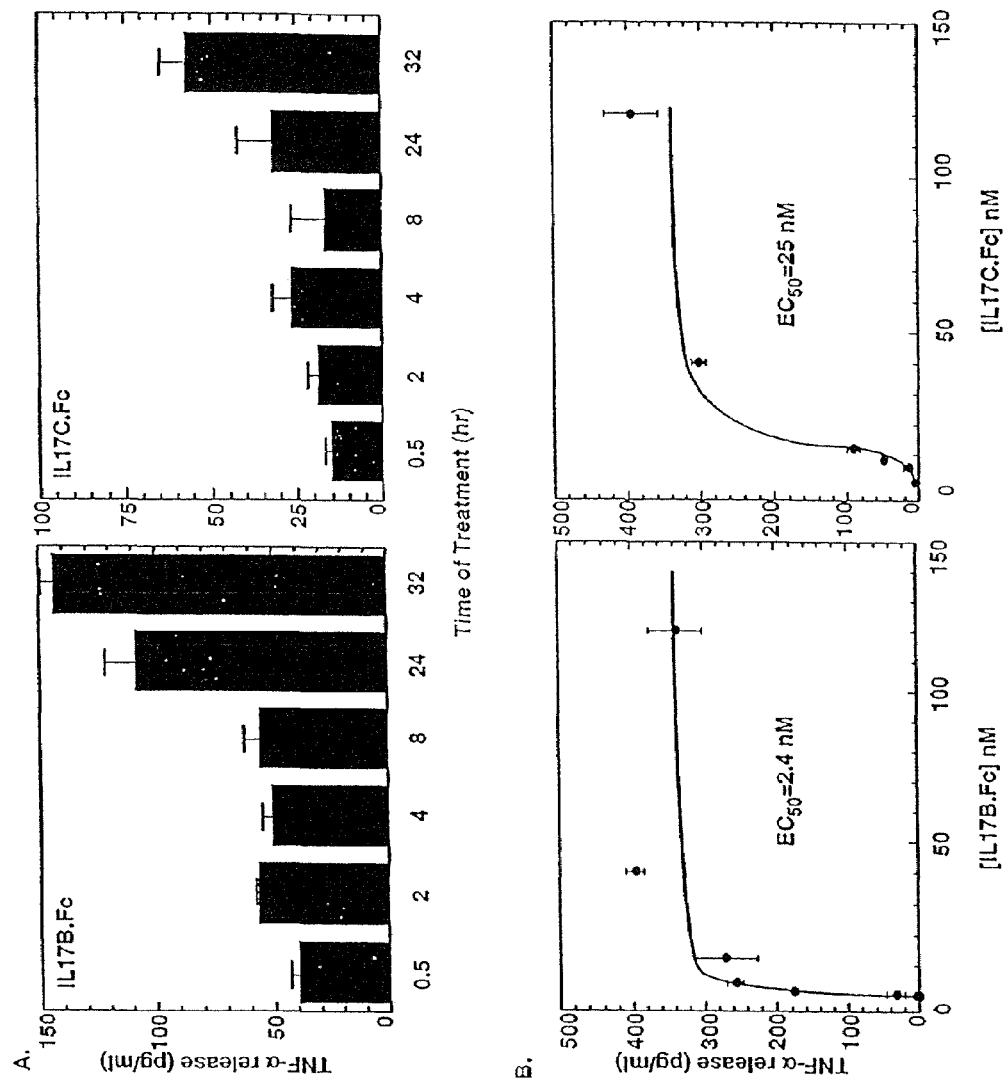
FIG. 4 is a time course representing the dependence of IL17B and IL17C activated TNF-α release from THP1 cells.

In order to further characterize the stimulation of TNF-α: release by IL-17B and IL-17C, the time course and concentration dependence of the response were assayed in THP-1 cells. FIG. 4 illustrates that IL-17B (UNQ516) (SEQ ID NO:1) and IL-17C (UNQ561) (SEQ ID NO:3) stimulate the release of TNF-α (SEQ ID NO:19) in a time- and concentration-dependent manner. The $EC_{50}$ for IL-17B (UNQ516) (SEQ ID NO:1) stimulation is 2.4 nM, while for IL-17C (UNQ561) (SEQ ID NO:3), 25 nM.

While the IL-17B (UNQ516) (SEQ ID NO:1) and IL-17C (UNQ561) (SEQ ID NO:3) preparations used in these experiments contained undetectable level of endotoxin (less than 1 EU/ml), additional control experiments were performed to confirm that the TNF-α (SEQ ID NO:19) release from THP-1 cells was real and not artifactual. The IL-17B (UNQ516) (SEQ ID NO:1) and IL-17C (UNQ561) (SEQ ID NO:3) activities were unaffected by polymyxin B treatment and were abolished by heat treatment, further supporting the notion that the proteins themselves were responsible for the activities and not any contaminating endotoxin.

Example 12

IL-17 Receptor Binding

Cloning of the ECD of hIL-17 Receptor:

In order to clone the ECD of the human IL-17 receptor, two oligonucleotide primers were designed at the 5' and 3' ends of IL-17R ECD (SEQ ID NO:15) based on the published sequence. Yao et al., supra (Yao-3). The two probes had the following sequences: primer 1: 5'-CTG TAC CTC GAG GGT GCA GAG-3' (SEQ ID NO:20) primer 2: 5'-CCC AAG CTT GGG TCA ATG ATG ATG ATG ATG ATG ATG CCA CAG GGG CAT GTA GTC C-3' (SEQ ID NO:21)

The above primers were used in PCR reactions to amplify the full-length cDNA from a human testis cDNA library with Pfu Turbo DNA polymerase (Promega). A C-terminal his tag was introduced by PCR through the addition of nucleotides encoding eight histidines to the 3' end primer. The PCR product was then subcloned into an expression plasmid vector pRK5B. Sequence analysis confirmed that the insert contains a DNA fragment encoding the extracellular domain (1-320 amino acids) of the published hIL-17 receptor. (SEQ ID NO:15).

Immunoprecipitation of the IL-17R ECD:

The differential activity of IL-17 when compared to IL-17B (UNQ516) (SEQ ID NO:1) and IL-17C (UNQ561) (SEQ ID NO:3) suggested that they might bind and activate different cell surface receptors. In order to test whether IL-17B (UNQ516) (SEQ ID NO:1) or IL-17C (UNQ561) (SEQ ID NO:3) directly bind to the receptor, an expression plasmid containing the IL-17R(C-terminal his-tagged) (SEQ ID NO:22) was transfected into 293 cells using SuperFect transfection reagent (Quiagen). Metabolic labeling of 293 cells was performed 16 hours after transfection using 50 μCi/ml [$^{35}$S]-Cys/Met mixture for 6 hours. Conditioned medium was collected and concentrated (Centricon-10, Amicon). To examine the expression of the IL-17R ECD (SEQ ID NO:15), Ni-NTA beads (Quiagen) were used to affinity precipitate the his-tagged IL-17R ECD (SEQ ID NO:22) from the conditioned medium.

The conditioned medium was diluted in RIPA buffer (1% NP40, 0.5% sodium deoxycholate, 0.1% SDS in PBS) was incubated with IL-17 (SEQ ID NO:111) and the Fc fusion proteins overnight at 4° C. Protein A-agarose beads (Pierce) were added to precipitate the Fc fusion proteins. The precipitates were washed three times to precipitate the Fc fusion proteins. The precipitates were washed three times in RIPA buffer, denatured in SDS sample buffer, and electrophoresed on NuPAGE 4-12% Bis-Tris gels (Novex). For IL-17 (SEQ ID NO: 11) immunoprecipitation, anti-IL-17 antibody (R&D Systems) was added. In a competitive binding experiment, immunoprecipitation of IL-17R ECD (SEQ ID NO:15) by IL-17 (SEQ ID NO:11) is performed in the presence of a 5-fold molar excess of IL-17B.his (SEQ ID NO:23, IL-17C.his (SEQ ID NO:24 and control his tagged protein.

Figure 11:
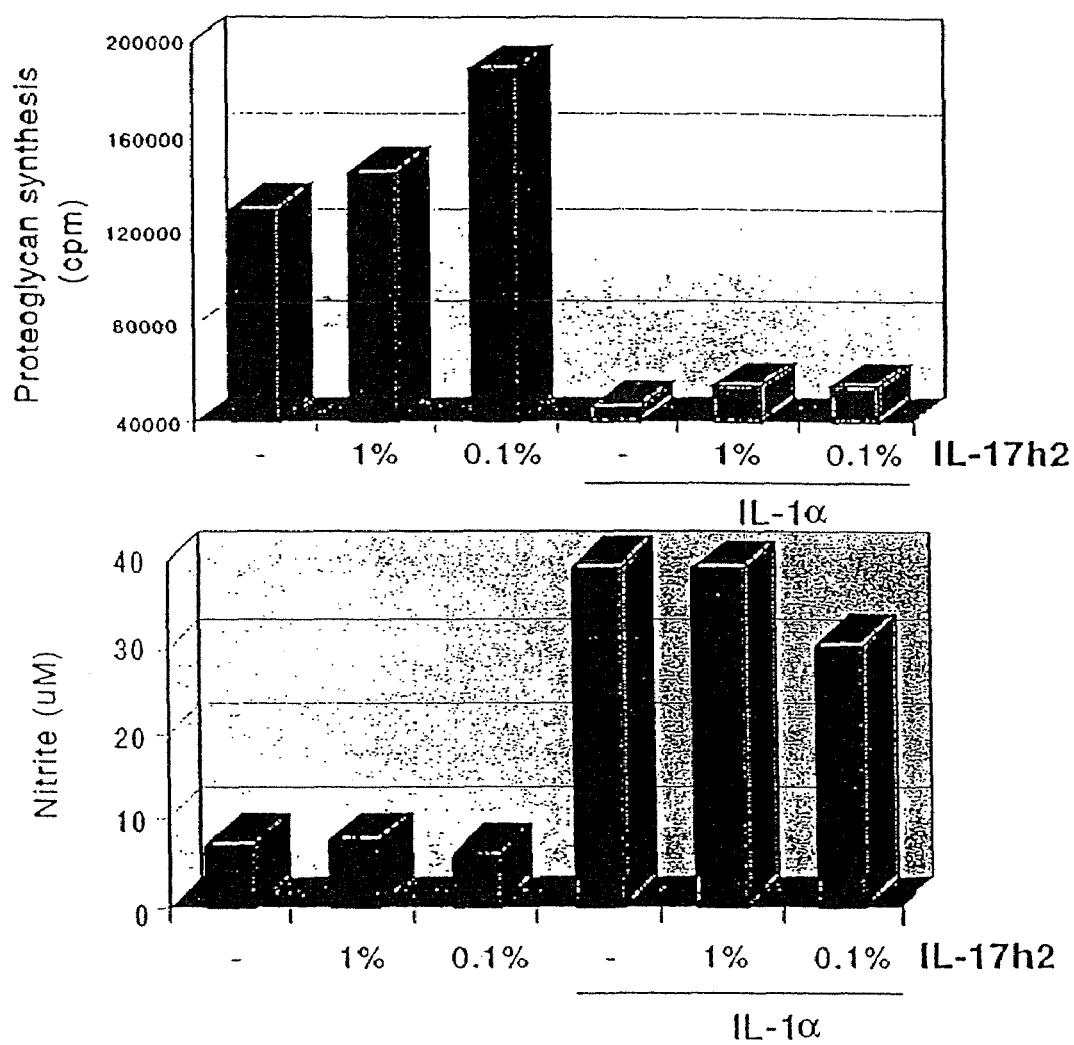
FIG. 11 shows the effect of UNQ516 (SEQ ID NO:1) on articular cartilage. Explants were treated with UNQ561 at 1% or 0.1% in the absence (leftmost 3 columns) or presence (rightmost three columns) of IL-1α (SEQ ID NO:25) at 10 ng/ml, and proteoglycan (PG) synthesis and nitrite production were determined as described in Example 17.
Figure 12:
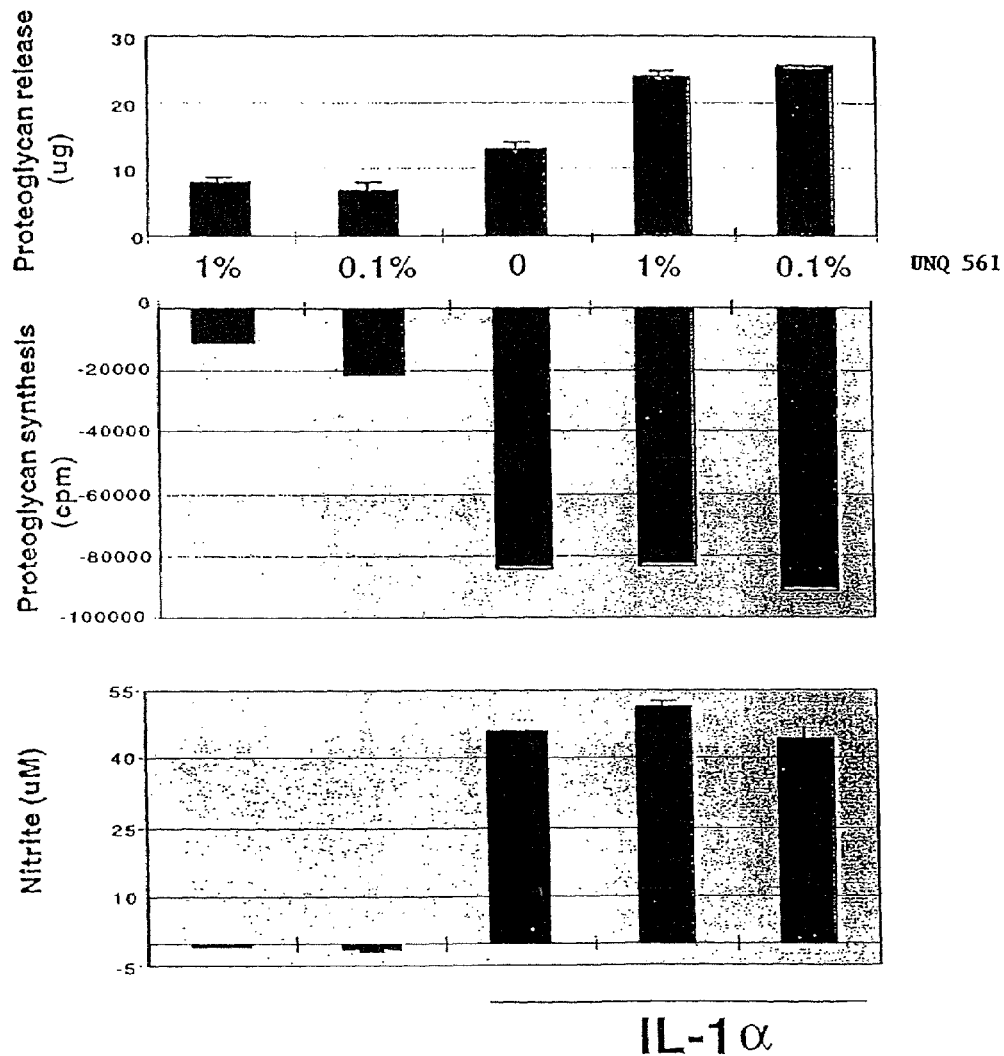
FIG. 12 shows the effect of UNQ561 (SEQ ID NO:3) on articular cartilage. Explants were treated with UNQ561 at 1% or 0.1% in the absence (leftmost three columns) or presence (rightmost three columns) of IL-1α (+) (10 ng/ml) (SEQ ID NO:25). Proteoglycan (PG) release and synthesis are shown as amount above control.

The IL-17R ECD (SEQ ID NO:15 migrated as a 60 kDa band when purified via its histidine tag (FIG. 11A, lane 1). Furthermore, the IL-17R ECD (SEQ ID NO:15 also precipitated in combination with IL-17 (SEQ ID NO:11) (lane 3). However, both IL-17B (SEQ ID NO:1) and IL-17C (SEQ ID NO:3) failed to compete for the binding of IL-17 (SEQ ID NO:11) for the labeled IL-17 receptor ECD (SEQ ID NO:15 (FIG. 11B, lane 15 and 16).

Example 13

Fluorescence-Activated Cell Sorter (FACS) Analysis of Binding to THP-1 Cells

THP-1 cells (5×105) were pre-incubated in PBS containing 5% horse serum at 4° C. for 30 minutes to block non-specific binding. IL-17 (SEQ ID NO:11), IL-17B.fc (SEQ ID NO:12), IL-17C.Fc (SEQ ID NO:13), or control Fc (1 μg each) were added and incubated with the THP-1 cells in a volume of 0.25 ml on ice for 1 hour. For the IL-17 binding experiment, primary anti hIL-17 antibody (1:100 dilution) and secondary goat anti-mouse antibody conjugated to FITC (Jackson Immunology Lab, 1:100 dilution) were added sequentially with 30-60 minutes incubation and extensive washes before each addition. For the Fc fusion proteins, the cells were stained with FITC conjugated goat anti-human IgG (Fc specific, Jackson Immunology Lab, 1:100 dilution). After thorough washes, a minimum of 5,000 cells were analyzed using a FACScan (Becton Dickinson).

The resulting of the above procedure was that both IL-17B (SEQ ID NO:12) and IL-17C (SEQ ID NO:13) Fc fusion proteins displayed binding to THP-1 cells compared with a control Fc fusion protein (FIG. 13).

Example 14

Purification of PRO1031 or PRO1122 Polypeptides Using Specific Antibodies

Native or recombinant PRO1031 or PRO1122 polypeptides may be purified by a variety of standard techniques in the art of protein purification. For example, pro-PRO1031 or pro-PRO1122 polypeptide, mature PRO1031 or PRO1122 polypeptide, or pre-PRO1031 or pre-PRO1122 polypeptide is purified by immunoaffinity chromatography using antibodies specific for the PRO1031 or PRO1122 polypeptide of interest. In general, an immunoaffinity column is constructed by covalently coupling the anti-PRO1031 or anti-PRO1122 antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE® (Pharacia LKB Biotechnology). The antibody is coupled to the resin, the resin is blocked, and the derivative resin is washed according to the manufacturer's instructions.

Such an immunoaffinity column is utilized in the purification of PRO1031 or PRO1122 polypeptide by preparing a fraction of cells containing PRO1031 or PRO1122 polypeptide in a soluble form. This preparation is derived by solubilization of the whole cell or of a subcellular fraction obtained via differential centrifugation by the addition of detergent or by other methods well known in the art. Alternatively, soluble PRO1031 or PRO1122 polypeptide containing a signal sequence may be secreted in useful quantity into the medium in which the cells are grown.

A soluble PRO1031 or PRO1122 polypeptide-containing preparation is passed over the immunoaffinity column, the and column is washed under conditions that allow the preferential absorbance of PRO1031 or PRO1122 polypeptide (e.g., high ionic strength buffers in the presence of detergent). Then, the column is eluted under conditions that disrupt antibody-PRO1031 or —PRO1122 polypeptide binding (e.g., a low pH buffer such as approximately pH 2-3, or a high concentration of a chaotrope such as urea or thiocyanate ion), and PRO1031 or PRO122 polypeptide is collected.

Example 15

Drug Screening

This invention is particularly useful for screening compounds by using PRO1031 or PRO1122 polypeptides or binding fragments thereof in any of a variety of drug screening techniques. The PRO1031 or PRO1122 polypeptide or fragment employed in such a test may either bye free in solution, affixed to a solid support, borne on a cell surface, or located intracellularly. One method of drug screening utilized eukaryotic or prokaryotic host cells which are stably transformed with recombinant nucleic acids expressing the PRO1031 or PRO1122 polypeptide or fragment. Drugs are screened against such transformed cells in competitive binding assays. Such cells, either in viable or fixed form, can be used for standard binding assays. On may measure, for example, the formation of complexes between PRO1031 or PRO1122 polypeptide or a fragment and the agent being tested. Alternatively, one can examine the diminution in complex formation between the PRO1031 or PRO1122 polypeptide and its target cell or target receptors caused by the agent being tested.

Thus, the present invention provides methods of screening for drugs or any other agents which can affect a PRO1031 or PRO1122 polypeptide-associated disease or disorder. These methods comprise contacting such an agent with a PRO1031 or PRO1122 polypeptide or fragment thereof and assaying (i) for the presence of a complex between the agent and the PRO1031 or PRO1122 polypeptide or fragment, or (ii) for the presence of a complex between the PRO1031 or PRO1122 polypeptide or fragment and the cell, by methods well known in the art. In such competitive binding assays, the PRO1031 or PRO1122 polypeptide or fragment is typically labeled. After suitable incubation, free PRO1031 or PRO1122 polypeptide or fragment is separated from that present in bound form, and the amount of free or uncomplexed label is a measure of the ability of the particular agent to bind to PRO1031 or PRO1122 or to interfere with the PRO1031 or PRO1122 polypeptide/cell complex.

Another technique for drug screening provide high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO1031 or PRO1122 polypeptide, the peptide test compounds are reacted with PRO1031 or PRO1122 polypeptide and washed. Bound PRO1031 or PRO1122 is detected by methods well known in the art. Purified PRO1031 or PRO1122 polypeptide can also be coated directly onto plates for use in the aforementioned drug screening techniques. In addition, non-neutralizing antibodies can by used to capture the peptide and immobilize it on the solid support.

This invention also contemplates the use of competitive drug screening assays in which neutralizing antibodies capable of binding PRO1031 or PRO1122 polypeptide specifically compete with a test compound for binding to PRO1031 or PRO1122 polypeptide or fragments thereof. In this manner, the antibodies can be used to detect the presence of any peptide which shares one or more antigenic determinants with PRO1031 or PRO1122 polypeptide.

Example 16

Rational Drug Design

The goal of rational drug design is to produce structural analogs of biologically active polypeptide of interest (i.e., a PRO1031 or PRO1122 polypeptide) or of small molecules with which they interact, e.g., agonists, antagonists, or inhibitors. Any of these examples can be used to fashion drugs which are more active or stable forms of the PRO1031 or PRO11222 polypeptide or which enhance or interfere with the function of the PRO1031 or PRO122 polypeptide in vivo. (c.f., Hodgson, *Bio/Technology* 9: 19-21 (1991)).

In one approach, the three-dimensional structure of the PRO1031 or PRO1122 polypeptide, or of a PRO1031 or PRO1122 polypeptide-inhibitor complex, is determined by x-ray cystallography, by computer modeling or, most typically, by a combination of the two approaches. Both the shape and charges of the PRO1031 or PRO1122 must be ascertained to elucidate the structure and to determine active sties(s) of the molecule. Less often, useful information regarding the structure of the PRO1031 or PRO1122 may be gained by modeling based on the structure of homologous proteins. In both cases, relevant structural information is used to design analogous PRO1031 or PRO1122 polypeptide-like molecules or to identity efficient inhibitors. Useful examples of rational drug design may include molecules which have improved activity or stability as shown by Braxton and Wells, Biochemistry 31: 7796-7801 (1992) or which act as inhibitors, agonists, or antagonists of native peptides as shown by Athauda et al., *J. Biochem.* 113: 742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein cystallography altogether by generating anti-idiotypic antibodies (anti-ids) to a functional, pharmacologically active antibody. As a mirror image of a mirror image, the binding site of anti anti-ids would be expected to be an analog of the original receptor. The anti-id could then by used to identify and isolate peptides from banks of chemically or biologically produced peptides. The isolated peptides would then act as the pharmacore.

By virtue of the present invention, sufficient amounts of the PRO1031 or PRO1122 polypeptide may be made available to perform such analytical studies as X-ray crystallography. In addition, knowledge of the PRO1031 or PRO1122 polypeptide amino acid sequence provided herein will provide guidance to those employing computer modeling techniques in place or in addition to x-ray crystallography.

Example 17

Articular Cartilage Explant Assay

Introduction:

As mentioned previously, IL-17 is likely to play a role in the initiation or maintenance of the proinflammatory response. IL-17 is a cytokine expressed by CD4$^+$ T$_h$ cells and induces the secretion of proinflammatory and hematopoietic cytokines (e.g., IL-1β, TNF-α, IL-6, IL-8, GM-CSF. Aarvak et al., *J. Immunol* 162: 1246-1251 (1999); Fossiez et al, *J. Exp. Med.* 183: 2593-2603 (1996); Jovanovic et al, *J. Immunol.* 160: 3513-3521 (1998) in a number of cell types including synoviocytes and macrophages. In the presence of IL-17, fibroblasts sustain sustain the proliferation of CD34+ hematopoietic progenitors and induce their preferential maturation into neutrophils. As a result, I1-17 may constitute an early initiator of the T cell-dependent inflammatory reaction and be part of the cytokine network which bridges the immune system to hematopoiesis.

Expression of IL-17 has been found in the synovium of patients with rheumatoid arthritis, psoriatic arthritis, or osteoarthritis, but not in normal joint tissues. IL-17 can synergize with the monocyte-derived, proinflammatory cytokines IL-1β or TNF-α to induce IL-6 and GM-CSF. By acting directly on synoviocytes, IL-17 could enhance secretion of proinflammatory cytokines in vivo and thus exacerbate joint inflammation and destruction.

To further understand the possible role of IL-17, Applicants have tested the effects of IL-17 on cartilage matrix metabolism. In light of the known catabolic effects of nitric oxide (NO) on cartilage, and the existence of high levels of NO in arthritic joints, NO production was also measured.

Methods:

Articular cartilage explants: The metacarpophalangeal joint of a 4-6 month old female pigs was aseptically dissected, and articular cartilage is removed by free-hand slicing in a careful manner so as to avoid the underlying bone. The cartilage was minced and cultured in bulk for at least 24 hours in a humidified atmosphere of 95% air 5% $CO_2$ in serum free (SF) media (DME/F12 1:1) with 0.1% BSA and antibiotics. After washing three times, approximately 80 mg of articular cartilage was aliquoted into micronics tubes and incubated for at least 24 hours in the above SF media. Test proteins were then added at 1% either alone or in combination with IL-1α (10 ng/ml) (SEQ ID NO:25). Media was harvested and changed at various timepoints (0, 24, 48, 72 hours) and assayed for proteoglycan content using the 1,9-dimethyl-methylene blue (DMB) colorimetric assay described in Farndale and Buttle, *Biochem. Biophys. Acta* 883: 173-177 (1985). After labeling (overnight) with $^{35}$S-sulfur, the tubes were weighed to determine the amount of tissue. Following an overnight digestion, the amount of proteoglycan remaining in the tissue as well as proteoglycan synthesis ($^{35}$S-incorporation) is determined.

Measurement of NO production: The assay is based on the principle that 2,3-diaminonapthalene (DAN) reacts with nitrite under acidic conditions to form 1-(H)-naphthotriazole, a flourescent product. As NO is quickly metabolized into nitrite ($NO_2^{-1}$) and nitrate ($NO_3^{-1}$), detection of nitrite, is one means of detecting (albeit undercounting) the actual NO produced. 10 μL of DAN (0.05 mg. mL in 0.62M HCl) is added to 100 μL of sample (cell culture supernatant), mixed, and incubated at room temperature for 10-20 minutes. Reaction is terminated with 5 mL of 2.8N NaOH. Formation of 2,3-diaminonaphthotriazole was measured using a Cytoflor flourescent plate reader with excitation at 360 nm and emission read at 450 nm. For optimal measurement of flourescent intensity, black plates with clear bottoms were used.

Figure 7:
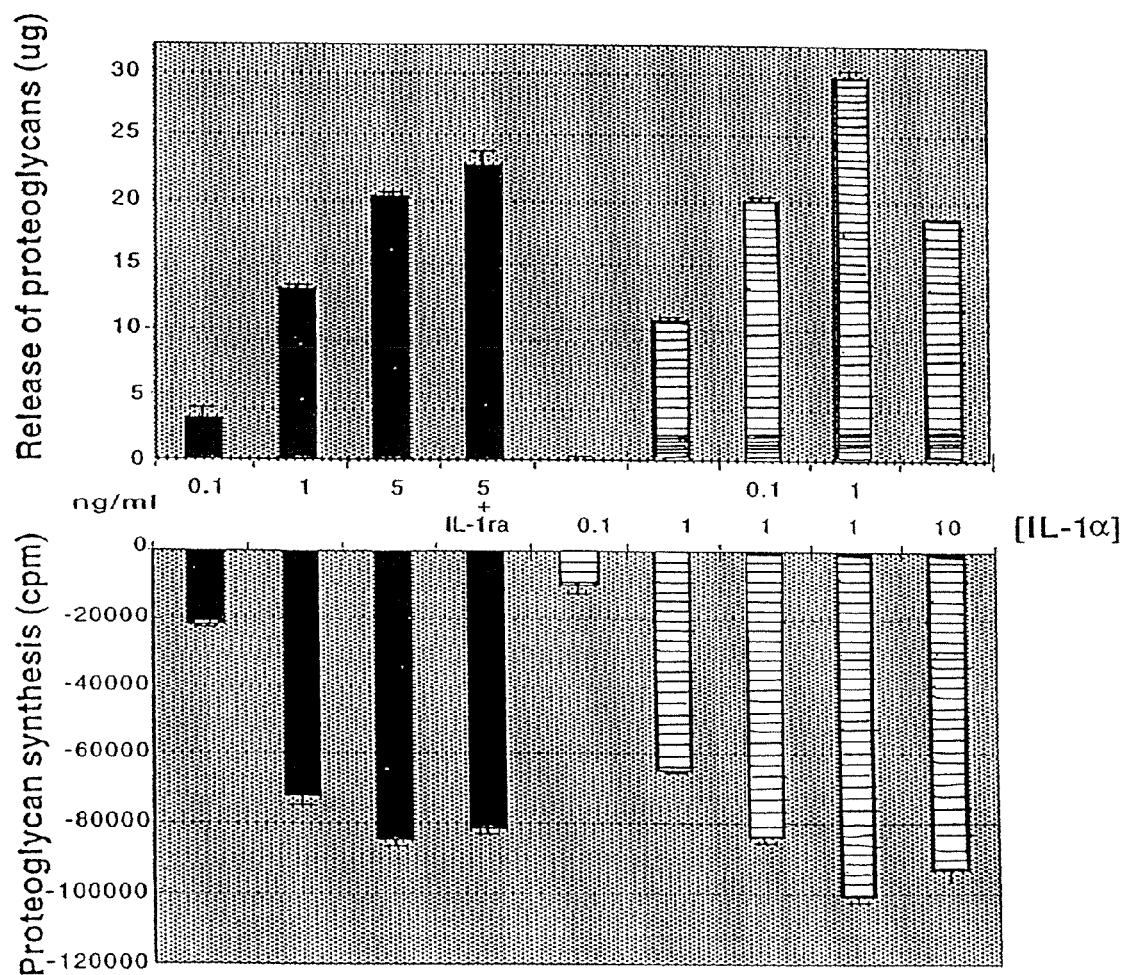
FIG. 7 shows the effect of IL-17 (SEQ ID NO:11) on articular cartilage. Cartilage explants were cultured with the indicated concentration of IL-17 alone (solid) or in the presence of IL-1α at the indicated concentration (hatched) (SEQ ID NO:25) or IL1ra (IL-1 receptor antagonist, R&D Systems, 1 µg/ml) (SEQ ID NO:26) for 72 hours. Release of proteolycans (PG) into the media (top panel) indicates matrix breakdown. Matrix synthesis was determined by incorporation of $^{35}$S-sulphate into the tissue (bottom panel).
Figure 8:
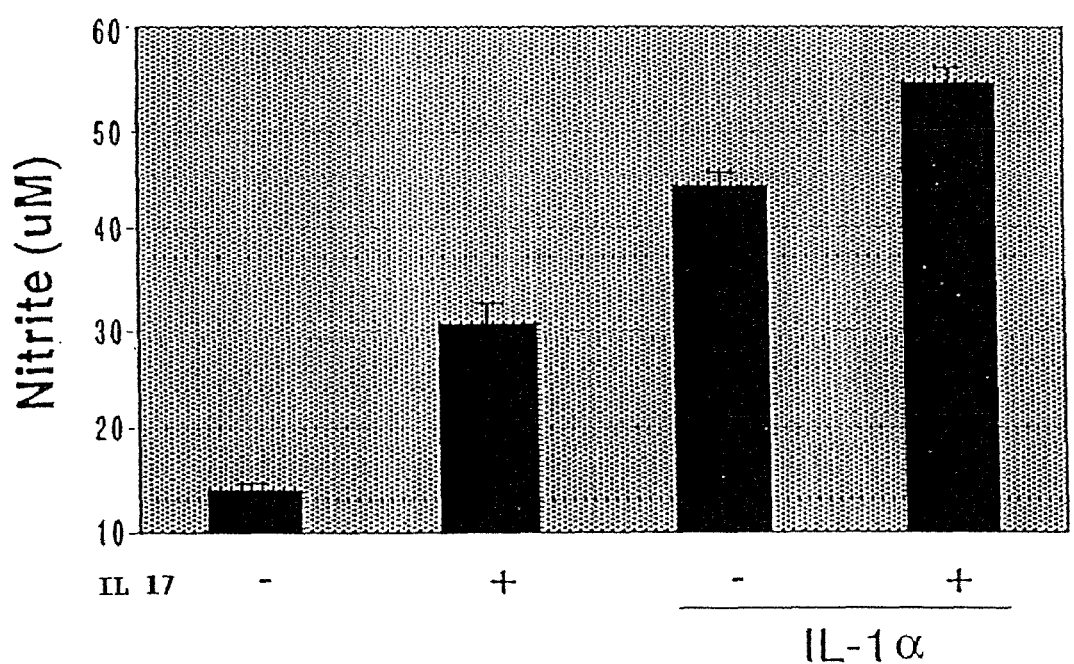
FIG. 8 shows the effect of IL-17 (SEQ ID NO:11) on the release of nitric oxide. Explants were treated with IL-17 (10 ng/ml) alone (left columns) or in the presence of IL-1α (10 ng/ml) (SEQ ID NO:25) (right columns). After 48 hours, media was assayed for nitrite concentration.
Figure 10:
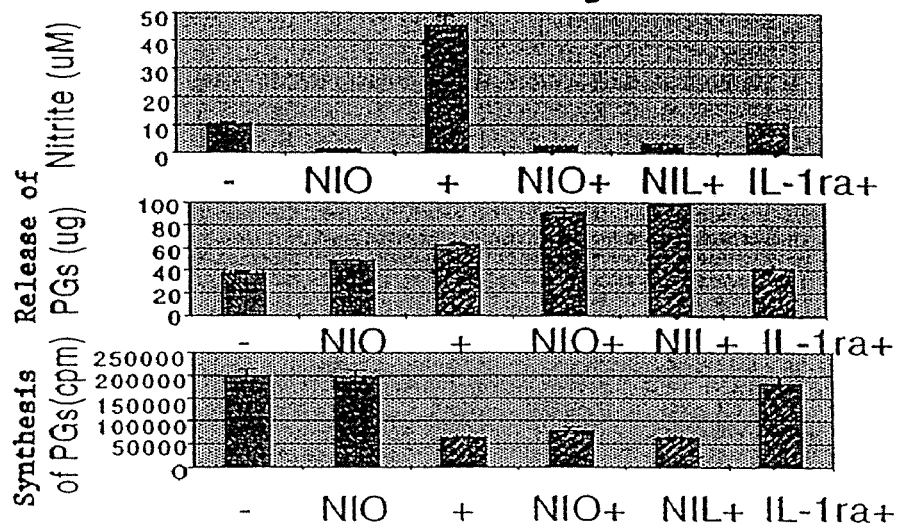
FIG. 10 shows the effect of the inhibition of NO on IL-1α-induced changes in proteoglycan (PG) metabolism. Articular cartilage explants were treated with IL-1α (5 ng/ml) (SEQ ID NO:25) alone (+) or with inhibitors of NOS (L-NIO or L-NIL) (L-NIL, reversible NOS inhibitor, Caymen Chemical) or IL-Ira (IL-1 receptor antagonist, R&D Systems, 1 µg/ml) (SEQ ID NO:26). After 72 hours or treatment, media as assayed for (A) nitrite concentration and (B) amount of proteoglycans. (C) Matrix synthesis was determined by incorporation of $^{35}$S-sulphate into the tissue.

Results and Discussion:

IL-17 (SEQ ID NO:11) was observed to both increase the release of and decrease the synthesis of proteoglycans (FIG. 7). Moreover, this effect was additive to the effect observed from IL-1α. (SEQ ID NO:25). The effects of IL-17 are not mediated by the production of nitric oxide, nor does inhibition of nitric oxide release augment matrix breakdown. UNQ561 (SEQ ID NO:3) increases matrix breakdown and inhibits matrix synthesis. Thus, expression of PRO1122 is likely to be associated with degenerative cartilagenous disorders. On the other hand, UNQ516 (SEQ ID NO:1) increases matrix synthesis and inhibits nitric oxide release by articular cartilage explants.

In conclusion, IL-17 likely contributes to loss of articular cartilage in arthritic joints, and thus inhibition of its activity might limit inflammation and cartilage destruction. IL-1 and IL-17 have similar yet distinct activities, due to their use of different receptors and overlapping downstream signaling mechanisms.

Given the findings of the potent catabolic effects of IL-17 on articular cartilage explants and the homology of UNQ516 and UNQ561 to IL-17, antagonists to any or all of these proteins may be useful for the treatment of inflammatory conditions and cartilage defects such as arthritis. However, our finding that UNQ 516 inhibits NO production and enhances matrix synthesis suggests that this protein and agonists thereof could have beneficial effects within the joint and may thus, in and of itself, be useful for the treatment of the above mentioned disorders.

Finally, it is well known that growth factors can have biphasic effects and that diseased tissue can respond differently than normal tissue to a given factor in vivo. For these reasons, antagonists or agonists (e.g. the proteins themselves) of UNQ 516, UNQ 561, or IL-17, may be useful for the treatment of inflammatory conditions and joint disorders such as arthritis.

Deposit of Material

The following materials have been deposited with the American Type Culture Collection, 10801 University Boulevard, Manassas, Va. USA 20110-2209 (ATCC):

| Material | ATCC Dep. No. | Deposit Date |
|---|---|---|
| DNA59294-1381 | 209866 | 14 May 1998 |
| DNA62377-1381-1 | 203552 | 22 Dec. 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated antibody that binds the polypeptide of SEQ ID NO:3.

2. The isolated antibody of claim 1 that binds the polypeptide of SEQ ID NO:3 lacking its associated signal peptide.

3. The isolated antibody of claim 1 which is a monoclonal antibody.

4. The isolated antibody of claim 1 which is a humanized antibody.

5. The isolated antibody of claim 1 which is a human antibody.

6. The isolated antibody of claim 1 which is a chimeric antibody.

7. The isolated antibody of claim 1 which is a single chain antibody.

8. The isolated antibody of claim 1 which is an antibody fragment.

9. The isolated antibody of claim 1 which is labeled with a detectable moiety capable of directly or indirectly producing a signal.

10. A pharmaceutical composition comprising the isolated antibody of claim 1 and a pharmaceutically acceptable carrier.

11. An isolated antibody that binds the mature polypeptide of SEQ ID NO:3 consisting of amino acid residues 19-197 of SEQ ID NO:3.

12. The isolated antibody of claim 11 which is a monoclonal antibody.

13. The isolated antibody of claim 11 which is a humanized antibody.

14. The isolated antibody of claim 11 which is a human antibody.

15. The isolated antibody of claim 11 which is a chimeric antibody.

16. The isolated antibody of claim 11 which is a single chain antibody.

17. The isolated antibody of claim 11 which is an antibody fragment.

18. The isolated antibody of claim 11 which is labeled with a detectable moiety capable of directly or indirectly producing a signal.

19. A pharmaceutical composition comprising the isolated antibody of claim 11 and a pharmaceutically acceptable carrier.

20. An isolated antibody that binds the polypeptide encoded by the cDNA clone deposited as ATCC deposit number 203552.

21. The isolated antibody of claim 20 which is a monoclonal antibody.

22. The isolated antibody of claim 20 which is a humanized antibody.

23. The isolated antibody of claim 20 which is a human antibody.

24. The isolated antibody of claim 20 which is a chimeric antibody.

25. The isolated antibody of claim 20 which is a single chain antibody.

26. The isolated antibody of claim 20 which is an antibody fragment.

27. The isolated antibody of claim 20 which is labeled with a detectable moiety capable of directly or indirectly producing a signal.

28. A pharmaceutical composition comprising the isolated antibody of claim 20 and a pharmaceutically acceptable carrier.

* * * * *

SEQUENCE LISTING

```
<160> NUMBER OF SEQ ID NOS: 26

<210> SEQ ID NO 1
<211> LENGTH: 180
<212> TYPE: PRT
<213> ORGANISM: Homo sapiens

<400> SEQUENCE: 1

Met Asp Trp Pro His Asn Leu Leu Phe Leu Leu Thr Ile Ser Ile
 1               5                  10                  15

Phe Leu Gly Leu Gly Gln Pro Arg Ser Pro Lys Ser Lys Arg Lys
                20                  25                  30

Gly Gln Gly Arg Pro Gly Pro Leu Ala Pro Gly Pro His Gln Val
                35                  40                  45

Pro Leu Asp Leu Val Ser Arg Met Lys Pro Tyr Ala Arg Met Glu
                50                  55                  60

Glu Tyr Glu Arg Asn Ile Glu Glu Met Val Ala Gln Leu Arg Asn
                65                  70                  75

Ser Ser Glu Leu Ala Gln Arg Lys Cys Glu Val Asn Leu Gln Leu
                80                  85                  90

Trp Met Ser Asn Lys Arg Ser Leu Ser Pro Trp Gly Tyr Ser Ile
                95                  100                 105

Asn His Asp Pro Ser Arg Ile Pro Val Asp Leu Pro Glu Ala Arg
                110                 115                 120

Cys Leu Cys Leu Gly Cys Val Asn Pro Phe Thr Met Gln Glu Asp
                125                 130                 135

Arg Ser Met Val Ser Val Pro Val Phe Ser Gln Val Pro Val Arg
                140                 145                 150

Arg Arg Leu Cys Pro Pro Pro Pro Arg Thr Gly Pro Cys Arg Gln
```

```
                            155                 160                 165
        Arg Ala Val Met Glu Thr Ile Ala Val Gly Cys Thr Cys Ile Phe
                        170                 175                 180

<210> SEQ ID NO 2
<211> LENGTH: 687
<212> TYPE: DNA
<213> ORGANISM: Homo sapiens

<400> SEQUENCE: 2
aggcgggcag cagctgcagg ctgaccttgc agcttggcgg aatggactgg            50
cctcacaacc tgctgtttct tcttaccatt tccatcttcc tggggctggg           100
ccagcccagg agccccaaaa gcaagaggaa ggggcaaggg cggcctgggc           150
ccctggcccc tggccctcac caggtgccac tggacctggt gtcacggatg           200
aaaccgtatg cccgcatgga ggagtatgag aggaacatcg aggagatggt           250
ggcccagctg aggaacagct cagagctggc ccagagaaag tgtgaggtca           300
acttgcagct gtggatgtcc aacaagagga gcctgtctcc ctggggctac           350
agcatcaacc acgacccag ccgtatcccc gtggacctgc cggaggcacg            400
gtgcctgtgt ctgggctgtg tgaacccctt caccatgcag gaggaccgca           450
gcatggtgag cgtgccggtg ttcagccagg ttcctgtgcg ccgccgcctc           500
tgcccgccac cgccccgcac agggccttgc cgccagcgcg cagtcatgga           550
gaccatcgct gtgggctgca cctgcatctt ctgaatcacc tggcccagaa           600
gccaggccag cagcccgaga ccatcctcct tgcacctttg tgccaagaaa           650
ggcctatgaa aagtaaacac tgacttttga aagcaag                         687

<210> SEQ ID NO 3
<211> LENGTH: 197
<212> TYPE: PRT
<213> ORGANISM: Homo sapiens

<400> SEQUENCE: 3

Met Thr Leu Leu Pro Gly Leu Leu Phe Leu Thr Trp Leu His Thr
  1               5                  10                  15

Cys Leu Ala His His Asp Pro Ser Leu Arg Gly His Pro His Ser
                 20                  25                  30

His Gly Thr Pro His Cys Tyr Ser Ala Glu Glu Leu Pro Leu Gly
                 35                  40                  45

Gln Ala Pro Pro His Leu Leu Ala Arg Gly Ala Lys Trp Gly Gln
                 50                  55                  60

Ala Leu Pro Val Ala Leu Val Ser Ser Leu Glu Ala Ala Ser His
                 65                  70                  75

Arg Gly Arg His Glu Arg Pro Ser Ala Thr Thr Gln Cys Pro Val
                 80                  85                  90

Leu Arg Pro Glu Glu Val Leu Glu Ala Asp Thr His Gln Arg Ser
                 95                 100                 105

Ile Ser Pro Trp Arg Tyr Arg Val Asp Thr Asp Glu Asp Arg Tyr
                110                 115                 120

Pro Gln Lys Leu Ala Phe Ala Glu Cys Leu Cys Arg Gly Cys Ile
                125                 130                 135

Asp Ala Arg Thr Gly Arg Glu Thr Ala Ala Leu Asn Ser Val Arg
                140                 145                 150
```

```
Leu Leu Gln Ser Leu Leu Val Leu Arg Arg Arg Pro Cys Ser Arg
                155                 160                 165

Asp Gly Ser Gly Leu Pro Thr Pro Gly Ala Phe Ala Phe His Thr
            170                 175                 180

Glu Phe Ile His Val Pro Val Gly Cys Thr Cys Val Leu Pro Arg
            185                 190                 195

Ser Val

<210> SEQ ID NO 4
<211> LENGTH: 1047
<212> TYPE: DNA
<213> ORGANISM: Homo sapiens

<400> SEQUENCE: 4
gccaggtgtg caggccgctc aagcccagc ctgccccgct gccgccacca              50
tgacgctcct ccccggcctc ctgtttctga cctggctgca cacatgcctg            100
gcccaccatg acccctccct caggggcac ccccacagtc acggtacccc             150
acactgctac tcggctgagg aactgcccct cggccaggcc ccccacacc             200 tgctggctcg aggtgccaag tggggcagg ctttgcctgt agccctggtg             250
tccagcctgg aggcagcaag ccacaggggg aggcacgaga ggccctcagc            300
tacgacccag tgcccggtgc tgcggccgga ggaggtgttg gaggcagaca            350
cccaccagcg ctccatctca ccctggagat accgtgtgga cacggatgag            400
gaccgctatc cacagaagct ggccttcgcc gagtgcctgt gcagaggctg            450
tatcgatgca cggacgggcc gcgagacagc tgcgctcaac tccgtgcggc            500
tgctccagag cctgctggtg ctgcgccgcc ggccctgctc ccgcgacggc            550
tcggggctcc ccacacctgg ggcctttgcc ttccacaccg agttcatcca            600
cgtccccgtc ggctgcacct gcgtgctgcc ccgttcagtg tgaccgccga            650
ggccgtgggg cccctagact ggacacgtgt gctccccaga gggcaccccc            700
tatttatgtg tatttattgt tatttatatg cctcccccaa cactacccct            750
ggggtctggg cattccccgt gtctggagga cagccccca ctgttctcct             800 catctccagc ctcagtagtt gggggtagaa ggagctcagc acctcttcca            850
gcccttaaag ctgcagaaaa ggtgtcacac ggctgcctgt accttggctc            900
cctgtcctgc tccggcttc ccttacccta tcactggcct caggccccgc             950
aggctgcctc ttcccaacct ccttggaagt accctgtttt cttaaacaat           1000
tatttaagtg tacgtgtatt attaaactga tgaacacatc cccaaaa              1047

<210> SEQ ID NO 5
<211> LENGTH: 830
<212> TYPE: DNA
<213> ORGANISM: Homo sapiens
<220> FEATURE:
<221> NAME/KEY: unsure
<222> LOCATION: 105-115
<223> OTHER INFORMATION: unknown base

<400> SEQUENCE: 5
ggcagcaggg accaagagag gcacgcttgc cctttatga catcagagct              50 cctggttctt gctccttggg actctgggac ttacaccagt ggcaccctg             100 gctcnnnnnn nnnnnaattc ggtacgaggc tggggttcag gcgggcagca            150
```

| | |
|---|---|
| gctgcaggct gaccttgcag cttggcggaa tggactggcc tcacaacctg | 200 |
| ctgtttcttc ttaccatttc catcttcctg gggctgggcc agcccaggag | 250 |
| ccccaaaagc aagaggaagg ggcaagggcg gcctgggccc ctggtccctg | 300 |
| gccctcacca ggtgccactg gacctggtgt cacggatgaa accgtatgcc | 350 |
| cgcatggagg agtatgagag gaacatcgag gagatgttgg cccagctgag | 400 |
| gaacagttca gagctggccc agagaaagtg tgaggtcaac ttgcagctgt | 450 |
| ggatgtccaa caagaggagc ctgtctccct ggggctacag catcaaccac | 500 |
| gaccccagcc gtatcccgt ggacctccgg aggcacggtg cctgtgtctg | 550 |
| ggcttgtgtg aaccccttca ccatgcagga ggaccgcagc atggtgagcg | 600 |
| tgccggtgtt cagccaggtt cctgtgcgcc gccgcctctg cccgccaccg | 650 |
| ccccgcacag ggccttgccg ccagcgcgca gtcatggaga ccatcgctgt | 700 |
| gggctgcacc tgcatcttct gaatcgacct ggcccagaag ccaggccagc | 750 |
| agcccgagac catcctcctt gcacctttgt gccaagaaag gcctatgaaa | 800 |
| agtaaacact gacttttgaa agcaaaaaaa | 830 |

<210> SEQ ID NO 6
<211> LENGTH: 397
<212> TYPE: DNA
<213> ORGANISM: Homo sapiens
<220> FEATURE:
<221> NAME/KEY: unsure
<222> LOCATION: 10, 150, 267
<223> OTHER INFORMATION: unknown base

<400> SEQUENCE: 6

| | |
|---|---|
| aggcgggcan agctgcaggc tgaccttgca gcttggcgga atggactggc | 50 |
| ctcacaacct gctgtttctt cttaccattt ccatcttcct ggggctgggc | 100 |
| agccaggagc cccaaaagca agaggaaggg gcaagggcgg cctgggcccn | 150 |
| tggcctggcc tcaccaggtg ccactggacc tggtgtcacg gatgaaaccg | 200 |
| tatgcccgca tggaggagta tgagaggaac atcgaggaga tggtggccca | 250 |
| gctgaggaac agctcanaag ctggcccaga gaaagtgtga ggtcaacttg | 300 |
| cagctgtgga tgtccaacaa gaggagcct gtctcccttg gggctacaag | 350 |
| catcaaccac gaccccagcc gtatccccg tgggaccttg ccgggac | 397 |

<210> SEQ ID NO 7
<211> LENGTH: 230
<212> TYPE: DNA
<213> ORGANISM: Homo sapiens

<400> SEQUENCE: 7

| | |
|---|---|
| cacggatgag gaccgctatc cacagaagct ggccttcgcc gagtgcctgt | 50 |
| gcagaggctg tatcgatgca cggacgggcc gcgagacagc tgcgctcaac | 100 |
| tccgtgcggc tgctccagag cctgctgtg ctgcgccgcc ggccctgctc | 150 |
| ccgcgacggc tcggggctcc ccacacctgg ggcctttgcc ttccacaccg | 200 |
| agttcatcca cgtccccgtc ggctgcacct | 230 |

<210> SEQ ID NO 8
<211> LENGTH: 24
<212> TYPE: DNA
<213> ORGANISM: Artificial sequence -continued

```
<220> FEATURE:
<223> OTHER INFORMATION: Forward PCR primer

<400> SEQUENCE: 8
atccacagaa gctggccttc gccg                                              24

<210> SEQ ID NO 9
<211> LENGTH: 24
<212> TYPE: DNA
<213> ORGANISM: Artificial sequence
<220> FEATURE:
<223> OTHER INFORMATION: reverse PCR primer

<400> SEQUENCE: 9
gggacgtgga tgaactcggt gtgg                                              24

<210> SEQ ID NO 10
<211> LENGTH: 40
<212> TYPE: DNA
<213> ORGANISM: Artificial sequence
<220> FEATURE:
<223> OTHER INFORMATION: hybridization probe

<400> SEQUENCE: 10
tatccacaga agctggcctt cgccgagtgc ctgtgcagag                             40

<210> SEQ ID NO 11
<211> LENGTH: 155
<212> TYPE: PRT
<213> ORGANISM: Homo sapiens

<400> SEQUENCE: 11
```

Met Thr Pro Gly Lys Thr Ser Leu Val Ser Leu Leu Leu Leu Leu
 1               5                  10                  15

Ser Leu Glu Ala Ile Val Lys Ala Gly Ile Thr Ile Pro Arg Asn
             20                  25                  30

Pro Gly Cys Pro Asn Ser Glu Asp Lys Asn Phe Pro Arg Thr Val
             35                  40                  45

Met Val Asn Leu Asn Ile His Asn Arg Asn Thr Asn Thr Asn Pro
             50                  55                  60

Lys Arg Ser Ser Asp Tyr Tyr Asn Arg Ser Thr Ser Pro Trp Asn
             65                  70                  75

Leu His Arg Asn Glu Asp Pro Glu Arg Tyr Pro Ser Val Ile Trp
             80                  85                  90

Glu Ala Lys Cys Arg His Leu Gly Cys Ile Asn Ala Asp Gly Asn
             95                 100                 105

Val Asp Tyr His Met Asn Ser Val Pro Ile Gln Gln Glu Ile Leu
            110                 115                 120

Val Leu Arg Arg Glu Pro Pro His Cys Pro Asn Ser Phe Arg Leu
            125                 130                 135

Glu Lys Ile Leu Val Ser Val Gly Cys Thr Cys Val Thr Pro Ile
            140                 145                 150

Val His His Val Ala
            155

```
<210> SEQ ID NO 12
<211> LENGTH: 408
<212> TYPE: PRT
<213> ORGANISM: Artificial Sequence
<220> FEATURE:
<223> OTHER INFORMATION: IL17B-Fc fusion
```

<400> SEQUENCE: 12

```
Met Asp Trp Pro His Asn Leu Leu Phe Leu Leu Thr Ile Ser Ile
  1               5                  10                  15

Phe Leu Gly Leu Gly Gln Pro Arg Ser Pro Lys Ser Lys Arg Lys
                 20                  25                  30

Gly Gln Gly Arg Pro Gly Pro Leu Ala Pro Gly Pro His Gln Val
                 35                  40                  45

Pro Leu Asp Leu Val Ser Arg Met Lys Pro Tyr Ala Arg Met Glu
                 50                  55                  60

Glu Tyr Glu Arg Asn Ile Glu Glu Met Val Ala Gln Leu Arg Asn
                 65                  70                  75

Ser Ser Glu Leu Ala Gln Arg Lys Cys Glu Val Asn Leu Gln Leu
                 80                  85                  90

Trp Met Ser Asn Lys Arg Ser Leu Ser Pro Trp Gly Tyr Ser Ile
                 95                 100                 105

Asn His Asp Pro Ser Arg Ile Pro Val Asp Leu Pro Glu Ala Arg
                110                 115                 120

Cys Leu Cys Leu Gly Cys Val Asn Pro Phe Thr Met Gln Glu Asp
                125                 130                 135

Arg Ser Met Val Ser Val Pro Val Phe Ser Gln Val Pro Val Arg
                140                 145                 150

Arg Arg Leu Cys Pro Pro Pro Arg Thr Gly Pro Cys Arg Gln
                155                 160                 165

Arg Ala Val Met Glu Thr Ile Ala Val Gly Cys Thr Cys Ile Phe
                170                 175                 180

Pro Asp Lys Thr His Thr Cys Pro Pro Cys Pro Ala Pro Glu Leu
                185                 190                 195

Leu Gly Gly Pro Ser Val Phe Leu Phe Pro Pro Lys Pro Lys Asp
                200                 205                 210

Thr Leu Met Ile Ser Arg Thr Pro Glu Val Thr Cys Val Val Val
                215                 220                 225

Asp Val Ser His Glu Asp Pro Glu Val Lys Phe Asn Trp Tyr Val
                230                 235                 240

Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu
                260                 265                 270

His Gln Asp Trp Leu Asn Gly Lys Glu Tyr Lys Cys Lys Val Ser
                275                 280                 285

Asn Lys Ala Leu Pro Ala Pro Ile Glu Lys Thr Ile Ser Lys Ala
                290                 295                 300

Lys Gly Gln Pro Arg Glu Pro Gln Val Tyr Thr Leu Pro Pro Ser
                305                 310                 315

Arg Glu Glu Met Thr Lys Asn Gln Val Ser Leu Thr Cys Leu Val
                320                 325                 330

Lys Gly Phe Tyr Pro Ser Asp Ile Ala Val Glu Trp Glu Ser Asn
                335                 340                 345

Gly Gln Pro Glu Asn Asn Tyr Lys Thr Thr Pro Pro Val Leu Asp
                350                 355                 360

Ser Asp Gly Ser Phe Phe Leu Tyr Ser Lys Leu Thr Val Asp Lys
                365                 370                 375

Ser Arg Trp Gln Gln Gly Asn Val Phe Ser Cys Ser Val Met His
```

```
                      380                 385                 390
Glu Ala Leu His Asn His Tyr Thr Gln Lys Ser Leu Ser Leu Ser
                  395                 400                 405

Pro Gly Lys

<210> SEQ ID NO 13
<211> LENGTH: 425
<212> TYPE: PRT
<213> ORGANISM: Artificial Sequence
<220> FEATURE:
<223> OTHER INFORMATION: IL-17C-Fc fusion

<400> SEQUENCE: 13

Met Thr Leu Leu Pro Gly Leu Leu Phe Leu Thr Trp Leu His Thr
 1               5                  10                  15

Cys Leu Ala His His Asp Pro Ser Leu Arg Gly His Pro His Ser
                 20                  25                  30

His Gly Thr Pro His Cys Tyr Ser Ala Glu Glu Leu Pro Leu Gly
                 35                  40                  45

Gln Ala Pro Pro His Leu Leu Ala Arg Gly Ala Lys Trp Gly Gln
                 50                  55                  60

Ala Leu Pro Val Ala Leu Val Ser Ser Leu Glu Ala Ala Ser His
                 65                  70                  75

Arg Gly Arg His Glu Arg Pro Ser Ala Thr Thr Gln Cys Pro Val
                 80                  85                  90

Leu Arg Pro Glu Glu Val Leu Glu Ala Asp Thr His Gln Arg Ser
                 95                 100                 105

Ile Ser Pro Trp Arg Tyr Arg Val Asp Thr Asp Glu Asp Arg Tyr
                110                 115                 120

Pro Gln Lys Leu Ala Phe Ala Glu Cys Leu Cys Arg Gly Cys Ile
                125                 130                 135

Asp Ala Arg Thr Gly Arg Glu Thr Ala Ala Leu Asn Ser Val Arg
                140                 145                 150

Leu Leu Gln Ser Leu Leu Val Leu Arg Arg Arg Pro Cys Ser Arg
                155                 160                 165

Asp Gly Ser Gly Leu Pro Thr Pro Gly Ala Phe Ala Phe His Thr
                170                 175                 180

Glu Phe Ile His Val Pro Val Gly Cys Thr Cys Val Leu Pro Arg
                185                 190                 195

Ser Val Pro Asp Lys Thr His Thr Cys Pro Pro Cys Pro Ala Pro
                200                 205                 210

Glu Leu Leu Gly Gly Pro Ser Val Phe Leu Phe Pro Pro Lys Pro
                215                 220                 225

Lys Asp Thr Leu Met Ile Ser Arg Thr Pro Glu Val Thr Cys Val
                230                 235                 240

Val Val Asp Val Ser His Glu Asp Pro Glu Val Lys Phe Asn Trp
                245                 250                 255

Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr
                275                 280                 285

Val Leu His Gln Asp Trp Leu Asn Gly Lys Glu Tyr Lys Cys Lys
                290                 295                 300

Val Ser Asn Lys Ala Leu Pro Ala Pro Ile Glu Lys Thr Ile Ser
                305                 310                 315
```

```
Lys Ala Lys Gly Gln Pro Arg Glu Pro Gln Val Tyr Thr Leu Pro
                320                 325                 330

Pro Ser Arg Glu Glu Met Thr Lys Asn Gln Val Ser Leu Thr Cys
                335                 340                 345

Leu Val Lys Gly Phe Tyr Pro Ser Asp Ile Ala Val Glu Trp Glu
                350                 355                 360

Ser Asn Gly Gln Pro Glu Asn Asn Tyr Lys Thr Thr Pro Pro Val
                365                 370                 375

Leu Asp Ser Asp Gly Ser Phe Phe Leu Tyr Ser Lys Leu Thr Val
                380                 385                 390

Asp Lys Ser Arg Trp Gln Gln Gly Asn Val Phe Ser Cys Ser Val
                395                 400                 405

Met His Glu Ala Leu His Asn His Tyr Thr Gln Lys Ser Leu Ser
                410                 415                 420

Leu Ser Pro Gly Lys
                425

<210> SEQ ID NO 14
<211> LENGTH: 212
<212> TYPE: PRT
<213> ORGANISM: Homo sapiens

<400> SEQUENCE: 14

Met Asn Ser Phe Ser Thr Ser Ala Phe Gly Pro Val Ala Phe Ser
  1               5                  10                  15

Leu Gly Leu Leu Leu Val Leu Pro Ala Ala Phe Pro Ala Pro Val
                 20                  25                  30

Pro Pro Gly Glu Asp Ser Lys Asp Val Ala Ala Pro His Arg Gln
                 35                  40                  45

Pro Leu Thr Ser Ser Glu Arg Ile Asp Lys Gln Ile Arg Tyr Ile
                 50                  55                  60

Leu Asp Gly Ile Ser Ala Leu Arg Lys Glu Thr Cys Asn Lys Ser
                 65                  70                  75

Asn Met Cys Glu Ser Ser Lys Glu Ala Leu Ala Glu Asn Asn Leu
                 80                  85                  90

Asn Leu Pro Lys Met Ala Glu Lys Asp Gly Cys Phe Gln Ser Gly
                 95                 100                 105

Phe Asn Glu Glu Thr Cys Leu Val Lys Ile Ile Thr Gly Leu Leu
                110                 115                 120

Glu Phe Glu Val Tyr Leu Glu Tyr Leu Gln Asn Arg Phe Glu Ser
                125                 130                 135

Ser Glu Glu Gln Ala Arg Ala Val Gln Met Ser Thr Lys Val Leu
                140                 145                 150

Ile Gln Phe Leu Gln Lys Lys Ala Lys Asn Leu Asp Ala Ile Thr
                155                 160                 165

Thr Pro Asp Pro Thr Thr Asn Ala Ser Leu Leu Thr Lys Leu Gln
                170                 175                 180

Ala Gln Asn Gln Trp Leu Gln Asp Met Thr Thr His Leu Ile Leu
                185                 190                 195

Arg Ser Phe Lys Glu Phe Leu Gln Ser Ser Leu Arg Ala Leu Arg
                200                 205                 210

Gln Met

<210> SEQ ID NO 15
```

```
<211> LENGTH: 320
<212> TYPE: PRT
<213> ORGANISM: Homo sapiens

<400> SEQUENCE: 15

Met Gly Ala Ala Arg Ser Pro Pro Ser Ala Val Pro Gly Pro Leu
 1               5                  10                  15

Leu Gly Leu Leu Leu Leu Leu Gly Val Leu Ala Pro Gly Gly
                20                  25                  30

Ala Ser Leu Arg Leu Leu Asp His Arg Ala Leu Val Cys Ser Gln
                35                  40                  45

Pro Gly Leu Asn Cys Thr Val Lys Asn Ser Thr Cys Leu Asp Asp
                50                  55                  60

Ser Trp Ile His Pro Arg Asn Leu Thr Pro Ser Ser Pro Lys Asp
65                  70                  75

Leu Gln Ile Gln Leu His Phe Ala His Thr Gln Gln Gly Asp Leu
                80                  85                  90

Phe Pro Val Ala His Ile Glu Trp Thr Leu Gln Thr Asp Ala Ser
                95                 100                 105

Ile Leu Tyr Leu Glu Gly Ala Glu Leu Ser Val Leu Gln Leu Asn
               110                 115                 120

Thr Asn Glu Arg Leu Cys Val Arg Phe Glu Phe Leu Ser Lys Leu
               125                 130                 135

Arg His His His Arg Arg Trp Arg Phe Thr Phe Ser His Phe Val
               140                 145                 150

Val Asp Pro Asp Gln Glu Tyr Glu Val Thr Val His His Leu Pro
               155                 160                 165

Lys Pro Ile Pro Asp Gly Asp Pro Asn His Gln Ser Lys Asn Phe
               170                 175                 180

Leu Val Pro Asp Cys Glu His Ala Arg Met Lys Val Thr Thr Pro
               185                 190                 195

Cys Met Ser Ser Gly Ser Leu Trp Asp Pro Asn Ile Thr Val Glu
               200                 205                 210

Thr Leu Glu Ala His Gln Leu Arg Val Ser Phe Thr Leu Trp Asn
               215                 220                 225

Glu Ser Thr His Tyr Gln Ile Leu Leu Thr Ser Phe Pro His Met
               230                 235                 240

Glu Asn His Ser Cys Phe Glu His Met His His Ile Pro Ala Pro
               245                 250                 255

Arg Pro Glu Glu Phe His Gln Arg Ser Asn Val Thr Leu Thr Leu
               260                 265                 270

Arg Asn Leu Lys Gly Cys Cys Arg His Gln Val Gln Ile Gln Pro
               275                 280                 285

Phe Phe Ser Ser Cys Leu Asn Asp Cys Leu Arg His Ser Ala Thr
               290                 295                 300

Val Ser Cys Pro Glu Met Pro Asp Thr Pro Glu Pro Ile Pro Asp
               305                 310                 315

Tyr Met Pro Leu Trp
               320

<210> SEQ ID NO 16
<211> LENGTH: 543
<212> TYPE: DNA
<213> ORGANISM: Homo sapiens

<400> SEQUENCE: 16
```

```
atggactggc ctcacaacct gctgtttctt cttaccattt ccatcttcct      50
ggggctgggc cagcccagga gccccaaaag caagaggaag gggcaagggc     100
ggcctgggcc cctggcccct ggccctcacc aggtgccact ggacctggtg     150
tcacggatga aaccgtatgc ccgcatggag gagtatgaga ggaacatcga     200
ggagatggtg gcccagctga ggaacagctc agagctggcc cagagaaagt     250
gtgaggtcaa cttgcagctg tggatgtcca acaagaggag cctgtctccc     300
tggggctaca gcatcaacca cgaccccagc cgtatccccg tggacctgcc     350
ggaggcacgg tgcctgtgtc tgggctgtgt gaacccttc accatgcagg      400
aggaccgcag catggtgagc gtgccggtgt cagccaggt tcctgtgcgc      450
cgccgcctct gcccgccacc gccccgcaca gggccttgcc gccagcgcgc     500
agtcatggag accatcgctg tgggctgcac ctgcatcttc tga            543

<210> SEQ ID NO 17
<211> LENGTH: 594
<212> TYPE: DNA
<213> ORGANISM: Homo sapiens

<400> SEQUENCE: 17
atgacgctcc tccccggcct cctgtttctg acctggctgc acacatgcct      50
ggccccaccat gaccctcccc tcaggggggca ccccacagt cacggtaccc    100
cacactgcta ctcggctgag gaactgcccc tcggccaggc cccccacac      150
ctgctggctc gaggtgccaa gtggggggcag gctttgcctg tagccctggt    200
gtccagcctg gaggcagcaa gccacagggg gaggcacgag aggccctcag     250
ctacgaccca gtgcccggtg ctgcggccgg aggaggtgtt ggaggcagac     300
acccaccagc gctccatctc accctggaga taccgtgtgg acacggatga     350
ggaccgctat ccacagaagc tggccttcgc cgagtgcctg tgcagaggct     400
gtatcgatgc acggacgggc cgcgagacag ctgcgctcaa ctccgtgcgg     450
ctgctccaga gcctgctggt gctgcgccgc cggccctgct cccgcgacgg     500
ctcggggctc cccacacctg gggctttgc cttccacacc gagttcatcc      550
acgtccccgt cggctgcacc tgcgtgctgc ccgttcagt gtga            594

<210> SEQ ID NO 18
<211> LENGTH: 9
<212> TYPE: PRT
<213> ORGANISM: Artificial Sequence
<220> FEATURE:
<223> OTHER INFORMATION: HIS tag

<400> SEQUENCE: 18

Gly His His His His His His His His
 1               5

<210> SEQ ID NO 19
<211> LENGTH: 157
<212> TYPE: PRT
<213> ORGANISM: Homo sapiens

<400> SEQUENCE: 19

Val Arg Ser Ser Ser Arg Thr Pro Ser Asp Lys Pro Val Ala His
 1               5                  10                  15
```

```
Val Val Ala Asn Pro Gln Ala Glu Gly Gln Leu Gln Trp Leu Asn
             20                   25                  30

Arg Arg Ala Asn Ala Leu Leu Ala Asn Gly Val Glu Leu Arg Asp
         35                  40                  45

Asn Gln Leu Val Val Pro Ser Glu Gly Leu Tyr Leu Ile Tyr Ser
     50                  55                  60

Gln Val Leu Phe Lys Gly Gln Gly Cys Pro Ser Thr His Val Leu
 65                  70                  75

Leu Thr His Thr Ile Ser Arg Ile Ala Val Ser Tyr Gln Thr Lys
             80                  85                  90

Val Asn Leu Leu Ser Ala Ile Lys Ser Pro Cys Gln Arg Glu Thr
         95                  100                 105

Pro Glu Gly Ala Glu Ala Lys Pro Trp Tyr Glu Pro Ile Tyr Leu
    110                 115                 120

Gly Gly Val Phe Gln Leu Glu Lys Gly Asp Arg Leu Ser Ala Glu
125                 130                 135

Ile Asn Arg Pro Asp Tyr Leu Asp Phe Ala Glu Ser Gly Gln Val
            140                 145                 150

Tyr Phe Gly Ile Ile Ala Leu
            155
```

<210> SEQ ID NO 20
<211> LENGTH: 21
<212> TYPE: DNA
<213> ORGANISM: Artificial Sequence
<220> FEATURE:
<223> OTHER INFORMATION: IL-17R PCR Primer

<400> SEQUENCE: 20
ctgtacctcg agggtgcaga g                                            21

<210> SEQ ID NO 21
<211> LENGTH: 58
<212> TYPE: DNA
<213> ORGANISM: Artificial Sequence
<220> FEATURE:
<223> OTHER INFORMATION: IL-17R PCR Primer

<400> SEQUENCE: 21
cccaagcttg ggtcaatgat gatgatgatg atgatgatgc cacaggggca             50
tgtagtcc                                                           58

<210> SEQ ID NO 22
<211> LENGTH: 328
<212> TYPE: PRT
<213> ORGANISM: Homo sapiens

<400> SEQUENCE: 22

```
Met Gly Ala Ala Arg Ser Pro Pro Ser Ala Val Pro Gly Pro Leu
 1               5                  10                  15

Leu Gly Leu Leu Leu Leu Leu Leu Gly Val Leu Ala Pro Gly Gly
             20                  25                  30

Ala Ser Leu Arg Leu Leu Asp His Arg Ala Leu Val Cys Ser Gln
         35                  40                  45

Pro Gly Leu Asn Cys Thr Val Lys Asn Ser Thr Cys Leu Asp Asp
     50                  55                  60

Ser Trp Ile His Pro Arg Asn Leu Thr Pro Ser Ser Pro Lys Asp
 65                  70                  75
```

```
Leu Gln Ile Gln Leu His Phe Ala His Thr Gln Gln Gly Asp Leu
            80                  85                  90

Phe Pro Val Ala His Ile Glu Trp Thr Leu Gln Thr Asp Ala Ser
            95                 100                 105

Ile Leu Tyr Leu Glu Gly Ala Glu Leu Ser Val Leu Gln Leu Asn
           110                 115                 120

Thr Asn Glu Arg Leu Cys Val Arg Phe Glu Phe Leu Ser Lys Leu
           125                 130                 135

Arg His His His Arg Arg Trp Arg Phe Thr Phe Ser His Phe Val
           140                 145                 150

Val Asp Pro Asp Gln Glu Tyr Glu Val Thr Val His His Leu Pro
           155                 160                 165

Lys Pro Ile Pro Asp Gly Asp Pro Asn His Gln Ser Lys Asn Phe
           170                 175                 180

Leu Val Pro Asp Cys Glu His Ala Arg Met Lys Val Thr Thr Pro
           185                 190                 195

Cys Met Ser Ser Gly Ser Leu Trp Asp Pro Asn Ile Thr Val Glu
           200                 205                 210

Thr Leu Glu Ala His Gln Leu Arg Val Ser Phe Thr Leu Trp Asn
           215                 220                 225

Glu Ser Thr His Tyr Gln Ile Leu Leu Thr Ser Phe Pro His Met
           230                 235                 240

Glu Asn His Ser Cys Phe Glu His Met His His Ile Pro Ala Pro
           245                 250                 255

Arg Pro Glu Glu Phe His Gln Arg Ser Asn Val Thr Leu Thr Leu
           260                 265                 270

Arg Asn Leu Lys Gly Cys Cys Arg His Gln Val Gln Ile Gln Pro
           275                 280                 285

Phe Phe Ser Ser Cys Leu Asn Asp Cys Leu Arg His Ser Ala Thr
           290                 295                 300

Val Ser Cys Pro Glu Met Pro Asp Thr Pro Glu Pro Ile Pro Asp
           305                 310                 315

Tyr Met Pro Leu Trp His His His His His His His
           320                 325

<210> SEQ ID NO 23
<211> LENGTH: 175
<212> TYPE: PRT
<213> ORGANISM: Artificial Sequence
<220> FEATURE:
<223> OTHER INFORMATION: IL-17B His tag

<400> SEQUENCE: 23

Ile Phe Leu Gly Leu Gly Gln Pro Arg Ser Pro Lys Ser Lys Arg
  1               5                  10                  15

Lys Gly Gln Gly Arg Pro Gly Pro Leu Ala Pro Gly Pro His Gln
                 20                  25                  30

Val Pro Leu Asp Leu Val Ser Arg Met Lys Pro Tyr Ala Arg Met
                 35                  40                  45

Glu Glu Tyr Glu Arg Asn Ile Glu Glu Met Val Ala Gln Leu Arg
                 50                  55                  60

Asn Ser Ser Glu Leu Ala Gln Arg Lys Cys Glu Val Asn Leu Gln
                 65                  70                  75

Leu Trp Met Ser Asn Lys Arg Ser Leu Ser Pro Trp Gly Tyr Ser
                 80                  85                  90
```

-continued

Ile Asn His Asp Pro Ser Arg Ile Pro Val Asp Leu Pro Glu Ala
                95                 100                 105

Arg Cys Leu Cys Leu Gly Cys Val Asn Pro Phe Thr Met Gln Glu
            110                 115                 120

Asp Arg Ser Met Val Ser Val Pro Val Phe Ser Gln Val Pro Val
        125                 130                 135

Arg Arg Arg Leu Cys Pro Pro Pro Arg Thr Gly Pro Cys Arg
    140                 145                 150

Gln Arg Ala Val Met Glu Thr Ile Ala Val Gly Cys Thr Cys Ile
155                 160                 165

Phe Gly His His His His His His His
                170                 175

<210> SEQ ID NO 24
<211> LENGTH: 206
<212> TYPE: PRT
<213> ORGANISM: Artificial Sequence
<220> FEATURE:
<223> OTHER INFORMATION: IL-17C-His tag

<400> SEQUENCE: 24

Met Thr Leu Leu Pro Gly Leu Leu Phe Leu Thr Trp Leu His Thr
  1               5                  10                  15

Cys Leu Ala His His Asp Pro Ser Leu Arg Gly His Pro His Ser
                 20                  25                  30

His Gly Thr Pro His Cys Tyr Ser Ala Glu Glu Leu Pro Leu Gly
             35                  40                  45

Gln Ala Pro Pro His Leu Leu Ala Arg Gly Ala Lys Trp Gly Gln
         50                  55                  60

Ala Leu Pro Val Ala Leu Val Ser Ser Leu Glu Ala Ala Ser His
     65                  70                  75

Arg Gly Arg His Glu Arg Pro Ser Ala Thr Thr Gln Cys Pro Val
                 80                  85                  90

Leu Arg Pro Glu Glu Val Leu Glu Ala Asp Thr His Gln Arg Ser
                 95                 100                 105

Ile Ser Pro Trp Arg Tyr Arg Val Asp Thr Asp Glu Asp Arg Tyr
                110                 115                 120

Pro Gln Lys Leu Ala Phe Ala Glu Cys Leu Cys Arg Gly Cys Ile
                125                 130                 135

Asp Ala Arg Thr Gly Arg Glu Thr Ala Ala Leu Asn Ser Val Arg
                140                 145                 150

Leu Leu Gln Ser Leu Leu Val Leu Arg Arg Arg Pro Cys Ser Arg
                155                 160                 165

Asp Gly Ser Gly Leu Pro Thr Pro Gly Ala Phe Ala Phe His Thr
                170                 175                 180

Glu Phe Ile His Val Pro Val Gly Cys Thr Cys Val Leu Pro Arg
                185                 190                 195

Ser Val Gly His His His His His His His
                200                 205

<210> SEQ ID NO 25
<211> LENGTH: 271
<212> TYPE: PRT
<213> ORGANISM: Homo sapiens

<400> SEQUENCE: 25

Met Ala Lys Val Pro Asp Met Phe Glu Asp Leu Lys Asn Cys Tyr

-continued

```
                1               5              10              15
Ser Glu Asn Glu Glu Asp Ser Ser Ile Asp His Leu Ser Leu
                       20              25              30

Asn Gln Lys Ser Phe Tyr His Val Ser Tyr Gly Pro Leu His Glu
                       35              40              45

Gly Cys Met Asp Gln Ser Val Ser Leu Ser Ile Ser Glu Thr Ser
                       50              55              60

Lys Thr Ser Lys Leu Thr Phe Lys Glu Ser Met Val Val Ala
                       65              70              75

Thr Asn Gly Lys Val Leu Lys Lys Arg Arg Leu Ser Leu Ser Gln
                       80              85              90

Ser Ile Thr Asp Asp Leu Glu Ala Ile Ala Asn Asp Ser Glu
                       95             100             105

Glu Glu Ile Ile Lys Pro Arg Ser Ala Pro Phe Ser Phe Leu Ser
                      110             115             120

Asn Val Lys Tyr Asn Phe Met Arg Ile Ile Lys Tyr Glu Phe Ile
                      125             130             135

Leu Asn Asp Ala Leu Asn Gln Ser Ile Ile Arg Ala Asn Asp Gln
                      140             145             150

Tyr Leu Thr Ala Ala Ala Leu His Asn Leu Asp Glu Ala Val Lys
                      155             160             165

Phe Asp Met Gly Ala Tyr Lys Ser Ser Lys Asp Ala Lys Ile
                      170             175             180

Thr Val Ile Leu Arg Ile Ser Lys Thr Gln Leu Tyr Val Thr Ala
                      185             190             195

Gln Asp Glu Asp Gln Pro Val Leu Leu Lys Glu Met Pro Glu Ile
                      200             205             210

Pro Lys Thr Ile Thr Gly Ser Glu Thr Asn Leu Leu Phe Phe Trp
                      215             220             225

Glu Thr His Gly Thr Lys Asn Tyr Phe Thr Ser Val Ala His Pro
                      230             235             240

Asn Leu Phe Ile Ala Thr Lys Gln Asp Tyr Trp Val Cys Leu Ala
                      245             250             255

Gly Gly Pro Pro Ser Ile Thr Asp Phe Gln Ile Leu Glu Asn Gln
                      260             265             270

Ala
```

<210> SEQ ID NO 26
<211> LENGTH: 177
<212> TYPE: PRT
<213> ORGANISM: Homo sapiens

<400> SEQUENCE: 26

```
Met Glu Ile Cys Arg Gly Leu Arg Ser His Leu Ile Thr Leu Leu
 1               5              10              15

Leu Phe Leu Phe His Ser Glu Thr Ile Cys Arg Pro Ser Gly Arg
                       20              25              30

Lys Ser Ser Lys Met Gln Ala Phe Arg Ile Trp Asp Val Asn Gln
                       35              40              45

Lys Thr Phe Tyr Leu Arg Asn Asn Gln Leu Val Ala Gly Tyr Leu
                       50              55              60

Gln Gly Pro Asn Val Asn Leu Glu Glu Lys Ile Asp Val Val Pro
                       65              70              75

Ile Glu Pro His Ala Leu Phe Leu Gly Ile His Gly Gly Lys Met
```

-continued

```
                    80                 85                  90
Cys Leu Ser Cys Val Lys Ser Gly Asp Glu Thr Arg Leu Gln Leu
                95                 100                 105
Glu Ala Val Asn Ile Thr Asp Leu Ser Glu Asn Arg Lys Gln Asp
                110                115                 120
Lys Arg Phe Ala Phe Ile Arg Ser Asp Ser Gly Pro Thr Thr Ser
                125                130                 135
Phe Glu Ser Ala Ala Cys Pro Gly Trp Phe Leu Cys Thr Ala Met
                140                145                 150
Glu Ala Asp Gln Pro Val Ser Leu Thr Asn Met Pro Asp Glu Gly
                155                160                 165
Val Met Val Thr Leu Phe Tyr Phe Gln Glu Asp Glu
                170                175
```